US010688132B2

(12) United States Patent
Wang et al.

(10) Patent No.: US 10,688,132 B2
(45) Date of Patent: Jun. 23, 2020

(54) COORDINATING GENE EXPRESSION USING RNA DESTABILIZING ELEMENTS

(71) Applicant: Chimera Bioengineering, Inc., Menlo Park, CA (US)

(72) Inventors: Benjamin Wang, Menlo Park, CA (US); Gusti Zeiner, Pacifica, CA (US); Krista McNally, Foster City, CA (US)

(73) Assignee: Chimera Bioengineering, Inc., Menlo Park, CA (US)

( * ) Notice: Subject to any disclaimer, the term of this patent is extended or adjusted under 35 U.S.C. 154(b) by 14 days.

(21) Appl. No.: 16/446,522

(22) Filed: Jun. 19, 2019

(65) Prior Publication Data

US 2019/0350977 A1    Nov. 21, 2019

Related U.S. Application Data

(63) Continuation of application No. 16/272,679, filed on Feb. 11, 2019.

(60) Provisional application No. 62/630,191, filed on Feb. 13, 2018.

(51) Int. Cl.
| | |
|---|---|
| *C12N 15/63* | (2006.01) |
| *C12Q 1/54* | (2006.01) |
| *A61K 35/17* | (2015.01) |
| *C12N 15/85* | (2006.01) |
| *C12N 15/62* | (2006.01) |
| *C12N 15/113* | (2010.01) |
| *C07K 16/18* | (2006.01) |
| *C07K 14/195* | (2006.01) |
| *A61P 35/00* | (2006.01) |
| *C07K 14/52* | (2006.01) |
| *C07K 14/82* | (2006.01) |
| *A61K 38/20* | (2006.01) |
| *C07K 14/725* | (2006.01) |
| *C07K 16/28* | (2006.01) |
| *A61K 39/00* | (2006.01) |

(52) U.S. Cl.
CPC .......... *A61K 35/17* (2013.01); *A61K 38/208* (2013.01); *A61K 39/0011* (2013.01); *A61P 35/00* (2018.01); *C07K 14/195* (2013.01); *C07K 14/52* (2013.01); *C07K 14/7051* (2013.01); *C07K 14/82* (2013.01); *C07K 16/18* (2013.01); *C07K 16/2803* (2013.01); *C07K 16/2818* (2013.01); *C07K 16/2896* (2013.01); *C12N 15/113* (2013.01); *C12N 15/62* (2013.01); *C12N 15/85* (2013.01); *A61K 2039/5156* (2013.01); *C07K 2317/622* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 2009/0048191 A1 | 2/2009 | Rakoczy et al. | |
| 2010/0316609 A1 | 12/2010 | Dewhurst | |
| 2011/0003385 A1 | 1/2011 | Crabtree | |
| 2013/0245096 A1 | 9/2013 | Abitbol | |
| 2014/0120622 A1 | 5/2014 | Gregory et al. | |
| 2014/0242701 A1 | 8/2014 | Shiku et al. | |
| 2014/0271583 A1 | 9/2014 | Allen-Hoffmann et al. | |
| 2014/0286987 A1 | 9/2014 | Spencer et al. | |
| 2014/0349402 A1 | 11/2014 | Cooper et al. | |
| 2015/0307564 A1 | 10/2015 | Young et al. | |
| 2017/0183407 A1* | 6/2017 | Cooper | C07K 14/7051 |
| 2018/0044415 A1* | 2/2018 | Escarpe | C07K 14/7051 |
| 2018/0044424 A1* | 2/2018 | June | A61K 45/06 |

FOREIGN PATENT DOCUMENTS

| | | |
|---|---|---|
| WO | WO 2015092440 | 6/2015 |
| WO | WO 2015123527 | 8/2015 |
| WO | WO 2015123642 | 8/2015 |
| WO | WO 2015140268 | 9/2015 |
| WO | WO 2015142661 | 9/2015 |
| WO | WO 2015142675 | 9/2015 |
| WO | WO 2015193406 | 12/2015 |
| WO | WO 2016028896 | 2/2016 |
| WO | WO 2016126608 | 8/2016 |

(Continued)

OTHER PUBLICATIONS

Maridana et al Abstract 1530: A multifunctional role for adjuvant anti-4-1 BB therapy in augmenting antitumor responses by CAR T cells Proceedings of the American Association for Cancer Research Annual Meeting 2018; Apr. 14-18, 2018; Chicago, IL. Philadelphia (PA): AACR; Cancer Res 2018;78(13 Suppl):Abstract nr 1530.*
Wang et al., Metabolic checkpoints in activated T cells Nature Immunology vol. 13 No. 10 Oct. 2012; pp. 907-915.*
Wieten et al A Novel Heat-Shock Protein Coinducer Boosts Stress Protein Hsp70 to Activate T Cell Regulation of Inflammation in Autoimmune Arthritis Arthritis & Rheumatism vol. 62, No. 4, Apr. 2010, pp. 1026-1035.*
Chester et al 4-1BB agonism: adding the accelerator to cancer immunotherapy Cancer Immunol Immunother (2016) 65:1243-1248.*
Kovarik et al., Review article Posttranscriptional regulation of cytokine expression Cytokine 89:21-26 (2017).*

(Continued)

*Primary Examiner* — Maria G Leavitt
(74) *Attorney, Agent, or Firm* — HelixIP LLP

(57) ABSTRACT

Control Devices are disclosed including RNA destabilizing elements (RDE), and RNA control devices, combined with transgenes, including Chimeric Antigen Receptors (CARs) in eukaryotic cells. RDEs can be combined with RNA control devices to make RDEs that include ligand mediated control. These smart RDEs and other RDEs can be used to optimize expression of transgenes, e.g., CARs, in the eukaryotic cells so that, for example, effector function is optimized. CARs and transgene payloads can also be engineered into eukaryotic cells so that the transgene payload is expressed and delivered at desired times from the eukaryotic cell.

17 Claims, 11 Drawing Sheets

Specification includes a Sequence Listing.

(56) References Cited

FOREIGN PATENT DOCUMENTS

| WO | WO 2016/149254 | 9/2016 |
|---|---|---|
| WO | WO 2017/149515 | 9/2017 |

OTHER PUBLICATIONS

Aldape et al., Glioblastoma: pathology, molecular mechanisms and markers Acta Neuropathol (2015) 129:829-848.*
Rodriguez Chimeric antigen receptor T-cell therapy for glioblastoma Translational Research vol. 187, Sep. 2017, pp. 93-102.*
Iwamoto et al., A general chemical method to regulate protein stability in the mammalian nervous system, 2010, Chem & Biol vol. 17, pp. 981-988.
Rakhit et al, Evaluation of FKBP and DHFR based destabilizing domains in *Saccharomyces cerivisiae*, 2011, Bioorg & Med Chem Lett vol. 21, pp. 4965-4968.
Jena et al., Redirecting T-cell specificity by introducing a tumor-specific chimeric antigen receptor, 2010, Blood vol. 116, pp. 1035-1044.
Nielsen et al., Split-receptors in the tachykinin neurokinin-1 system, 1998, Eur. J. Biochem. vol. 251, pp. 217-226.
Christopherson et al., Classfication of AML using a monoclonal antibody microarray, 2006, Meth in Mocl Med vol. 125, pp. 241-251.
Kondo et al., Binding of glyceraldehyde-3-phoisphate dehydrogenase to the cis-acting element of structure-anchored . . . , 2011, Biochem Biophys Res Comm vol. 405, pp. 382-387.
Palmer et al, Glucose metabolism regulates T cell activation, differentiation, and functions, 2015, Frontiers Immunol vol. 5, pp. 1-6.
Kloss et al, Combinatorial antigen recognition with balanced signalling promotes selective tumor eradication . . . , 2013, Nat Biotechnol vol. 31, pp. 71-75.
Adusumilli et al., Regional Delivery of Mesothelin-Targeted CAR T-cell Therapy Generates Potent . . . Tumor Immunity, Nov. 2014, Sci. Transl. Med. 6:261ra151.
Aranda et al., Adoptive Cell Transfer for Anticancer Immunotherapy, Apr. 2015, OncoImmunol. 3:5, e28344.
Auslander, et al., From Gene Switches to Mammalian Designer Cells: Present and Future Prospects, Mar. 2013, Trends Biotechnol. 31:155-168.
Baker et al., Structural and Dynamic Control of T-cell Receptor Specificity, Cross-Reactivity, and Binding Mechanism, 2012, Immunol. Rev. 250:10-31.
Beilstein, et al., Conditional Control of Mammalian Gene Expression by Tetracycline-Dependent Hammerhead Ribozymes, Sep. 2014, Synth. Biol. 4:526-534.
Berens, et al., RNA Aptamers as Genetic Control Devices: The Potential of Riboswitches as Synthetic Elements for Regulating Gene Expression, 2015, Biotechnol. 10:246-257.
Bonifant, et al., Toxicity and Management in CAR T-cell Therapy, 2016, Oncolytics 3:16011.
Bray, et al., On-Site CAR Parking, 2015, Sci. Transl. Med. 7:275ra22.
Brayer et al., Developing Strategies in the Immunotherapy of Leukemias, Jan. 2013, Cancer Control 20:49-59.
Brentjens, et al., Adoptive Therapy of Cancer with T cells Genetically Targeted to Tumor Associated Antigens Through . . . , May 2011, Am Soc Gene Cell Therap., presentation.
Brudno et al., Allogenic T Cells That Express and Anti-CD19 Chimeric Antigen Receptor Induce Remissions of B-cell . . . , 2016, Am Soc Clin Oncol 34.
Buckley et al., Update on Antigen-Specific Immunotherapy of Acute Myeloid Leukemia, 2015, Curr. Hematol. Malig. Rep. 10:65-75.
Budde et al., Combining a CD20 Chimeric Antigen Receptor and an Inducible Caspase 9 Suicide Switch to Improve the Efficacy . . . , Dec. 2013, PLoS One 8:e82742.
Cantelmo, et al., Inhibition of the Glycolytic Activator PFKFB3 in Endothelium Induces Tumor Vessel Normalization . . . , Dec. 2016, Cancer Cell 30:968-985.

Caruso et al., Tuning Sensitivity of CAR to EGFR Density Limits Recognition of Normal Tissue While Maintaining . . . , 2015, Cancer Res. 75:3505-3518.
Chakravarti et al., Synthetic Biology in Cell-Based Cancer Immunotherapy, 2015, Trends Biotechnol. 33:449-461.
Chang et al., Posttranscriptional Control of T Cell Effector Function by Aerobic Glycolysis, Jun. 2013, Cell 153:1239-1251.
Chang et al., Identification and Selective Expansion of Functionally Superior T cells Expressing Chimeric Antigen Receptors, 2015, J. Transl. Med. 13:161.
Cheadle et al., CAR T cells: Driving the Road from the Laboratory to the Clinic, 2013, Immunol. Rev. 257:91-106.
Chen et al., Genetic Control of Mammalian T-cell Prolideration with Synthetic RNA Regulatory Systems, 2010, Proc. Natl Acad. Sci. 107:8531-8536.
Chen et al., Efficient Gene Editing in Primary Human T cells, Nov. 2015, Trends Immunol. 36:667-669.
Cooper et al., Moving from Tinkering in the Garage to Assembly Line Production: the Manufacture of Genetically Modified T cells . . . , 2015, Cancer Gene Therap. 22:64-66.
Darcy et al., Adoptive Immnotherapy: a New Era for the Treatment of Cancer, 2015, Immunotherap. 7:469-471.
Davila et al., Efficacy and Toxicity Management of 19-28z CAR T cell Therapy in B cell Acute Lymphoblastic Leukemia, Feb. 2014, Sci Transl Med 6:224ra25.
Di Stasi et al., Inducible Apoptosis as a Safety Switch for Adoptive Cell Therapy, 2011, N. Engl. J. Med. 265:1673-83.
Dotti et al., Design and Development of Therapies Using Chimeric Antigen Receptor-Expressing T cells, Jan. 2014, Immunol. Rev. 257:107-126.
Elert et al., Calling Cells to Arms, Dec. 2013, Nature 504:S2-S3.
Elfakess et al., Unique Translation Initiation of mRNAs-Containing TISU Element, Jun. 2011, Nucl. Acids. Res. 39:7598-7609.
Ellebrecht et al., Reengineering Chimeric Antigen Receptor T cells for Targeted Therapy of Autoimmune Disease, Jul. 2016, Science 353:179-184.
Farajnia et al., Development Trends for Generation of Single-Chain Antibody Fragments, Aug. 2014, Immunopharmacol. Immunotoxicol. 36:297-308.
Federov et al., PD-1 and CTLA-4 Based Inhibitory Chimeric Antigen Receptors (iCARs) Divert Off-Target Immunotherapy . . . , Dec. 2013, Sci. Transl. Med. 5:215ra172.
Festuccia et al., Allogenic Stem Cell Transplantation in Multiple Myeloma: Immunotherapy and New Drugs, Jun. 2015, Expert Opin. Biol. Therapy 15:857-872.
Garber et al., Adoptive T-cell Therapy for Leukemia, 2014, Molc. Cell. Therap. 2:25-pp. 1-22.
Garcia-Sanz et al., Translational Control: a General Mechanism for Gene Regulation During T cell Activation, 1998, FASEB J. 12:299-306.
Ghorashian et al., CD19 Chimeric Antigen Receptor T cell Therapy for Haematological Malignancies, Mar. 2015, Brit, J. Haematol. 169:463-478.
Grada et al., TanCAR: A Novel Bispecific Chimeric Antigen Receptor for Cancer Immunotherapy, 2013, Molc. Therap. Nucl. Acids 2:e105.
Hamilton et al., Delineation of a Novel Pathway that Regulates CD154 (CD40 Ligand) Expression, 2003, Molc. Cell. Biol. 23:510-525.
Hjelm et al., Mifepristone-Inducible Transgene Expression in Neural Progenitor Cells in vitro and in vivo, 2016, Gene Therap. 23:424-437.
Horton et al., Recent Advances in Acute Myeloid Leukemia Stem Cell Biology, 2012, Haematolog. 97:966-974.
Huang et al., Driving an Improved CAR for Cancer Immunotherpy, 2016, J. Clin. Invest. 126:2795-2798.
Hudecek et al., The Nonsignaling Extracellular Spacer Domain of Chimeric Antigen Receptors is Decisive for in Vivo . . . , Sep. 2014, Cancer Immunol. Res. 3:125-135.
Hurton et al., Tethered IL-15 Augments Antitumor Activity and Promotes a Stem-Cell Memory Subset in Tumor-Specific T cells, Nov. 2016, Proc. Natl Acad Sci 113:E7788-E7797.

(56) References Cited

OTHER PUBLICATIONS

Hussaini et al., Targeting CD123 in AML Using a T-cell Directed Dual-Affinity Re-Targeting (DART) Platform, Nov. 2015, Blood 127:122-131.
Iwamoto et al., A General Chemical Method to Regulate Protein Stability in the Mammalian Central Nervous System, 2010, Chem Biol 17:981-988.
Jensen et al., Enhancing the IQ of CAR Modified T Cells, 2015, Powerpoint Slides.
Jensen et al., Mathematical Modeling of Chimeric TCR Triggering Predicts the Magnitude of target Lysis and its Impairment by TCR . . . , 2010, J. Immunol. 184:4284-4294.
Jensen et al., Design and Implementation of Adoptive Therapy with Chimeric Antigen Receptor-Modified T cells, 2014, Immunol. Rev. 257:127-144.
Jensen, Synthetic Immunobiology Boosts the IQ of T cells, Oct. 2015, Science 350:514-515.
Jensen et al., Designing Chimeric Antigen Receptors to Effectively and Safely Target Tumors, 2015, Curr. Opin. Immunol. 33:9-15.
Johnson et al., Rational Development and Characterization of Humanized Anti-EGFR Variant III Chimeric Antigen Receptor . . . , Feb. 2015, Sci. Transl. Med. 7:275ra22.
Juillerat et al., Design of Chimeric Antigen Receptors with Intergrated Controllable Transient Functions, 2016, Sci. Rep. 6:18950.
June, Drugging the Undruggable Ras—Immunotherapy to the Rescue? 2016, N. Eng. J. Med. 375:2286-2289.
Kakarla et al., CAR T cells for Solid Tumors: Armed and Ready to Go? Mar.-Apr. 2014, Cancer J. 20:151-155.
Kalos et al., Adoptive T cell Transfer for Cancer Immunotherapy in the Era of Synthetic Biology, Jul. 2013, Immunity 39:49-60.
Kawalekar et al., Distinct Signaling of Coreceptors Regulates Specific Metabolism Pathways and Impacts Memory Development . . . , 2016, Immunity 44:380-390.
Kebriaei et al., Future of Therapy in Acute Lymphoblastic Leukemia (ALL)—Potential Role of Immune-Based Therapies, 2015, Curr. Hematol. Malig. Rep. 10:76-85.
Kebriaei et al., Phase I Trials Using Sleeping Beuaty to Generate CD19-Specific CAR T cells, 2016, J. Clin. Invest. 126:3363-3376.
Kershaw et al., Clinical Application of Genetically Modified T cells in Cancer Therapy, May 2014, Clin. Transl. Immunol. 3:e16.
Kim et al., Highly Efficient RNA-Guided Genome Editing in Human Cells Via Delivery of Purified Cas9 Ribonucleoproteins, Jun. 2014, Gen. Res. 24:1012-1019.
Kis et al., Mammalian Synthetic Biology: Emerging Medical Applications, Mar. 2015, J. R. Soc. Interface 12:20141000.
Kochenderfer et al., Chemotherapy-Refractory Diffuse Large B-cell Lymphoma and Indolent B-cell Malignancies can be Effectively . . . , Aug. 2014, J. CLin. Oncol. 33:540-549.
Ledford, T-cell Therapy Extends Cancer Survival to Years, Dec. 2015, Nature 516:156.
Liang et al., Engineering Biological Systems with Synthetic RNA Molecules, 2011, Molc. Cell 43:915-926.
Lynn et al., Targeting of Folate Receptor-beta on Acute Myeloid Leukemia Blasts with Chimeric Antigen Receptor-Expressing T cells, May 2015, Blood 125:3466-3476.
Lindsten et al., Regulation of Lymphokine Messenger RNA Stability by a Surface-Mediated T Cell Activation Pathway, 1989, Science 244:339-343.
Liu et al., Affinity Tuned ErbB2 or EGFR Chimeric Antigen Receptor T Cells Exhibit an Increased Therapeutic Index Against Tumors in Mice, Sep. 2015, Cancer Res. 75:3596-3607.
Long et al., 4-1BB Cotimulation Ameliorates T cell Exhaustion Induced by Tonic Signaling of Chimeric Antigen Receptors, Jun. 2015, Nat Med 21:581-590.
Marcus et al., Allogenic Chimeric Antigen Receptor-Modified Cells for Adoptive Cell Therapy of Cancer, Mar. 2014, Expert Opin Biol Therap 14:947-954.
Mardiros et al., T cells Expressing CD123-Specific Chimeric Antigen Receptors Exhibit Specific Cytolytic Effector Functions . . . , Sep. 2013, Blood 122:3138-3148.
Maude et al., Chimeric Antigen Receptor T cells for Sustained Remissions in Leukemia, Mar. 2014, N. Eng. J. Med. 371:1507-1517.
Maus et al., Antibody-Modified T cells: CARs Take the Front Seat for Hematologic Malignancies, Apr. 2014, Blood 123:2625-2635.
Mayer, Nucleic Acid Aptamers: Selection, Characterization and Application, 2016, Humana Press, Springer Science.
Morgan et al., Case Report of a Serious Adverse Event Following the Administration of T cells Transduced with a Chimeric Antigen Receptor . . . , 2010, Molc Therap 18:843-851.
Nagy et al., Glyceraldehyde-3-phosphate Dehydrogenase Selectively Binds AU-Rich RNA in the Nad+-Binding Region, 1995, J Biol Chem 270:2755-2763.
Neeson, Lewis-Y Chimeric Antigen Receptor T cells Traffic and Persist in the Bone Marrow of Patients with Lewis-Y Positive AML, undated, Powerpoint SLides.
Nelson et al., Novel Immunotherapies for Hematologic Malignancies, Jan. 2015, Immunol. Rev. 263:90-105.
Newick et al., CAR T cell Therapy for Solid Tumors, Jul. 2016, Ann. Rev. Med. 68:3.1-3.14.
Norelli et al., Clinical Pharmacology of CAR-T cells: Linking Cellular Pharmacodynamics to Pharmacokinetics and Antitumor Effects, 2016, Biochim Biophys Acta 1865:90-100.
Okoye et al., The Protein LEM Promotes CD8+ T cell Immunity Through Effects on Mitochondrial Respiration, May 2015, Science 348:995-1001.
Paszkiewicz et al., Targeted Antibody-Mediated Depletion of Murine CD19 CAR T cells Permanently Reverses B cell Aplasia, 2016, J Clin Ivest 126:4262-4272.
Perales-Puchalt et al., Follicle-Stimulating Hormone Receptor is Expressed by Most Ovarian Cancer Subtypes and is a Safe . . . , 2016, Clin. Cancer Res.
Pizzitola et al., Chimeric Antigen Receptors Against CD33/CD123 Antigens Efficiently Target Primary Acute Myeloid Leukemia Cells in vivo, Aug. 2014, Leukemia 28:1596-1605.
Poirot et al., Multiplex Genome-Edited T-cell Manufacturing Platform for "Off-the-Shelf" Adoptive T-cell Immunotherapies, 2015, Cancer Res 75:3853-3864.
Posey et al., Engineered CAR T cells Targeting the Cancer-Associated Tn-Glycoform of the Membrane Mucin MUC1 Control Adenocarcinoma, 2016, Immunity 44:1444-1454.
Qin et al., Systematic Comparison of Constitutive Promoters and the Doxycycline-Inducible Promoter, 2010, PLoS One 5:e10611.
Rakhit et al., Chemical Biology Strategies for Posttranslational Control of Protein Function, Sep. 2014, Chem Biol 21:1238-1252.
Reddy, Changing Landscape of Immuno-Oncology: CAR-T Therapy and PD1/PDL1 Blockade, 2016, Boston University Theses.
Renert, Novel Immunotherapeutic Approaches to the Treatment of Cancer: Drug Development and Clinical Application, 2016, Springer International Publishing.
Rodgers et al., Switch-Mediated Activation and Retargeting of CAR-T cells for B-cell Malignancies, 2016, Proc Natl Acad Sci 113:E459-E468.
Rosenberg, Cell Transfer Immunotherapy for Metastataic Solid Cancer—What Clinicians Need to Know, 2011, Nat Rev Clin Oncol 8:577-585.
Rosenberg et al., Adoptive Cell Transfer as Personalized Immunotherapy for Human Cancer, Apr. 2015, Science 348:62-68.
Roybal et al., Precision Tumor Recognition by T cells with Combinatorial Antigen-Sensing Circuits, 2016, Cell 164:770-779.
Roybal et al., Engineering T cells with Customized Therapeutic Response Programs Using Synthetic Notch Receptors, 2016, Cell 167:1-14.
Sadelain et al., Sage Harbours for the Integration of New DNA in the Human Genome, 2012, Nat. Rev. 12:51-58.
Sandberg et al., In Cancer Immunotherapy Legal Battle, It's Now Juno v. Novartis, Feb. 2014, Pharma MedTech Bus Intell. 2014900027.
Shi et al., Chimeric Antigen Receptor for Adoptive Immunotherapy of Cancer: Latest Research and Future Prospects, Sep. 2014, Molc Cancer 13:219.
Sommermeyer et al., Chimeric Antigen Receptor-Modified T cells Derived from Defined CD8+ and CD4+ Subsets Confer Superior Antitumor . . . , Feb. 2016 Leukemia 30:492-500.

(56) References Cited

OTHER PUBLICATIONS

Srivastava et al., Engineering CAR-T cells: Design Concepts, Aug. 2015, Trends Immunol 36:494-502.
Sun et al., The Quest for Spatio-Temporal Control of CAR T cells, Dec. 2015, Cell Res. 25:1281-1282.
Tettamanti et al., CD123 AML Targeting by Chimeric Antigen Receptors: A Novel Magic Bullet for AML Therapeutics? May 2014, Oncoimmunol 3:e28835.
Till et al., Adoptive Immunotherapy for Idolent Non-Hodgkin Lymphoma and Mantle Cell Lymphoma Using Genetically Modified . . . , 2008, Blood 112:2261-2271.
Turatti et al., Redirected Activity of Human Antitumor Chimeric Immune Receptors is Governed by Antigen and Receptor Expression Levels . . . , 2007, J Immunotherap 30:684-693.
Turtle et al., CD19 CAR-T cells of Defined CD4+:CD8+ Composition in Adult B cell ALL Patients, 2016, J Clin Ivest 126:2123-2138.
Turtle et al., Immunotherapy of Non-Hodgkin's Lymphoma with a Defined Ratio of CD8+ and CD4+ CD19-Specific Chimeric Antigen Receptor . . . , 2016, Sci Transl Med 8:355ra116.
Vanderlugt et al., Epitope Spreading in Immune-Mediated Diseases: Implications for Immunotherapy, 2002, Nat Rev 2:85-95.
Vigano et al., Functional Avidity: a Measure to Predict the Efficacy of Effector T cells? 2012, Clin Develop Immunol 2012:153863.
Wang et al., ZAP-70: An Essential Kinase in T-cell Signaling, 2010, Cold Spring Barb Perspect Biol 2:a002279.
Wang et al., One-Step Generation of Mice Carrying Mutations in Multiple Genes by CRISPR/Cas-Mediated Genome Engineering, 2013, Cell 153:910-918.
Wang et al., Manufacture of tumor- and virus-specific T lymphocytes for adoptive cell therapies, Feb. 2015, Cancer Gene Therapy 22:85-94.
Watanabe et al., Target Antigen Density Governs the Efficacy of Anti-CD20-CD28-CD3 Zeta Chimeric Antigen Receptor-Modified . . . , Dec. 2014, J Immunol 194:911-920.
Weigand et al., Tetracycline Aptamer-Controlled Regulation of Pre-mRNA Splicing in Yeast, 2007, Nucl Acids Res 35:4179-4185.
Win et al., A Modular and Extensible RNA-Based Gene-Regulatory Platform for Engineering Cellular Function, 2007, Proc Natl Acad Sci 104:14283-14288.
Win et al., Frameworks for Programming Biological Function Through RNA Parts and Devices, 2009, Chem Biol 16:298-310.
Wu et al., Remote Control of Therapeutic T cells Through a Small Molecule-Gated Chimeric Receptor, Sep. 2015, Science 350:aab4077.
Xie et al., Mammalian Designer Cells: Engineering Principles and Biomedical Applications, Jul. 2015, Biotechnol J 10:1005-1018.
Xie et al., Synthetic Biology—Application-Oriented Cell Engineering, 2016, Curr. Opin. Biotechnol. 40:139-148.
Ye et al., Synthetic Mammalian Gene Circuits for Biomedical Applications, 2013, Curr. Opin. Chem Biol 17:910-917.
Zhao et al., Structural Design of Engineered Costimulation Determines Tumor Rejection Kinetics and Persistence of CAR T cells, Oct. 2015, Cancer Cell 28:415-428.
Zheng et al., Protein L: A Novel Reagent for the Detection of Chimeric Antigen Receptor (CAR) Expression by Flow Cytometry, 2012, J Transl Med 10:29.
Muti, ASH Conference Review, 2014.
Zhong et al., Rational Design of Aptazyme Riboswitches for Efficient Control of Gene Expression in Mammalian Cells, Nov. 2016, eLife 5:e18858.
Auslander et al., A ligand-dependent hammerhead ribozyme switch for controlling mammalian gene expression, Molc. Biosys. vol. 6, pp. 807-814 (2010).
Win et al., A modular and estensible RNA-based gene-regulatory platform for engineering cellular function, Proc. Natl Acad. Sci. vol. 104, pp. 14283-286 (2007).
Auslander et al, A ligand-dependent hammerhead ribozyme switch for controlling mammalian gene expression, 2010, Molc Biosys vol. 6, pp. 807-814.
Budde et al., Combining a CD20 chimeric antigen receptor and an inducible caspace 9 suicide switch to improve the effriciacy amd safety of . . . , 2013, PLoS One vol. 8, pp. 1-10.
Cooper et al, T-cell immunotherapies for treating breast cancer, 2011, URL:http://www.dtic.mil/dtic/tr/fulltext/u2/a55488253.pdf.
Grada et al, TanCAR: a novel bispecific chimeric antigen receptor for cancer immunotherapy, 2013, Molc Therapy—Nucl Acids vol. 2, pp. e105.
Iwamoto et al, A general chemical method to regulate protein stability in the mammalian central nervous system, Chem Biol vol. 17, pp. 981-988.
Liu et al, Genetically modified adenoviral vector with the protein transduction domain of Tat improves transfer to CAR-deficient cells, 2009, Biosc Rep vol. 29, pp. 103.
Win et al, A modular and extensible RNA-based gene-regulatory platform for engineering cellular function, 2007, Proc Natl Acad Sci vol. 104, pp. 14283-14288.
Chen et al, Selective degradation of early-response gene mRNAs: functional analysis of sequence features of the Au-rich elements, 1994, Mol Cell Biol vol. 14, pp. 8471-82.
Drury et al, FasL expression in activated T-lymphocytes involves HuR mediated stabilization, 2010, J. Biol. Chem. vol. 285, pp. 31130-31138.
Larsen et al, Sensitivity to restimulation-induced cell death is linked to glycolytic metabolism in human T-cells, 2016, J. Immunol. vol. 198, pp. 147-155.

* cited by examiner

SEQUENCE LISTING

<160> NUMBER OF SEQ ID NOS: 25

<210> SEQ ID NO 1
<211> LENGTH: 5
<212> TYPE: RNA
<213> ORGANISM: Artificial Sequence
<220> FEATURE:
<223> OTHER INFORMATION: AU repeat element

<400> SEQUENCE: 1 auuua                                                                    5

<210> SEQ ID NO 2
<211> LENGTH: 13
<212> TYPE: RNA
<213> ORGANISM: Artificial Sequence
<220> FEATURE:
<223> OTHER INFORMATION: AU rich element

<400> SEQUENCE: 2
auuuauuuau uua                                                          13

<210> SEQ ID NO 3
<211> LENGTH: 5
<212> TYPE: RNA
<213> ORGANISM: Artificial Sequence
<220> FEATURE:

-continued

```
<223> OTHER INFORMATION: GU rich repeat element

<400> SEQUENCE: 3 uuguu                                                                   5

<210> SEQ ID NO 4
<211> LENGTH: 7
<212> TYPE: RNA
<213> ORGANISM: Artificial Sequence
<220> FEATURE:
<223> OTHER INFORMATION: GU rich repeat element

<400> SEQUENCE: 4 uggggau                                                                 7

<210> SEQ ID NO 5
<211> LENGTH: 5
<212> TYPE: RNA
<213> ORGANISM: Artificial Sequence
<220> FEATURE:
<223> OTHER INFORMATION: U rich repeat element

<400> SEQUENCE: 5 guuug                                                                   5

<210> SEQ ID NO 6
<211> LENGTH: 7
<212> TYPE: RNA
<213> ORGANISM: Artificial Sequence
<220> FEATURE:
<223> OTHER INFORMATION: GU rich element

<400> SEQUENCE: 6 uuuguuu                                                                 7

<210> SEQ ID NO 7
<211> LENGTH: 9
<212> TYPE: RNA
<213> ORGANISM: Artificial Sequence
<220> FEATURE:
<223> OTHER INFORMATION: U rich element
<220> FEATURE:
<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (5)..(6)
<223> OTHER INFORMATION: n is a, c, g, or u

<400> SEQUENCE: 7 nnuunnuuu                                                               9

<210> SEQ ID NO 8
<211> LENGTH: 7
<212> TYPE: RNA
<213> ORGANISM: Artificial Sequence
<220> FEATURE:
<223> OTHER INFORMATION: U rich element

<400> SEQUENCE: 8 uuuauuu                                                                 7

<210> SEQ ID NO 9
<211> LENGTH: 7
<212> TYPE: RNA
<213> ORGANISM: Artificial Sequence
```

```
<220> FEATURE:
<223> OTHER INFORMATION: U rich element

<400> SEQUENCE: 9 uuuuuuu                                                                        7

<210> SEQ ID NO 10
<211> LENGTH: 5
<212> TYPE: RNA
<213> ORGANISM: Artificial Sequence
<220> FEATURE:
<223> OTHER INFORMATION: RDE element

<400> SEQUENCE: 10 uuaga                                                                          5

<210> SEQ ID NO 11
<211> LENGTH: 5
<212> TYPE: RNA
<213> ORGANISM: Artificial Sequence
<220> FEATURE:
<223> OTHER INFORMATION: RDE element

<400> SEQUENCE: 11 aguuu                                                                          5

<210> SEQ ID NO 12
<211> LENGTH: 9
<212> TYPE: RNA
<213> ORGANISM: Artificial Sequence
<220> FEATURE:
<223> OTHER INFORMATION: RDE element

<400> SEQUENCE: 12 uuauuuauu                                                                      9

<210> SEQ ID NO 13
<211> LENGTH: 4
<212> TYPE: RNA
<213> ORGANISM: Artificial Sequence
<220> FEATURE:
<223> OTHER INFORMATION: RDE element

<400> SEQUENCE: 13 uuga                                                                           4

<210> SEQ ID NO 14
<211> LENGTH: 7
<212> TYPE: RNA
<213> ORGANISM: Artificial Sequence
<220> FEATURE:
<223> OTHER INFORMATION: RDE element

<400> SEQUENCE: 14 ugggau                                                                         7

<210> SEQ ID NO 15
<211> LENGTH: 9
<212> TYPE: RNA
<213> ORGANISM: Artificial Sequence
<220> FEATURE:
<223> OTHER INFORMATION: RDE element

<400> SEQUENCE: 15 cugcugcug                                                                      9
```

<210> SEQ ID NO 16
<211> LENGTH: 5
<212> TYPE: RNA
<213> ORGANISM: Artificial Sequence
<220> FEATURE:
<223> OTHER INFORMATION: RDE element

<400> SEQUENCE: 16 auuga                                                                    5

<210> SEQ ID NO 17
<211> LENGTH: 18
<212> TYPE: PRT
<213> ORGANISM: Thoseaasigna virus 2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 19
<212> TYPE: PRT
<213> ORGANISM: Porcine teschovirus-1

<400> SEQUENCE: 18

Ala Thr Asn Phe Ser Leu Leu Lys Gln Ala Gly Asp Val Glu Glu Asn
1               5                   10                  15

Pro Gly Pro

<210> SEQ ID NO 19
<211> LENGTH: 20
<212> TYPE: PRT
<213> ORGANISM: Equine rhinitis A virus

<400> SEQUENCE: 19

Gln Cys Thr Asn Tyr Ala Leu Leu Lys Leu Ala Gly Asp Val Glu Ser
1               5                   10                  15

Asn Pro Gly Pro
            20

<210> SEQ ID NO 20
<211> LENGTH: 22
<212> TYPE: PRT
<213> ORGANISM: foot and mouth disease virus

<400> SEQUENCE: 20

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 21
<211> LENGTH: 282
<212> TYPE: DNA
<213> ORGANISM: Homo sapiens

<400> SEQUENCE: 21
taattaagtg cttcccactt aaaacatatc aggccttcta tttatttaaa tatttaaatt      60
ttatatttat tgttgaatgt atggtttgct acctattgta actattattc ttaatcttaa     120
aactataaat atggatcttt tatgattctt tttgtaagcc ctaggggctc taaaatggtt     180

```
tcacttattt atcccaaaat atttattatt atgttgaatg ttaaatatag tatctatgta    240
gattggttag taaaactatt taataaattt gataaatata aa                      282

<210> SEQ ID NO 22
<211> LENGTH: 282
<212> TYPE: DNA
<213> ORGANISM: Homo sapiens

<400> SEQUENCE: 22
taattaagtg cttcccactt aaaacatatc aggccttcta tttatttaaa tatttaaatt    60
ttatatttat tgttgaatgt atggtttgct acctattgta actattattc ttaatcttaa   120
aactataaat atggatcttt tatgattgaa tttgtaagcc ctaggggctc taaaatggtt   180
tcacttattt atcccaaaat atttattatt atgttgaatg ttaaatatag tatctatgta   240
gattggttag taaaactatt taataaattt gataaatata aa                     282

<210> SEQ ID NO 23
<211> LENGTH: 585
<212> TYPE: DNA
<213> ORGANISM: Homo sapiens

<400> SEQUENCE: 23
tggttgtcct gcctgcaata tttgaatttt aaatctaaat ctatttatta atatttaaca    60
ttatttatat ggggaatata tttttagact catcaatcaa ataagtattt ataatagcaa   120
cttttgtgta atgaaaatga atatctatta atatatgtat tatttataat tcctatatcc   180
tgtgactgtc tcacttaatc ctttgttttc tgactaatta ggcaaggcta tgtgattaca   240
aggctttatc tcaggggcca actaggcagc caacctaagc aagatcccat gggttgtgtg   300
tttatttcac ttgatgatac aatgaacact tataagtgaa gtgatactat ccagttactg   360
ccggtttgaa aatatgcctg caatctgagc cagtgcttta atggcatgtc agacagaact   420
tgaatgtgtc aggtgaccct gatgaaaaca tagcatctca ggagatttca tgcctggtgc   480
ttccaaatat tgttgacaac tgtgactgta cccaaatgga agtaactca tttgttaaaa    540 ttatcaatat ctaatatata tgaataaagt gtaagttcac aacta                  585

<210> SEQ ID NO 24
<211> LENGTH: 32
<212> TYPE: DNA
<213> ORGANISM: Artificial Sequence
<220> FEATURE:
<223> OTHER INFORMATION: MinP promoter

<400> SEQUENCE: 24
tagagggtat ataatggaag ctcgacttcc ag                                 32

<210> SEQ ID NO 25
<211> LENGTH: 131
<212> TYPE: DNA
<213> ORGANISM: Artificial Sequence
<220> FEATURE:
<223> OTHER INFORMATION: NFAT promoter

<400> SEQUENCE: 25
ggaggaaaaa ctgtttcata cagaaggcgt ggaggaaaaa ctgtttcata cagaaggcgt    60
ggaggaaaaa ctgtttcata cagaaggcgt agatctagac tctagagggt atataatgga   120
agctcgaatt c                                                        131
```

COORDINATING GENE EXPRESSION
USING RNA DESTABILIZING ELEMENTS

This application is continuation of U.S. application Ser. No. 16/272,679 filed Feb. 11, 2019, which claims priority to U.S. provisional application Ser. No. 62/630,191 filed Feb. 13, 2018.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CBIO030_ST25.txt", a creation date of Feb. 11, 2018, and a size of 9 kilobytes. The Sequence Listing filed via EFS-Web is part of the specification and is incorporated in its entirety by reference herein.

BACKGROUND OF THE INVENTION

Chimeric Antigen Receptors are human engineered receptors that may direct a T-cell to attack a target recognized by the CAR. For example, CAR T cell therapy has been shown to be effective at inducing complete responses against acute lymphoblastic leukemia and other B-cell-related malignancies and has been shown to be effective at achieving and sustaining remissions for refractory/relapsed acute lymphoblastic leukemia (Maude et al., NEJM, 371:1507, 2014). However, dangerous side effects related to cytokine release syndrome (CRS), tumor lysis syndrome (TLS), B-cell aplasia and on-tumor, off-target toxicities have been seen in some patients.

There are currently two extant strategies to control CAR technology. The first is an inducible "kill switch." In this approach, one or more "suicide" genes that initiate apoptotic pathways are incorporated into the CAR construct (Budde et al. PLoS1, 2013 doi:10.1371/journal.pone.0082742). Activation of these suicide genes is initiated by the addition of AP1903 (also known as rimiducid), a lipid-permeable tachrolimus analog that initiates homodimerization of the human protein FKBP12 (Fv), to which the apoptosis-inducing proteins are translationally fused. In the ideal scenario, these kill switches endeavor to sacrifice the long-term surveillance benefit of CAR technology to safeguard against toxicity. However, in vivo, these suicide switches are not likely to realize this goal, as they are operating against powerful selection pressures for CAR T-cells that do not respond to AP1903, a situation worsened by the inimical error-prone retroviral copying associated with the insertion of stable transgenes into patient T-cells. In this scenario, non-responsive CAR T-cell clones will continue to proliferate and kill target cells in an antigen-dependent manner. Thus, kill switch technology is unlikely to provide an adequate safeguard against toxicity.

The second CAR regulatory approach is transient CAR expression, which can be achieved in several ways. In one approach, T-cells are harvested from unrelated donors, the HLA genes are deleted by genome-editing technology and CAR-encoding transgenes are inserted into the genome of these cells. Upon adoptive transfer, these CAR T-cells will be recognized by the recipient's immune system as being foreign and destroyed, thus the CAR exposure in this system is transient. In another transient CAR exposure approach, mRNA of a CAR-encoding gene is introduced into harvested patient T-cells (Beatty, G L 2014. Cancer Immunology Research 2 (2): 112-20. doi:10.1158/2326-6066.CIR-13-0170). As mRNA has a short half-life and is not replicated in the cell or stably maintained, there is no permanent alteration of the CAR-expressing T-cell, thus the CAR expression and activity will be for a short period of time. However, as with the kill-switch approach, these transient CAR exposure approaches sacrifice the surveillance benefit of CARs. Additionally, with these transient systems acute toxicity can be difficult to control.

SUMMARY OF THE INVENTION

In an aspect, the description discloses a eukaryotic cell with a CAR, T-cell receptor, or other targeting polypeptide and a transgene under the control of an RNA Destabilizing Element (RDE). The RDE may control multiple transgenes or multiple RDEs may control multiple transgenes. The multiple transgenes may be arranged serially and/or as a concatemer and/or in other arrangements. Multiple RDEs may be used to regulate a transgene, and these multiple RDEs can be organized as a concatemer, interspersed within a region of the transcript, or located in different parts of the transcript. Multiple transgenes can be regulated by an RDE or a combination of RDEs. The RDEs can be localized in the 3'-UTR, the 5'-UTR and/or an intron. RDEs can include, for example, the RDEs from AU 1 (CD40L), AU 2 (CSF2), AU 3 (CD247), AU 4 (CTLA4), AU 5 (EDN1), AU 6 (IL2RA), AU 7 (SLC2A1), AU 8 (TRAC), AU 9 (CD274), AU 10 (Myc), AU 11 (CD19), AU 12 (IL4), AU 13 (IL5), AU 14 (IL6), AU 15 (IL9), AU 16 (IL10), AU 17 (IL13), AU 18 (FOXP3), AU 19 (TMEM-219), AU 20 (TMEM-219snp), AU 21 (CCR7), AU 22 (SEM-A4D), AU 23 (CDC42-SE2), AU 24 (CD8), AU 27 (bGH), and/or AU 101 (Interferon gamma or IFNg). Other RDEs are disclosed in the following description.

In an aspect, the RDE can be under the control of a RNA control device. Such, Smart RDEs place the RDE control under the regulation of the RNA control device which introduces ligand control to the RDE. The RNA control device can disrupt the RDE when ligand is bound (or not bound) resulting in loss of the RDE control, and when ligand is added (or removed) the RNA control device is inhibited and the RDE structure is available for interaction with RNA binding proteins. The RNA control device could also act upon a portion of the transcript that disrupts the RDE (e.g., the portion of the transcript could form secondary structures with the RDE that inhibit RNA binding proteins from binding to the RDE), when the RNA control device binds (or is free from ligand) the RNA control device disrupts the inhibitory portion of the transcript so it is not available to interact with the RDE, and the RDE is now available to interact with RNA binding proteins. This RNA control device regulation allows the activity of the RDE to be ligand controlled through the action of the RNA control device.

In an aspect, an RDE, combination of RDEs, and/or modified RDEs can be used to provide desired kinetic parameters to the regulation of a gene product including, for example, amount of expression, steady state concentration, $C_{max}$ (maximal concentration of gene product obtained), $T_{max}$ (time to reach $C_{max}$), baseline expression, speed of induction (acceleration), induction rate (velocity), dynamic range also known as fold regulation (induced expression/basal expression), maximal dynamic range ($DR_{max}$), time to $DR_{max}$, area under the curve (AUC), etc. A RDE construct can be made that has a desired set of kinetic parameters to provide the level, degree, temporal, and amount of regulation that is desired. In addition, RDE concatemers can be used to alter the kinetic performance of a construct.

Combinations of RDEs can be used to provide temporal regulation between two or more transgenes. RDEs can be selected to provide maximal rates of expression (and different amounts of maximal expression) at different times following activation of a cell (or induction of expression). This temporal control allows a first transgene encoded polypeptide to alter the state of the cell so that the cell is prepared to be acted upon by a second polypeptide encoded by a second transgene with an RDE that provides later in time expression. This temporal control can also be used to time the expression of two, three or more transgenes following activation of a cell. If the transgene encoded polypeptides are secreted, they can act in a temporal fashion upon target cells. For example, a first transgene polypeptide (with an early expression RDE) could be secreted and act upon a target cell to change its state (e.g., induce the expression of receptor). The second transgene polypeptide is expressed at a later time (under the control of a later expression RDE) and acts upon the target cell with the changed state (e.g., the second protein can be a ligand for the induced receptor).

In an aspect, the RDE can be engineered to increase or decrease the binding affinity of RNA binding protein(s) that interact with the RDE. Altering the affinity of the RNA binding protein can change the timing and response of transgene expression as regulated by the RNA binding protein. In an aspect, the RNA binding protein binding at the RDE is altered by the metabolic state of the cell and changing the binding affinity of the RDE for the RNA binding protein alters the response to and/or timing of transgene expression with the metabolic state of the cell. In an aspect, the RNA binding protein binding at the RDE is altered by the redox state of the cell and changing the binding affinity of the RDE for the RNA binding protein alters the response to and/or timing of transgene expression with the redox state of the cell.

In an aspect, the CAR, T-cell receptor, B-cell receptor, innate immunity receptor, or other targeting receptor or targeting polypeptide recognizes an antigen at the target site (e.g., tumor cell or other diseased tissue/cell) and this activates the cell. The transgene can be another CAR that recognizes a second antigen at the target site and activation of the cell by the first CAR, T-cell receptor or other targeting polypeptide induces the second CAR allowing the eukaryotic cell to recognize the target site by a second antigen. In an aspect, the eukaryotic cell has a first CAR that recognizes an antigen at a target site and this activates a transgene (through an RDE) that encodes a polypeptide that directly or indirectly reduces the activation state of the cell. For example, the transgene may encode a second CAR that recognizes an antigen on healthy tissue so that when the first CAR reacts with antigen at a nontarget cell, the eukaryotic cell will be de-activated by the second CAR interaction with the healthy cell antigen (that is not present or is present in reduced amounts at the target site).

In some aspects, the eukaryotic cell is an immune cell, e.g., a T-cell, a natural killer cell, a B-cell, a macrophage, a dendritic cell, or other antigen presenting cell. In these aspects, activation of the cell by the CAR or changing the metabolic state of the immune cell in other ways can induce expression of the transgene through the RDE. The RDE that controls the transgene can have microRNA binding sites and can be engineered to remove one or more of these microRNA binding sites. The RDE can be bound by the Hu Protein R (HuR). Without wishing to be bound by theory it is expected that HuR can bind to some RDEs, and act to stabilize the mRNA, leading to enhanced translation. Some RDEs can be tied to the glycolytic state of the eukaryotic cell through the enzyme glyceraldehyde 3-phosphate dehydrogenase (GAPDH), other dehydrogenases, other oxidoreductases, or other glycolytic enzymes that can bind to an RDE when the eukaryotic cell is not activated (low glycolytic activity), quiescent, or at rest. When GAPDH or the other enzymes bind to the RDE this can reduce half-life of the RNA with the RDE. In this aspect, CAR activation of the eukaryotic cell (e.g., T-lymphocyte) can induce glycolysis in the cell which reduces GAPDH binding of the RNA, increases half-life of the RNA, which produces increased expression of the transgene encoded in the RNA and controlled by the RDE. Without wishing to be bound by theory, as GAPDH vacates the RDE, HuR or other RDE binding proteins may subsequently bind either the same RDE, or a previously inaccessible RDE (sterically hindered by presence of GAPDH), further stabilizing the mRNA, increasing half-life of the mRNA, and producing further increased expression of the transgene encoded by the RNA and controlled by said RDE. Thus, CAR activation can induce expression of the transgene. In other aspects, other activation of the immune cell can cause GAPDH to engage in glycolysis and so induce expression of the transgene under the control of the RDE.

Expression from the transcript with the RDE(s) can respond to the metabolic state of the cell. For example, the RDE can be bound by metabolic or glycolytic enzymes which couples expression of the transgene to the activation state of the cell through these metabolic or glycolytic enzymes. Some metabolic or glycolytic enzymes bind to RDEs in the transcript and degrade or target for degradation the transcript. When those metabolic or glycolytic enzymes become active, the enzymes no longer bind to the RDEs, the transcripts are stable for a longer period of time, and the transcripts can be translated for this longer period of time. Cells expressing transgenes under the control of such RDEs can also be engineered to express a CAR that can alter the metabolic state of the cell at desired times resulting in expression of the transgene at the desired time. Alternatively, other stimuli can be used to alter the metabolic state of the eukaryotic cell resulting in expression of the transgene. For example, the metabolic state of the cell can be altered to cause transgene expression (or to inhibit expression) by stimuli including, for example, small molecules (e.g., PMA/ionomycin), cytokines, a TCR and costimulatory domain engagement with ligand, oxygen levels, cellular stress, temperature, or light/radiation.

GAPDH binding to the RDE can be increased by introducing into the cell a small molecule that inhibits glycolysis such as, for example, dimethylfumarate (DMF), rapamycin, 2-deoxyglucose, 3-bromophyruvic acid, iodoacetate, fluoride, oxamate, ploglitazone, dichloroacetic acid, or other metabolism inhibitors such as, for example, dehydroepiandrosterone. Other small molecules can be used to reduce GAPDH binding to the RDE. Such small molecules may block the RDE binding site of GAPDH including, for example, CGP 3466B maleate or Heptelidic acid (both sold by Santa Cruz Biotechnology, Inc.), pentalenolactone, or 3-bromopyruvic acid. Other small molecules can be used to analogously inhibit other enzymes or polypeptides from binding to RDEs. Other small molecules can be used to change the redox state of GAPDH, leading to an altered affinity of GAPDH for the RDE. Other small molecules known to interact with GAPDH function, such as vitamin C, saframycin, salicylic acid, insulin, vitamin d3, metformin, or suramin can modify the binding of GAPDH for the RDE. Other molecules can modify the binding of GAPDH for the RDE including trehalose, galactose and other saccharides. Other molecules known to alter GAPDH structure can modify the binding of GAPDH for the RDE including nitric oxide and hydrogen sulfide.

In an aspect, activation of the immune cell induces expression of the transgene that can encode a payload to be delivered at the target (activation) site. The transgene can encode a payload for delivery at the site of CAR activation and/or immune cell activation and/or other receptor activation. The payload can be a cytokine, an antibody, a reporter (e.g., for imaging), a receptor (such as a CAR), or other polypeptide that can have a desired effect at the target site. The payload can remain in the cell, or on the cell surface to modify the behavior of the cell. The payload can be an intracellular protein such as a kinase, phosphatase, metabolic enzyme, an epigenetic modifying enzyme, a gene editing enzyme, etc. The payload can be a gene regulatory RNA, such as, for example, siRNA, microRNAs (e.g., miR155), shRNA, antisense RNA, ribozymes, and the like, or guide RNAs for use with CRISPR systems. The payload can be a nucleic acid (e.g., a vector, or a human artificial chromosome (HAC)). The payload can also be a membrane bound protein such as GPCR, a transporter, etc. The payload can be an imaging agent that allows a target site to be imaged (target site has a desired amount of target antigen bound by the CAR). The payload can be a checkpoint inhibitor, and the CAR and/or other binding protein (e.g., T-cell receptor, antibody or innate immunity receptor) can recognize a tumor associated antigen so the eukaryotic cell preferentially delivers the checkpoint inhibitor at a tumor. The payload can be a cytotoxic compound including, for example, a granzyme, an apoptosis inducer, a cytotoxic small molecule, or complement. The payload can be an antibody, such as for example, an anti-4-1BB agonist antibody (an anti-CD137 antibody), an anti-IL 1b antibody (anti-inflammatory), anti-CD29/anti-VEGF antibody, an anti-CTLA4 antibody, a bispecific antibody (e.g., BiTE), or an anti-CD11b antibody. The payload can be an immune polypeptide, including for example, cytokines (e.g., IL-2, IL-12, IL-15, IL-18), chemokines (e.g., CXCL12), perforins, granzymes, and other immune polypeptides. The payload can be an enzyme including for example, hyaluronidase, or heparinase. The payload can be a polypeptide including for example, CCR2, CCR4, a BiTE (activates immunosuppressed T-cells), soluble CD40 ligand, HSP70, and HSP60. The payload can be a transgene(s) which delivers a virus as a payload. For example, the RDE can control a master control element that controls the expression of the virus genes for replication and coat/envelope proteins. Alternatively, the Rep and coat/envelope proteins can be placed under the control of inducible promoters that are controlled by a regulatory protein, and that regulatory protein can be controlled by an RDE. Still alternatively, the Rep proteins of the virus can be placed under the control of an RDE, and/or the coat/envelope proteins of the virus can be placed under the control of an RDE. As with other payloads this complex payload can use CAR T-cell regulation or any other regulation that induces glycolysis in a cell. Helper constructs in a T cell, or other delivery cell can encode the genes needed for viral replication and viral packaging.

Additional constructs can be employed that encode viral coat/envelope polypeptides for the viral capsid and enzymes for viral replication (Rep proteins), lysis of the host cell, etc. Packaging and other helper constructs can include, but are not limited to, for example, lentiviral packaging (helper) systems (e.g., available from Clontech/Takara and addgene), pSV-A-MLV-env (NIH catalog number: 1065), which contains the amphotropic murine leukemia virus env gene linked to the MLV LTR and an SV origin, wherein the cloning vector is PSV7d; HIVgpt (NIH catalog number: 1067), which is an Xbal-Hpat pHXB2gpt fragment (Drs. A. Fisher and F. Wong-Staal) containing pro-viral and flanking cellular sequences cloned into the HincII-Xbal sit of pBS KS (+/−); PsV-T-MLV-env (NIH catalog number: 3422), which is Ψ-Moloney Murine Leukemia virus DNA (from Richard Mann) cloned into the SV40 expression vector pSV7d at the EcoR1 site; and psPAX2 (equivalent to pCMV δR8.91), wherein the plasmid encodes for the Gag/Pro/Pol genes derived from HIV-1. The promoter is the chicken beta actin promoter and polyadenylation signal is the rabbit beta globin polyA.

Expression from helper constructs (e.g., Rep constructs and/or coat/envelope protein constructs) or the virus (e.g., oncolytic viruses) is placed under the control of an RDE. The RDE can be one that is activated for expression when a receptor activates the host cell (e.g., when receptor binding can alter the energy state of the cell by activating glycolysis or other energy pathways). For example, the Rep and Cap genes of a virus (or helper construct) can be placed under the control of an RDE that provides expression after receptor activation of the host cell (e.g., induction of glycolysis). Other virus genes such as those encoding master switch polypeptides that control transcription, e.g., (for adenovirus) E1A, E1B, E2A, E4ORF6 and/or VARNA can also be placed under the control of an RDE that provides expression after receptor activation of the host cell (or other systems as described above). Using RDEs with virus polypeptides in this manner ties virus production in the host cell to activation of the host cell through the receptor (which binds a ligand at the target site).

A variety of constructs can be delivered as viral payload ranging from full virus to transfer constructs (contain packaging signals and transgenes). Infective constructs can also encode desired transgenes and noninfective constructs can encode polypeptides that kill infected cells but do not produce infective virus (e.g., the construct could include viral functions that lyse the infected cell, or the construct could encode viral proteins that are displayed on the infected cell for recognition by cytotoxic T-cells or natural killer cells). Noninfective constructs can also deliver transgenes to the target cell that alter the genotype and/or phenotype of the target cell. For example, noninfective transfer constructs can deliver transgenes for gene therapy. Transfer constructs are available from addgene as transfer plasmids. Viral payloads can contain polypeptides that serve as marker proteins to assess cell transformation and expression, fusion proteins, polypeptides having a desired biological activity, gene products that can complement a genetic defect, RNA molecules, transcription factors, other gene products that are of interest in regulation and/or expression, and other payloads described herein. The payload may also contain nucleotide sequences that provide a desired effect or regulatory function (e.g., transposons, transcription factors).

The viral payload may be a transgene encoding a gene therapy product. A gene therapy product may include, but is not limited to, a polypeptide, RNA molecule, or other gene product that, when expressed in a target cell, provides a desired effect. The gene therapy product may contain a substitute for a non-functional gene that is absent or mutated in the target cell. The viral payload may be a transgene that will target the cell for killing by the immune system (e.g., cytotoxic T-cells and/or natural killer cells). For example, the transgene could encode the heterologous polypeptide that is displayed on the surface of the infected cell and that cytotoxic T-cells and/or natural killer cells recognize as targets to be killed. For example, the heterologous polypeptide could be a heterologous MHC polypeptide that is incompatible with the host, or a viral polypeptide that will trigger an immune response to destroy the infected cells (the immune system recognizes the cells as virus infected and kills the cells). The transgene could also be one of, for example, a Fas, a TNFαR, a DR3, a DR4, or a DR5 polypeptide (which can act as apoptosis receptors).

A viral payload construct encoding a payload may contain or encode a selectable marker. A selectable marker may comprise a gene sequence or a protein encoded by a gene sequence expressed in a host cell that allows for the identification, selection, and/or purification of the host cell from a population of cells that may or may not express the selectable marker. The selectable marker provides resistance to survive a selection process that would otherwise kill the host cell, such as treatment with an antibiotic. An antibiotic selectable marker may contain one or more antibiotic resistance factors, including but not limited to neomycin resistance (e.g., neo), hygromycin resistance, kanamycin resistance, and/or puromycin resistance.

A payload construct encoding a payload may contain a selectable marker that includes, but is not limited to, β-lactamase, luciferase, β-galactosidase, or a reporter gene as that term is understood in the art, including cell-surface markers, such as CD4 or the truncated nerve growth factor (NGFR) (for GFP, see WO 96/23810; Heim et al., Current Biology, 2:178-182 (1996); Heim et al., Proc. Natl. Acad. Sci. USA, (1995); or Heim et al., Science, 373:663-664 (1995); for β-lactamase, see WO 96/30540); the contents of each of which are herein incorporated by reference in their entirety.

A viral payload containing a nucleic acid for expression in a target cell can be incorporated into the viral genome located between two ITR sequences, or on either side of an asymmetrical ITR engineered with two D regions. A payload construct encoding one or more payloads for expression in a target cell may contain one or more payload or non-payload nucleotide sequences operably linked to at least one target cell-compatible promoter. Such payload constructs can be made from transfer plasmids that are available from addgene. A person skilled in the art will recognize that a target cell may require a specific promoter including, but not limited to, a promoter that is species specific, inducible, tissue-specific, or cell cycle-specific (Parr et al., Nat. Med. 3:1145-9 (1997).

The transgene or payload can be carried on any suitable vector, e.g., a plasmid, which is delivered to a host cell such as the transfer plasmids available from addgene. Plasmids may be engineered such that they are suitable for replication and, optionally, integration in prokaryotic cells, mammalian cells or both. These plasmids contain sequences permitting replication of the transgene in eukaryotes and/or prokaryotes and selection markers for these systems. Selectable markers or reporter genes may include sequences encoding gentamycin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells.

The construct carrying the transgene or payload is transfected into the cell, where it may exist transiently. Alternatively, the transgene may be stably integrated into the genome of the host cell, either chromosomally or as an episome. The transgene may be present in multiple copies, optionally in head-to-head, head-to-tail, or tail-to-tail concatamers.

In some aspects, the expression of CAR, DE-CAR and/or Side-CAR polypeptide is controlled, at least in part, by an RDE that interacts with a glycolytic enzyme with RDE binding activity, e.g., GAPDH. The glycolytic enzyme can bind to the RDE and reduce production of the CAR, DE-CAR, Side-CAR polypeptide, and/or other transgene product. This reduction in polypeptide production can occur because of an inhibition of translation and/or an increase in the rate of mRNA degradation (RDE binding can shorten the half-life of the mRNA). Some RDE binding proteins may reduce translation and enhance degradation of RNA to reduce the level of polypeptide made. The RDE can be an AU rich element from the 3' UTR of a transcript (e.g., a transcript encoding IL-2 or IFN-γ), or can be a modified 3' UTR that has been engineered to remove one or more microRNA sites (e.g., modified 3'-UTRs of IL-2 or IFN-γ). In an aspect, the expression of the transgene, CAR, DE-CAR and/or Side-CAR polypeptide under the control of an RDE bound by a glycolytic enzyme(s), e.g., GAPDH, is increased by increasing the activity of the enzyme(s) in prosecuting glycolysis. The activity of enzymes in glycolysis can be increased by providing the cell with increased glucose in the cell medium, increasing triose isomerase activity in the cell, or providing the cell with a compound that increases glycolysis in the cell, e.g., tamoxifen or glucose. The RDE can bind to Hu Protein R (HuR). Without wishing to be bound by theory it is expected that HuR binds to some AU-rich RDEs and U-rich RDEs, and can act to stabilize the mRNA, leading to enhanced translation. Thus, cell conditions that result in increased HuR expression can increase expression of transgenes with appropriate AU-rich elements and/or U-rich elements, and conditions that reduce HuR expression can decrease expression of these transgenes. HuR interaction with the 3' UTR of the transgene (or native genes) can also be altered by expressing a recombinant transcript containing HuR binding sites. Expression of these transcripts will reduce the amount of HuR available to bind to the transgene transcript or native HuR regulated transcripts and reduce the half-lives of these transcripts resulting in decreased expression.

In an aspect, RDE control can be used to lower CAR expression in a subject which can reduce the availability of CAR polypeptide for immune reactions. This can lower the immunogenicity of transgenic immune cells with the CAR. In part, this lower immunogenicity occurs because the CAR peptide has lower exposure to the immune system.

In an aspect, nucleic acids can be used to boost the response of immune cells upon stimulation of the immune cell. For example, the immune cell can produce higher amounts of immune polypeptides (greater $C_{max}$) with faster kinetics of production. The immune polypeptides can include, for example, cytokines, perforins, granzymes, apoptosis inducing polypeptides, etc. The nucleic acids that boost the immune response can comprise control regions operably linked to nucleic acids encoding RDEs for selected RDE binding proteins, so that upon expression of the nucleic acid into RNA the RDEs in the RNA bind the RDE binding proteins that repress expression of a polypeptide, for example, cytokines, perforins, granzymes, and other immune polypeptides. The expression of the RNAs with the RDEs can poise the eukaryotic cell for expression of polypeptide controlled by RDEs. For example, the expression of RNAs with the RDEs may be done in immune cells to poise the cell for expression of immune polypeptides upon stimulation of the immune cell.

In an aspect, the CAR, DE-CAR, Side-CAR polypeptides, and/or other receptor can be directed against antigens found on acute myeloid leukemia (AML) cells including, for example, CD 33, CD 34, CD 38, CD43, CD 44, CD 45, CD 45RA, CD 47, CD 64, CD 66, CD 123, CD 133, CD 157, CLL-1, CXCR4, LeY, PR1, RHAMM (CD 168), TIM-3, and/or WT1. The monoclonal antibody 293C3-SDIE can be used as the extracellular element for the CAR, DE-CAR and/or Side-CAR polypeptides. (Rothfelder et al., 2015, at ash.confex.com/ash/2015/webprogram/Paper81121.html, which is incorporated by reference in its entirety for all purposes) Other antigens for AML are known in the art and may be the target of the CAR, DE-CAR, Side-CAR, and/or other receptor. An onco-sialylated CD 43 has been associated with acute myeloid leukemia (AML) and this onco-sialylated CD 43 is not found on normal cells and tissue. This onco-sialylated CD 43 is bound by the monoclonal antibody AT14-013, and the variable region of this antibody is used to make an anti-onco sialylated CD 43 CAR. AT14-013 recognizes the unique sialylation epitope found on this onco-sialylated CD 43. This CAR is specific for AML and does not have side reactivity with normal tissue in a subject. In an aspect, the CAR, DE-CAR, Side-CAR polypeptides, and/or other receptor can be directed against antigens found on diffuse large cell B-cell lymphoma (DLBCL) cells including, for example, CD19, CD20, CD22, CD79a, CD5, CD10, and CD43. Other antigens for DLBCL are known in the art and may be the target of the CAR, DE-CAR, Side-CAR, and/or other receptor.

Other antigens that can be targeted by the CAR, DE-CAR, side-CAR or other receptor include, for example, DLL3, HER2, PSCA, CSPG4, EGFRvIII, MSLN (mesothelin), FAP, MUC16 (CA-125), CEA, CD133 (PROM1), IL13Ra, CD171 (L1CAM), CD123, (IL3R), CD33 (SIGLEC3), LeY, GUCY2C, BCMA and/or EPHA2. Eukaryotic cells with CAR, DE-CAR, side-CAR or other receptors targeting these antigens can include a payload such as, for example, one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-12, IL-15, IL-18, INFγ, miRNA (e.g., mir155), and/or CD40 ligand.

The CAR, DE-CAR, Side-CAR polypeptides, and/or other receptor can be directed against antigens found on solid tumors such as, for example, integrins such as αvβ6 (found on numerous solid tumors (including, for example, oral squamous cell cancer, colon cancer, pancreatic cancer, gastric cancer, breast cancer, ovarian cancer, cervical cancer, lung cancer, etc.).

In an aspect, small molecules and other molecules that affect the availability of GAPDH or other RDE binding proteins to bind RDEs can be used to regulate gene expression by GAPDH, other RDE binding glycolysis enzymes, and/or other RDE binding enzymes involved in energy and cell metabolism. Molecules that increase glycolysis in a cell can reduce the amount of GAPDH available for binding to RDEs which can increase translation from transcripts under GAPDH control. Similarly, other glycolysis enzymes and metabolic enzymes can bind to RDEs and activating glycolysis and other energy pathways in the cell can reduce the amount of these enzymes that are available to bind their corresponding RDEs. This reduced binding can increase translation from transcripts controlled by these RDE binding proteins (enzyme binding to the RDE decreases expression) or can decrease translation if enzyme binding has a positive effect on expression. These molecules can also be useful in the treatment of certain types of neural degeneration associated with inflammation and/or autoimmune diseases. These molecules can be used to alter the amount of GAPDH in immune cells so that RDEs are bound and the immune cells reduce expression of RDE regulated genes. Some genes under RDE control in immune cells are associated with inflammation and so, molecules that increase the amount of RDE binding proteins that inhibit the inflammatory associated transcripts could reduce inflammation.

A nucleic acid construct encoding a transcript with selected RDEs can be expressed in an immune cell, for example, a T-lymphocyte. The recombinant transcript with the selected RDEs can bind to and deplete the levels of RDE binding proteins in the T-lymphocyte so that transcripts encoding polypeptides regulated by the depleted RDE binding proteins are expressed at different threshold points of activation for other cellular signals. The use of the RDE constructs can increase the kinetics of expression and/or the Cmax of expression of the polypeptides whose expression is controlled by the RDE.

DETAILED DESCRIPTION OF THE INVENTION

Figure 1:
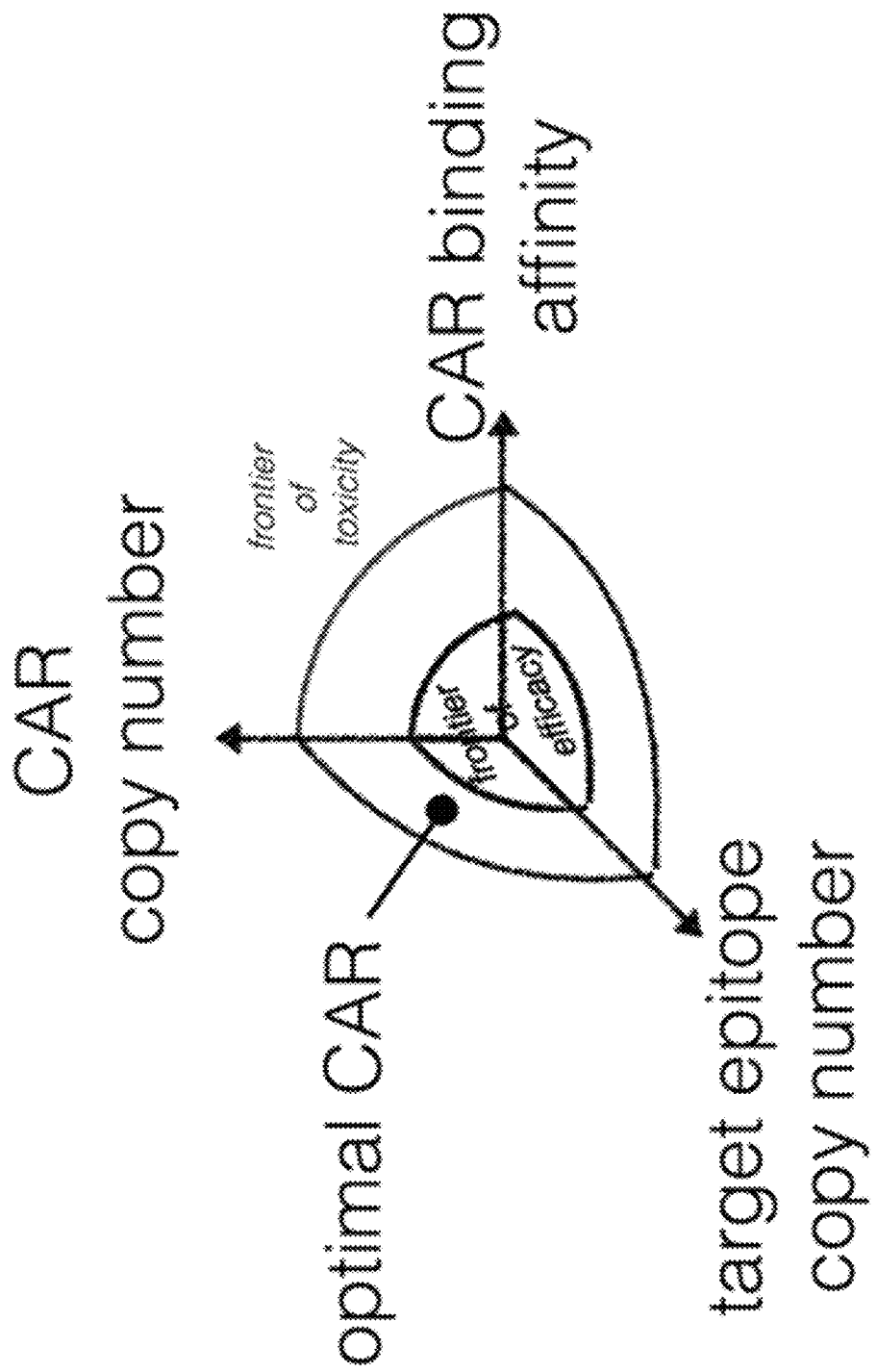
FIG. 1 shows a diagram for optimal CAR activity where the three variables are CAR copy number, target epitope copy number and CAR binding affinity.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. Numerical limitations given with respect to concentrations or levels of a substance are intended to be approximate, unless the context clearly dictates otherwise. Thus, where a concentration is indicated to be (for example) 10 μg, it is intended that the concentration be understood to be at least approximately or about 10 μg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, an "actuator element" is defined to be a domain that encodes the system control function of the RNA control device. The actuator domain can optionally encode the gene-regulatory function.

As used herein, an "antibody" is defined to be a protein functionally defined as a ligand-binding protein and structurally defined as comprising an amino acid sequence that is recognized by one of skill as being derived from the variable region of an immunoglobulin. An antibody can consist of one or more polypeptides substantially encoded by immunoglobulin genes, fragments of immunoglobulin genes, hybrid immunoglobulin genes (made by combining the genetic information from different animals), or synthetic immunoglobulin genes. The recognized, native, immunoglobulin genes include the kappa, lambda, alpha, gamma, delta, epsilon and mu constant region genes, as well as myriad immunoglobulin variable region genes and multiple D-segments and J-segments. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies exist as intact immunoglobulins, as a number of well characterized fragments produced by digestion with various peptidases, or as a variety of fragments made by recombinant DNA technology. Antibodies can derive from many different species (e.g., rabbit, sheep, camel, human, or rodent, such as mouse or rat), or can be synthetic. Antibodies can be chimeric, humanized, or humaneered. Antibodies can be monoclonal or polyclonal, multiple or single chained, fragments or intact immunoglobulins.

As used herein, an "antibody fragment" is defined to be at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either $V_L$ or $V_H$), camelid VHH domains, and multi-specific antibodies formed from antibody fragments. The term "scFv" is defined to be a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

As used herein, an "antigen" is defined to be a molecule that provokes an immune response. This immune response may involve either antibody production, or the activation of specific immunologically-competent cells, or both. The skilled artisan will understand that any macromolecule, including, but not limited to, virtually all proteins or peptides, including glycosylated polypeptides, phosphorylated polypeptides, and other post-translation modified polypeptides including polypeptides modified with lipids, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be synthesized or can be derived from a biological sample, or can be a macromolecule besides a polypeptide. Such a biological sample can include, but is not limited to a tissue sample, a tumor sample, a cell or a fluid with other biological components.

As used herein, the terms "Chimeric Antigen Receptor" and the term "CAR" are used interchangeably. As used herein, a "CAR" is defined to be a fusion protein comprising antigen recognition moieties and cell-activation elements.

As used herein, a "CAR T-cell" or "CAR T-lymphocyte" are used interchangeably, and are defined to be a T-cell containing the capability of producing CAR polypeptide, regardless of actual expression level. For example a cell that is capable of expressing a CAR is a T-cell containing nucleic acid sequences for the expression of the CAR in the cell.

As used herein, a "costimulatory element" or "costimulatory signaling domain" or "costimulatory polypeptide" are defined to be the intracellular portion of a costimulatory polypeptide. A costimulatory polypeptide can be represented in the following protein families: TNF receptor proteins, Immunoglobulin-like proteins, cytokine receptors, integrins, signaling lymphocytic activation molecules (SLAM proteins), and activating natural killer cell receptors. Examples of such polypeptides include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, MyD88, and the like.

As used herein, a "Cmax" is defined to mean the maximum concentration of a polypeptide produced by a cell after the cell is stimulated or activated to produce the polypeptide.

As used herein, a "cytokine $C_{max}$" is defined to mean the maximum concentration of cytokine produced by an immune cell after stimulation or activation to produce the cytokine.

As used herein, a "cytotoxic polypeptide $C_{max}$" is defined to mean the maximum concentration of cytotoxic polypeptide produced by an immune cell after stimulation or activation to produce the cytotoxic polypeptide.

As used herein, a "destabilizing element" or a "DE" or a "Degron" are used interchangeably, and are defined to be a polypeptide sequence that is inducibly resistant or susceptible to degradation in the cellular context by the addition or subtraction of a ligand, and which confers this stability modulation to a co-translated polypeptide to which it is fused in cis.

As used herein, an "effective amount" or "therapeutically effective amount" are used interchangeably, and defined to be an amount of a compound, formulation, material, or composition, as described herein effective to achieve a particular biological result.

As used herein, an "epitope" is defined to be the portion of an antigen capable of eliciting an immune response, or the portion of an antigen that binds to an antibody. Epitopes can be a protein sequence or subsequence that is recognized by an antibody.

As used herein, an "expression vector" and an "expression construct" are used interchangeably, and are both defined to be a plasmid, virus, or other nucleic acid designed for protein expression in a cell. The vector or construct is used to introduce a gene into a host cell whereby the vector will interact with polymerases in the cell to express the protein encoded in the vector/construct. The expression vector and/or expression construct may exist in the cell extrachromosomally or integrated into the chromosome. When integrated into the chromosome the nucleic acids comprising the expression vector or expression construct will be an expression vector or expression construct.

As used herein, an "extracellular element" is defined as the antigen binding or recognition element of a Chimeric Antigen Receptor.

As used herein, a "hematopoietic cell" is defined to be a cell that arises from a hematopoietic stem cell. This includes but is not limited to myeloid progenitor cells, lymphoid progenitor cells, megakaryocytes, erythrocytes, mast cells, myeloblasts, basophils, neutrophils, eosinophils, macrophages, thrombocytes, monocytes, natural killer cells, T lymphocytes, B lymphocytes and plasma cells.

As used herein, "heterologous" is defined to mean the nucleic acid and/or polypeptide are not homologous to the host cell. For example, a construct is heterologous to a host cell if it contains some homologous sequences arranged in a manner not found in the host cell and/or the construct contains some heterologous sequences not found in the host cell.

As used herein, an "intracellular element" is defined as the portion of a Chimeric Antigen Receptor that resides on the cytoplasmic side of the eukaryotic cell's cytoplasmic membrane, and transmits a signal into the eukaryotic cell. The "intracellular signaling element" is that portion of the intracellular element which transduces the effector function signal which directs the eukaryotic cell to perform a specialized function.

As used herein, "RNA destabilizing element" or "RDE" are used interchangeably and both are defined as a nucleic acid sequence in an RNA that is bound by proteins and which protein binding changes the stability and/or translation of the RNA. Examples of RDEs include Class I AU rich elements (ARE), Class II ARE, Class III ARE, U rich elements, GU rich elements, and stem-loop destabilizing elements (SLDE). Without wishing to be bound by theory, RDE's may also bind RNA stabilizing polypeptides like HuR.

As used herein, an "RNase III substrate" is defined to be an RNA sequence motif that is recognized and cleaved by an endoribonuclease of the RNase III family.

As used herein, an "RNAi substrate" is defined to be an RNA sequence that is bound and/or cleaved by a short interfering RNA (siRNA) complexed to an effector endonuclease of the Argonaute family.

As used herein, a "single chain antibody" (scFv) is defined as an immunoglobulin molecule with function in antigen-binding activities. An antibody in scFv (single chain fragment variable) format consists of variable regions of heavy ($V_H$) and light ($V_L$) chains, which are joined together by a flexible peptide linker.

As used herein, a "T-lymphocyte" or T-cell" is defined to be a hematopoietic cell that normally develops in the thymus. T-lymphocytes or T-cells include, but are not limited to, natural killer T cells, regulatory T cells, helper T cells, cytotoxic T cells, memory T cells, gamma delta T cells and mucosal invariant T cells.

As used herein, "transfected" or "transformed" or "transduced" are defined to be a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

As used herein, a "transmembrane element" is defined as the element between the extracellular element and the intracellular element. A portion of the transmembrane element exists within the cell membrane.

Destabilizing Elements

Destabilizing elements (DE) are stability-affecting polypeptides capable of interacting with a small-molecule ligand, the presence, absence, or amount of which ligand is used to modulate the stability of the DE-polypeptide of interest. The polypeptide of interest can be an immunomodulatory polypeptide. The polypeptide of interest can also be a CAR. Binding of ligand by a DE-CAR can reduce the degradation rate of the DE-CAR polypeptide in the eukaryotic cell. Binding of ligand by the DE-CAR can also increase the degradation rate of the DE-CAR in the eukaryotic cell.

Exemplary destabilizing elements or DEs are described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The ligand(s) for the DE can be selected for optimization of certain attributes for therapeutic attractiveness, for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

RNA Control Devices

The Ribonucleic acid (RNA) control devices disclosed herein can exhibit tunable regulation of gene expression, design modularity, and target specificity. The RNA control devices can act to rewire information flow through cellular networks and reprogram cellular behavior in response to changes in the cellular environment. In regulating polypeptide expression, the RNA control devices can serve as synthetic cellular sensors to monitor temporal and spatial fluctuations in the levels of diverse input molecules. RNA control devices represent powerful tools for constructing ligand-controlled gene regulatory systems tailored to modulate the expression of CAR, DE-CAR, and/or Side-CAR polypeptides of the invention in response to specific effector molecules enabling RNA regulation of target CAR, DE-CAR, and/or Side-CAR constructs in various living systems.

The RNA control devices disclosed herein comprise a regulatory element and a sensor element. The RNA control devices disclosed herein can comprise a single element with both a regulatory and sensory function. The RNA control devices disclosed herein can comprise a regulatory function and a sensory function. The RNA control devices disclosed herein can comprise a regulatory element, a sensor element, and an information transmission element (ITE) that functionally couples the regulatory element and the sensor element. The ITE can be based on, for example, a strand-displacement mechanism, an electrostatic interaction, a conformation change, or a steric effect. The sensing function of the RNA control device leads to a structural change in the RNA control device, leading to altered activity of the acting function. Some mechanisms whereby these structural changes can occur include steric effects, hydrophobicity driven effects (log p), electrostatically driven effects, nucleotide modification effects (such as methylation, pseudouradination, etc.), secondary ligand interaction effects and other effects. A strand-displacement mechanism can use competitive binding of two nucleic acid sequences (e.g., the competing strand and the RNA control device strand) to a general transmission region of the RNA control device (e.g., the base stem of the aptamer) to result in disruption or restoration of the regulatory element in response to ligand binding to the sensor element.

The RNA control device can comprise a sensor element and a regulatory element. The sensor element can be an RNA aptamer. The RNA control device can have more than one sensor element. In some aspects, the regulatory element can be a ribozyme. The ribozyme can be a hammerhead ribozyme. The ribozyme can also be a hairpin ribozyme, or a hepatitis delta virus (HDV) ribozyme, or a Varkud Satellite (VS) ribozyme, a glmS ribozyme, and/or other ribozymes known in the art.

The RNA control device or devices can be embedded within a DNA sequence. The RNA control device can be encoded for in messenger RNA. Multiple RNA control devices can be encoded in cis with a transgene-encoding mRNA. The multiple RNA control devices can be the same and/or a mixture of different RNA control devices repeated. The nucleic acid that is used to encode the RNA control device can be repeated. By including multiple RNA control devices, sensitivity and dose response may be tailored or optimized. The multiple RNA control devices can each be specific for a different ligand. This can mitigate unintentional expression due to endogenously produced ligands that interact with the sensor element.

RNA Control Devices: Sensor Elements

Exemplary sensor elements are described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes. Sensor elements can be derived from aptamers. An "aptamer" is a nucleic acid molecule, such as RNA or DNA that is capable of binding to a specific molecule with high affinity and specificity (Ellington et al., Nature 346, 818-22 (1990); and Tuerk et al., Science 249, 505-10 (1990), which are hereby incorporated by reference in their entirety for all purposes). For a review of aptamers that recognize small molecules, see Famulok, Science 9:324-9 (1999), which is hereby incorporated by reference in its entirety for all purposes.

Ligands for RNA Control Devices

RNA control devices can be controlled via the addition of exogenous ligand or synthesis (or addition) of endogenous ligands with desired binding properties, kinetics, bioavailability, etc., for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

RNA Control Devices: Regulatory Elements

The regulatory element can comprise a ribozyme, or an antisense nucleic acid, or an RNAi sequence or precursor that gives rise to a siRNA or miRNA, or a shRNA or precursor thereof, or an RNAse III substrate, or an alternative splicing element, or a transcription terminator, or a ribosome binding site, or an IRES, or a polyA site. Regulatory elements useful in the present invention are, for example, described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

RNA Destabilizing Elements

RNA destabilizing elements (RDE) are nucleic acids that affect or maintain the stability of an RNA molecule or the translation kinetics of an RNA molecule. Some RDEs are bound by polypeptides which destabilize (e.g., cleave) the RNA, or prevent translation, leading to loss of function for the RNA. Some RDE binding polypeptide stabilizes the RNA increasing the half-life of the RNA. RDEs can be used to control the expression of a transgene, e.g., a transgene encoding a chimeric antigen receptors. RDEs can be used with RNA control devices, DEs, and/or Side CARs to regulate the expression of a transgene. The RDEs can also be used to control expression of transgenes encoding polypeptides other than a CAR. Other transgenes may encode, for example, a cytokine, an antibody, a checkpoint inhibitor, a granzyme, an apoptosis inducer, complement, a cytotoxic small molecule, other cytotoxic compounds, a polypeptide for imaging, or other polypeptide that can have a desired effect. The RDE can control the delivery of a transgene payload. Examples of RDEs include, for example, AU rich elements, U rich elements, GU rich elements, and certain stem-loop elements. Exemplary RDEs are described in Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE can be a Class I AU rich element (dispersed AUUUA (SEQ ID NO:1) in U rich context), a Class II AU rich element (overlapping (AUUUA)$_n$), a Class III AU rich element (U-rich stretch), a stem-loop destabilizing element (SLDE), a cytokine 3' UTR (e.g., INF-γ, IL-2, T-cell receptor α chain, TNFα, IL-6, IL-8, GM-CSF, G-CSF etc.), and a sequence of AUUUAUUUAUUUA (SEQ ID NO: 2). Khabar, WIREs RNA 2016, doi: 10.1002/wrna.1368 (2016); Palanisamy et al, J. Dent. Res. 91:651-658 (2012), both of which are incorporated by reference in their entirety for all purposes. The RDE can also be a GU rich element comprised of one or more of, for example, UUGUU (SEQ ID NO: 3), UGGGGAU (SEQ ID NO: 4), or GUUUG (SEQ ID NO: 5). The RDE can be a U-rich element comprised of one or more of, for example, UUUGUUU (SEQ ID NO: 6), NNUUNNUUU (SEQ ID NO: 7), UUUAUUU (SEQ ID NO: 8), UUUGUUU (SEQ ID NO: 9), UUAGA (SEQ ID NO: 10), or AGUUU (SEQ ID NO: 11). In some aspects, multiple RDEs can be combined to make a regulatory unit, for example, multiple RDEs that have the same sequence can be arranged in a concatemer or can be arranged with intervening sequence in between some or all of the RDEs. The RDE sequence can be modified to increase or decrease the affinity of an RNA binding protein(s) for the RDE. For example, an AU rich RDE can be changed to alter the affinity of glyceraldehyde phosphate dehydrogenase (GAPDH) to the RDE. This change in affinity can alter the GAPDH-activation threshold for expression of a transgene regulated by the RDE to which GAPDH binds.

The disclosure assigns AU # designations to some RDEs and these RDEs can be referred to by the AU # or the gene name from which the RDE is derived. Some AU #s and the corresponding gene from which the RDE is derived include, for example, AU 1 (CD40LG), AU 2 (CSF2), AU 3 (CD247), AU 4 (CTLA4), AU 5 (EDN1), AU 6 (IL2RA), AU 7 (SLC2A1), AU 8 (TRAC), AU 9 (CD274), AU 10 (Myc), AU 11 (CD19), AU 12 (IL4), AU 13 (IL5), AU 14 (IL6), AU 15 (IL9), AU 16 (IL10), AU 17 (IL13), AU 18 (FOXP3), AU 19 (TMEM-219), AU 20 (TMEM-219snp), AU 21 (CCR7), AU 22 (SEM-A4D), AU 23 (CDC42-SE2), AU 24 (CD8), AU 27 (bGH), and AU 101 (IFNg).

The RDE can be from the 3' UTR of a gene encoding, for example, IL-1, IL-2, IL-3, IL-4, IL-6, IL-8, IL-10, GM-CSF, G-CSF, VEG F, PGE$_2$, COX-2, MMP (matrix metalloproteinases), bFGF, c-myc, c-fos, beta1-AR, PTH, interferon-gamma, MyoD, p21, Cyclin A, Cyclin B1, Cyclin D1, PAI-2, NOS HANOS, TNF-alpha, interferon-alpha, bc1-2, interferon-beta, c-jun, GLUT1, p53, Myogenin, NF-M, or GAP-43, lymphocyte antigen 96, SUPV3L1, SFtPA2, BLOC1S2, OR10A6, OR8D1, TRPT1, CIP29, EP400, PLE2, H3ST3A1, ZNF571, PPP1R14A, SPAG4L, OR10A6 and KIR3DL. Other RDEs are found in, for example, the 3'-UTRs from GLMN, AMY2B, AMY2A, AMY2A, AMY1A, TRIM33, TRIM33, TRIM33, CSRP1, PPP1R12B, KCNH1, Reticulon_4, MRPL30, Nav1.2, Tissue_factor_pathway_inhibitor, EEF1B2, CRYGB, ARMC9, RPL15, EAF2, MRPS22, MRPS22, COPB2, PDCD10, RE1-silencing_transcription_factor, Amphiregulin, AP1AR, TLR3, SKP2, Peptidylglycine_alpha-amidating_monooxygenase, TNFAIP8, Interleukin_9, PCDHA2, PCDHA12, Aldehyde_dehydrogenase_5_family,_member_A1, KCNQ5, COX7A2, Monocarboxylate_transporter_10, MLLT4, PHF10, PTPN12, MRNA_(guanine-N7-)-methyltransferase, WHSC1L1, Tricho-rhino-phalangeal_syndrome_Type_1, Interferon_alpha-1, ZCCHC6, Retinitis_pigmentosa_GTPase_regulator, MED14, CLCN5, DNA2L, OR52D1, NELL1, SLC22A25, SLC22A10, TRPC6, CACNA2D4, EPS8, CT2_(gene), Mitochondrial_ribosomal_protein_L42, TAOK3, NUPL1, Endothelin-receptor_type_B, Survival_of_motor_neuron_protein-interacting_protein_1, POLE2, Hepatic_lipase, TPSG1, TRAP1, RPS15A, HS3ST3A1, CROP_(gene), Apolipoprotein_H, GRB2, CEP76, VPS4B, Interleukin_28B, IZUMO1, FGF21, PPP1R15A, LIN7B, and CDC45-related_protein.

Still other RDEs can be found in, for example, the 3'UTRs of SCFD1, MAL2, KHSRP, IQCB1, CAMP_responsive_element_modulator, MFAP5, SBF2, FKBP2, PDCD10, UBE2V2, NDUFAB1, Coiled-Coil_Domain_Containing_Protein, ALG13, TPTE, Enaptin, Thymopoietin, Delta-like_1, C11orf30, Actinin_alpha_4, TMEM59, SP110, Dicer, TARDBP, IFNA17, IFNA16, IFNA14, ZMYM3, Interleukin_9,_type_I, OPN1SW, THSD1, ERGIC2, CAMK2B, WDR8, FXR1, Thymine-DNA_glycosylase, Parathyroid_hormone-related_protein, OSBPL3, Ran, GYPE, AKAP4, LOC642658, L2HGDH, AKAP1, Zinc_finger_protein_334, TC2N, FKBPL, GRB14, CXorf67, CXorf66, CEP76, Gastricsin, CEP70, CYP26A1, NAA35, Aryl_hydrocarbon_receptor_nuclear_translocator, KLC4, GPR112, LARP4, NOVA1, UBE2D3, ITGA6, GPR18, MGST_type_A, RE1-silencing_transcription_factor, ASPM, ZNF452, KIR2DS4, AHSA1, TMTC4, VSX1, P16, MRPL19, CCL20, TRPT1, Hepatic_lipase, PDLIM5, CCDC53, 'CCDC55, GAPVD1, HOXB2, KCNQ5, BRCC3, GTF2IRD1, CDK5RAP3, Transcription_factor_II_B, ZEB1, IRGM, SLC39A6, RHEB, PSIP1, RPS6KA5, Urokinase_receptor, GFM1, DNAJC7, Phosphoinositide-dependent_kinase-1, LMOD3, TTC35, RRP12, ATXN2, ACSM3, SOAT1, FGF8, HNRPH3, CTAGE5, POLG2, DYRK3, POLK, Cyclin-dependent_kinase_inhibitor_1C, CD137, Calmodulin_1, ZNF571, CNOT2, CRYZL1, SMC3, SMC4, SLC36A1, Decorin, HKR1, ERC1, S100A6, RIMS1, TMEM67, Mitochondrial_ribosomal_protein_L42, MECP2, RNF111, SULT1A1, MYLK3, TINAG, PRKAR1A, RGPDS, UBE2V1, SAR1B, SLC27A6, ZNF638, RAB33A, TRIOBP, MUCL1, CADPS2, MCF2L, TBCA, SLC17A3, LEO1, IFNA21, RUNX1T1, PRKD2, ATP11B, MORC2, RBM6, KLRD1, MED31, PPHLN1, HMGB2, DNA_repair_and_recombination_protein_RAD54-like, RBM9', ARL11, HuD, SPEF2, CBLL1, SLC38A1, 'Caspase_1', S100G, CA1_, CELA1, PTS, ITM2B, Natriuretic_peptide_precursor_C, TRPP3, IMPDH2, DPYS, CDCA3, EFCAB6, SLIT2, SIPA1L1, FIP1L1, ATP6V1B2, HSD17B4, HSD17B7, NDUFC1, CROP, CD48, APPBP1, CD44, CD46, Histone_deacetylase_2_type_XI, Interleukin_4, Tricho-rhino-phalangeal_syndrome_Type_1, SEC61G, TRIP12, PLEKHO1, SEC61B, ST6GALNAC1, CPVL, E2F7, UTP20, E2F5, PARD3, EXOC7, HEXB, Caspase_recruitment_domain-containing_protein_8, MBD4, PPP4C, Helicase, Phosducin, SPG11, CGGBP1, PSKH1, Cathepsin_S, orexin, IMMP2L, C2orf28, Laminin, EIF3S6, LRRC41_type_XII, Cathepsin_C, HPS6, ARAF, Zinc_finger_and_BTB_domain-containing_protein_16, Sex_hormone-binding_globulin, FBLN2, Suppressor_of_cytokine_signaling_1, TMEM126A, DOM3Z, TSFM POLQ-like, DYNLT3, CDH9, EAF2, MIPEP, NDUFA12, HDAC8, MKKS, FGG, IL36G, CDCA7, CRISPLD2, Olfactomedin-like_2b, MRPL32, MRPL33, AHI1, SMARCAL1, UTP14A, SSH2, Dystonin, Contactin_6, PPFIBP1, THOC1, CNOT1, RHCE, SLC41A3, SLC2A9, SNAP23, RFX3, GNG4, MRPL40, LSR, Angiogenin, TRIP4, VRK1, COUP-TFII, FOXP2, SNX2, Nucleoporin_85, RPL37A, RPL27A, SEC62, Calcium-activated_potassium_channel_subunit_alpha-1, SMARCE1, RPL17, CEP104, CEP290, VPS29, ANXA4, Zinc_finger_protein_737, DDX59, SAP30, NEK3, Exosome_component_9, Receptor_for_activated_C_kinase_1, Peptidylprolyl_isomerase_A, TINP1, CEACAM1, DISC1, LRRTM1, POP1_Lamin_B1, SREBP_cleavage-activating_protein, COX6C, TLR_1, ARID2, LACTB, MMS22L, UBE2E3, DAP3, ZNF23, SKP2, GPR113, IRF9 Ghrelin_O-acyltransferase, NEIL3, EEF1E1, COX17, ESD_, Dentin_sialophosphoprotein, HDAC9, RFC4, CYLD, RPLP0, EIF2B3, UGT2A1, FABP7, TRIP11, PLA2G4A, AKR1C3, INTS12, MYH1, ZBTB17, MYH4, NLRP2, MECOM, MYH8, Thermogenin_receptor_2, IFI16, THYN1, RAB17, ETFA, Cystic_fibrosis_transmembrane_conductance_regulator, F13B, RAB6A, ST8SIA1, SATB2, SATB1, HMG20B, UHRF1, CNOT3, Prostaglandin_EP2_receptor, FAM65B, Peroxisome_proliferator-activated_receptor_gamma, KvLQT2, GRIK5, SHOC2, Cortactin, FANCI, KIAA1199, Kynureninase, Decoy_receptor_1, NEU3, PHF10, Methyl-CpG-binding_domain_protein_2, RABGAP1, CEP55, SF3B1, MSH5, MSH6, CREB-binding_protein, LIMS1, SLC5A4, CCNB1IP1, RNF34, SORBS2, UIMC1, SOX5, YWHAZ, ICOSLG, NOP58, Zinc_finger_protein_679, PHKB, MED13, ABCB7, COQ9, C14orf104, Zinc_finger_protein 530, KLRC2, LSM8, NBR1, PRKCD, Long-chain-aldehyde_dehydrogenase, MTSS1, Somatostatin, Ubiquitin_carboxyl-terminal_hydrolase_L5, WDR72, FERMT3, Nuclear_ receptor_related-1_protein, Citrate_synthase, VPS11, KIZ, ZFYVE27, BCKDHB, Hypocretin, CACNG2, PTCH1, Carbonic_anhydrase_4, Nucleoporin_107, LDL_receptor, LEKTI, FBXO11, NDUFB3, FCHO2, CEP78, RAPGEF6, PPIL3, NIN, RAPGEF2, Growth_hormone_1, Growth_hormone_2, MNAT1, Nav1, MAP3K8, SUGT1, LAIR1, Hyaluronan-mediated_motility_receptor, MAP3K2, MPP2, TFB2M, CRB3, MPP5, CACNA1G, DLGAP2, INHBA, MAGI2, CIP29, SETDB1, Cytochrome_b5, TRPV2, Interleukin_1_receptor, HOXD8, TIMM10, ATXN2L, CLCN2, CREB1, TNIP1, CBLB, Factor_V, USP33, SON, RBBP8, SLC22A18, PTPN12, ADCY8, MYLK, KIF23, REXO2, BST1, TOP3B, COPB1, AXIN2, COPB2, TNRC6B, Guanidinoacetate_N-methyltransferase, Acyl-CoA_thioesterase_9, C4orf21, TSHB, FRS3, EPB41, Cyclin_T2, LAIR2, Nucleoporin_43, APLP2, TNFRSF19, Death-associated_protein 6, Epithelial_cell_adhesion_molecule, CLEC7A, Gephyrin, CLDND1, VPS37A, PCDHAC2, Bone_morphogenetic_protein_4, NVL, RBM33, RNF139, Sperm_associated_antigen_5, PLCB1, Glial_cell_line-derived_neurotrophic_factor, PARP4, PARP1, MAN2A1, Bone_morphogenetic_protein_1, PAX4, BCCIP, MMP7, Decoy_receptor_3, RAMP2, NCAPD3, LRRC37A, RWDD3, UBE2A, UBE2C, SLC3A1, MRPS22, CDC14A, ITSN1, POLE2, MYC-induced_nuclear_antigen, TMLHE, Glutamate_carboxypeptidase_II, GPR177, PPP2R5C, KIAA1333, RPP38, MYO1F, Farnesoid_X_receptor, Caldesmon, FBXO4, FBXO5, OPN1MW, PIGN, ARNTL2, BCAS3, C6orf58, PHTF2, SEC23A, NUFIP2, OAZ1, Osteoprotegerin, ANAPC4, ATP6V0A2, SPAM1, PSMA6, TAS2R30, RABEP1, DPM3, SLC6A15, RPS26, RPS27, RPS24, RPS20, RPS21, ARHGAP24, Catechol-O-methyl transferase, ERCC5, Transcription_initiation_protein_SPT3_homolog, OR1E1, ZNRF1, GMEB1, CCT2_GNAQ, Mucin_6, Mucin_4, LRP5, PDE9A, C2orf3, EZH2, Epidermal_growth_factor_receptor, TMTC2, PDE4A, EPH_receptor_A4, PPIB, DENND4A, ANTXR1, ANTXR2, Nucleoporin_88, SLCO1B3, COG8, RBMS1, MAP7, HIST2H2BE, AEBP2, DCLRE1A, RPL24, HNRPA2B1, RPL21, RPL23, MAPKAP1, NIPBL, ATG7, SERPINI2, GYLTL1B, ATP5G2, DIP2A, AMY2A, CEP63, TDRD7, PIEZO1, CLDN20, GRXCR1, PMEL, NIF3L1, MCC_, PCNX, TMBIM4, DUSP12, ZMYND8, GOSR1, Interferon_gamma_receptor_1, LDB3, PON3, C1D, ABCC8, COQ7, COQ6, AMELY, HAVCR1, PICALM, Sjogren_syndrome_antigen_B, PLK4, HBB, AKT1, PCDHGB7, C6orf10, UBR1, Retinoblastoma-like_protein_1, GRK6, WWC2, GRK4, INPP4B, SLC34A1, GOLGA2, MYCBP2, PTP4A2, NUCB2, MAGOH, RPP40, Alpha-2A_adrenergic_receptor, SPAG11B, Nucleoporin_205, COG1, Motile_sperm_domain_containing_3, KCNMB3, Motile_ sperm_domain_containing_1, KLHL7, KCNN2, TSPAN8, GPR21, Translocator_protein, HNRNPLL, ABHDS, CAB39L, Amphiregulin, GPR1, Interleukin 18, EIF4G3, Interleukin 15, CCDC80, CD2AP, NFS1, GRB2, ULBP2, Vascular_endothelial_growth_factor_C, RPS3, TLR8, BCL2-related_protein_A1, RHOT1, Collagen, Centromere_protein_E, STMN2, HESX1, RPL7, Kalirin, PCMT1, HLA-F, SUMO2, NOX3, EP400, DNM3, EED, NGLY1, NPRL2, PLAC1, Baculoviral_IAP_repeat-containing_protein_3, C7orf31, TUBA1C, HAUS3, IFNA10, MYST4, DCHS1, SIRT4, EFEMP1, ARPC2, MED30, IFT74, PAK1IP1, DYNC1LI2, POLR2B, POLR2H, KIF3A, PRDM16, PLSCR5, PEX5, Parathyroid_hormone_1_receptor, CDC23, RBPMS, MAST1, NRD1, BATS, BAT2, Dock11, GCSH, POF1B, USP15, POT1, MUTYH, CYP2E1, FAM122C, A1_polypeptide, Flavin_containing_monooxygenase_3, HPGD, LGALS13, MTHFD2L, Survival_motor_neuron_domain_containing_1, PSMA3, MRPS35, MHC_class_I_polypeptide-related_sequence_A, SGCE, REPS1, PPP1R12A, PPP1R12B, PABPC1, MAPK8, PDCD5, Phosphoglucomutase_3, Ubiquitin_C, GABPB2, Mitochondrial_translational_release_factor_1, PFDN4, NUB1, SLC13A3, ZFP36L1, Galectin-3, CC2D2A, GCA, Tissue_factor_pathway_inhibitor, UCKL1, ITFG3, SOS1, WWTR1, GPR84, HSPA14, GJC3, TCF7L1, Matrix_metallopeptidase_12, ISG20, LILRA3, Serum_albumin, Phosducin-like, RPS13, UTP6, HP1BP3, IL12A, HtrA_serine_peptidase_2, LATS1, BMF_, Thymosin_beta-4, B-cell_linker, BCL2L11, Coagulation_factor_XIII, BCL2L12, PRPF19, SFRS5, Interleukin_23_subunit_alpha, NRAP, 60S_ribosomal_protein_L14, C9orf64, Testin, VPS13A, DGKD, PTPRB, ATP5C1, KCNJ16, KARS, GTF2H2, AMBN, USP13, ADAMTSL1, TRO_, RTF1, ATP6V1C2, SSBP1, SNRPN_upstream_reading_frame_protein, RPS29, SNRPG, ABCC10, PTPRU, APPL1, TINF2, TMEM22, UNC45A, RPL30, PCDH7, Galactosamine-6_sulfatase, UPF3A, ACTL6A, ACTL6B, IL3RA, SDHB, Cathepsin_L2, TAS2R7, Cathepsin_L1, Pituitary_adenylate_cyclase-activating_peptide, RPN2, DYNLL1, KLK13, NDUFB3, PRPF8, SPINT2, AHSA1, Glutamate_carboxypeptidase_II, DRAP1, RNASE1, Olfactomedin-like 2b, VRK1, IKK2, ERGIC2, TAS2R16, CAMK2G, CAMK2B, Estrogen_receptor_beta, NADH_dehydrogenase, RPL19, NUCB2, KCTD13, ubiquinone, H2AFY, CEP290, PABPC1, HLA-F, DHX38, KIAA0922, MPHOSPH8, DDX59, MIB2_, ZBP1, C16orf84, UACA, C6orf142, MRPL39, Cyclin-dependent_kinase_7, Far_upstream_element-binding_protein_1, SGOL1, GTF2IRD1, ATG10, Dermcidin, EPS8L2, Decorin, Nicotinamide_phosphoribosyltransferase, CDC20, MYB, WNT5A, RBPJ, DEFB103A, RPS15A, ATP5H, RPS3, FABP1, SLC4A8, Serum_amyloid_P_component, ALAS1, MAPK1, PDCD5, SULT1A1, CHRNA3, ATXN10, MNAT1, ALG13, Ataxin_3, LRRC39, ADH7, Delta-sarcoglycan, TACC1, IFNA4, Thymic_stromal_lymphopoietin, LGTN, KIAA1333, MSH6, MYOT, RIPK5, BCL2L11, RPL27, Rnd1, Platelet_factor_4, HSD17B7, LSM8, CEP63, INTS8, CTNS, ASAHL, CELA3A, SMARCAL1, HEXB, SLC16A5, MAP3K12, FRMD6.

The RDE can be a Class I AU rich element that arises from the 3' UTR of a gene encoding, for example, c-myc, c-fos, beta1-AR, PTH, interferon-gamma, MyoD, p21, Cyclin A, Cyclin B1, Cyclin D1, PAI-2, or NOS HANOS. The RDE can also be a Class II AU rich element and arises from the 3' UTR of a gene encoding, for example, GM-CSF, TNF-alpha, interferon-alpha, COX-2, IL-2, IL-3, bc1-2, interferon-beta, or VEG-F. The RDE can be a Class III AU rich element that arises from the 3' UTR of a gene encoding, for example, c-jun, GLUT1, p53, hsp 70, Myogenin, NF-M, or GAP-43. Other RDEs may be obtained from the 3'-UTRs of a T-cell receptor subunit ($\alpha$, $\beta$, $\gamma$, or $\delta$ chains), cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3) and other checkpoint inhibitors. Still other RDEs may be obtained from the 3'-UTRs of senescence-associated secretory phenotype genes disclosed in Coppe et al., Ann. Rev. Pathol. 5:99-118 (2010), which is incorporated by reference in its entirety for all purposes (e.g., see Table 1).

The RDE can be bound by certain polypeptides including, for example, ARE poly(U) binding/degradation factor (AUF-1), tristetraprolin (TTP), human antigen-related protein (HuR), butyrate response factor 1 (BRF-1), butyrate response factor 2 (BRF-2), T-cell restricted intracellular antigen-1 (TIA-1), TIA-1 related protein (TIAR), CUG triplet repeat, RNA binding protein 1 (CUGBP-1), CUG triplet repeat, RNA binding protein 2 (CUGBP-2), human neuron specific RNA binding protein (Hel-N1, Hel-N2), RNA binding proteins HuA, HuB and HuC, KH-type splicing regulatory protein (KSRP), 3-methylglutaconyl-CoA hydratase (AUH), glyceraldehyde 3-phosphate dehydrogenase (GAPDH), heat shock protein 70 (Hsp70), heat shock protein 10 (Hsp10), heterogeneous nuclear ribonucleoprotein A1 (hnRNP A1), heterogeneous nuclear ribonucleoprotein A2 (hnRNP A2), heterogeneous nuclear ribonucleoprotein A3 (hnRNP A3), heterogeneous nuclear ribonucleoprotein C (hnRNP C), heterogeneous nuclear ribonucleoprotein L (hnRNP L), Bcl-2 AU-rich element RNA binding protein (TINO), Poly(A) Binding Protein Interacting Protein 2 (PAIP2), IRP1, pyruvate kinase, lactate dehydrogenase, enolase, and aldolase. The RDE binding protein also can be an enzyme involved in glycolysis or carbohydrate metabolism, such as, for example, Glyceraldehyde Phosphate Dehydrogenase (GAPDH), enolase (ENO1 or ENO3), Phosphoglycerate Kinase (PGK1), Triosephosphate Isomerase (TPI1), Aldolase A (ALDOA), Phosphoglycerate Mutase (PGAM1), Hexokinase (HK-2), or Lactate Dehydrogenase (LDH). The RDE binding protein can be an enzyme involved in the Pentose Phosphate Shunt, including for example, Transketolase (TKT) or Triosephate Isomerase (TPI1). Additional exemplary RNA binding proteins are those described in Castello et al., Molc. Cell 63:696-710 (2016); Kovarik et al., Cytokine 89:21-26 (2017); Ray et al., Nature 499:172-177 (2013); Castello et al., Cell 149:1393-1406 (2012); Vlasova et al., Molc. Cell. 29:263-270 (2008); Barreau et al., Nucl. Acids Res. vol 33, doi:10.1093/nar/gki1012 (2006); Meisner et al., ChemBioChem 5:1432-1447 (2004); Guhaniyogi et al., Gene 265:11-23 (2001), all of which are incorporated by reference in their entirety for all purposes.

The RDE binding protein can be TTP which can bind to RDEs including for example, one or more of UUAUUUAUU (SEQ ID NO: 12) and AUUUA (SEQ ID NO: 1), or KSRP which binds AU-rich RDEs, or Auf1 which binds RDEs including for example, one or more of UUGA (SEQ ID NO: 13), AGUUU (SEQ ID NO: 11), or GUUUG (SEQ ID NO: 5), or CELF-1 which binds RDEs including for example, one or more of UUGUU (SEQ ID NO: 3), or HuR which binds RDEs including for example, one or more of UUUAUUU (SEQ ID NO: 8), UUUAUUU (SEQ ID NO: 9), or UUUGUUU (SEQ ID NO: 6), or ESRP1 or ESRP2 which binds RDEs including for example, one or more of UGGGGAU (SEQ ID NO: 14), or ELAV which binds RDEs including for example, one or more of UUUGUUU (SEQ ID NO: 6). The RDE binding protein can be an enzyme involved in glycolysis, including for example, GAPDH which binds AU rich elements including for example, one or more of AUUUA (SEQ ID NO: 1) elements, or ENO3/ENO1 which binds RDEs including for example, one or more of CUGCUGCUG (SEQ ID NO: 15), or ALDOA which binds RDEs including for example, one or more of AUUGA (SEQ ID NO: 16).

In an aspect, the RDE can be combined with an RNA control device to make the regulation by the RDE ligand inducible. For example, an RDE can be operably linked to an RNA control device where ligand binding by the RNA control device activates the regulatory element (e.g., a ribozyme or riboswitch) which inhibits the RDE (e.g., a ribozyme cleaves the RDE so RDE binding proteins no longer bind, or the riboswitch alters secondary structure). This places transcripts with the RDE and RNA control device under two types of control from the RDE, first the RDE can regulate the transcript subject to binding of RDE binding proteins as governed by conditions in the cell, and second, the RDE control can be removed by inducing the RNA control device with ligand. When ligand is added, the RNA control device renders the RDE unavailable for binding and RDE regulation is removed. When ligand is removed, new transcripts that are transcribed can be under the control of the RDE (as the RNA control device will not be activated). Alternatively, an RDE can be operable linked to an RNA control device where ligand binding turns off the regulatory element (e.g., a ribozyme). In this example, the presence of ligand inhibits the RNA control device and transcripts can be regulated by the RDE. When ligand is removed, the RNA control device renders the RDE unavailable for binding to RDE binding proteins and RDE regulation of the transcript is removed. The RNA control device could also cleave a polynucleotide that binds to the RDE to form a structure (e.g., a helix) that inhibits RDE proteins from binding to the RDE. In this example, the RNA control device can cleave the inhibitory polynucleotide which then does not bind or is inhibited for binding to the RDE. This cleavage by the RNA control device can be stimulated by ligand binding or inhibited by ligand binding.

Different RDEs have different kinetic parameters such as, for example, different steady expression levels, different $T_{max}$ (time to maximal expression level), different $C_{max}$ (maximum expression level), different dynamic range (expression/basal expression), different AUC, different kinetics of induction (acceleration of expression rate and velocity of expression rate), amount of expression, baseline expression, maximal dynamic range ($DR_{max}$), time to $DR_{max}$, area under the curve (AUC), etc. In addition, these kinetic properties of the RDEs can be altered by making concatemers of the same RDE, or combining different RDEs into regulatory units. Placing RDEs under the control of an operably linked RNA control device can also alter the kinetic properties of the RDE, RDE concatemer, or RDE combinations. Also, small molecules and other molecules that affect the availability of RDE binding proteins for binding RDEs can be used to alter the kinetic response of an RDE, RDE concatemer, and/or RDE combinations. The kinetic response of RDEs, RDE concatemers, and/or RDE combinations can be changed using constructs that express competitive RDEs in a transcript. Such transcripts with one or more competing RDEs can compete for RDE binding proteins and so alter the regulation of the desired gene by an RDE, RDE concatemer, and/or RDE combination. These competitive RDE transcripts can bind to RDE binding proteins reducing the amount of RDE binding protein available for binding to the RDE, RDE concatemer, and/or RDE combination. Thus, RDEs, RDE concatemers, and/or RDE combinations can be selected and/or combined with other conditions (discussed above) to provide a desired kinetic response to the expression of a transgene.

Table 2 in Example 20 shows that different RDEs (e.g., AU elements) provided different kinetics of expression. For example, different RDEs (e.g., AU elements) reached maximal induction (maximal dynamic range also known as fold induction) at different time points. The RDEs AU 2 and AU 101 reached maximal dynamic range ($DR_{max}$) at day 1 and then the dynamic range (DR) decreased showing reduced expression compared to basal expression. The RDEs AU 5 and AU 21 had a $DR_{max}$ at day ¾ and this expression was maintained out to day 8. The RDEs AU 3, AU 7, AU 10, AU 20 and AU 23 had a $DR_{max}$ on day 6 and expression decreased on day 8. The RDEs AU 19 and AU 22 had $DR_{max}$ on day 8. The RDEs (e.g., AU elements) also had differences in the amount of expression covering a range of about 5500 fold comparing the expression of AU 7 to AU 10 (see Table 1). Thus, RDEs (AU elements) can be selected to provide maximal rates of expression at a desired time point and to provide a desired amount of polypeptide at that time point.

Some RNA binding proteins increase the rate of RNA degradation after binding to the RDE. Some RNA binding proteins decrease the rate of degradation of the RNA after binding to the RDE. More than one RNA binding protein binds can bind to an RDE. In some RDE regulatory units, more than one RNA binding protein binds to more than one RDE. Binding of one or more of the RNA binding proteins to the one or more RDEs can increase the degradation rate of the RNA. Binding of one or more of the RNA binding proteins can decrease the degradation rate of the RNA. RNA binding proteins that increase degradation may compete for binding to an RDE with RNA binding proteins that decrease degradation, so that the stability of the RNA is dependent of the relative binding of the two RNA binding proteins. Other proteins can bind to the RDE binding proteins and modulate the effect of the RNA binding protein on the RNA with the RDE. Binding of a protein to the RNA binding protein can increases RNA stability or decrease RNA stability. An RNA can have multiple RDEs that are bound by the proteins HuR and TTP. The HuR protein can stabilize the RNA and the TTP protein can destabilize the RNA. An RNA can have at least one RDE that interacts with the proteins KSRP, TTP and/or HuR. KSRP can destabilize the RNA and compete for binding with the HuR protein that can stabilize the RNA. The KSRP protein can bind to the RDE and destabilizes the RNA and the TTP protein can bind to KSRP and prevent degradation of the RNA. Different proteins may be bound to the same transcript and may have competing effects on degradation and stabilization rates. Different proteins may be bound to the same transcript and may have cooperative effects on degradation and stabilization rates. Different proteins may be bound to the same transcript at different times, conferring different effects on degradation and stabilization.

The RDE can be a Class II AU rich element, and the RNA binding protein can be GAPDH. The Class II AU rich element bound by GAPDH can be AUUUAUUUAUUUA (SEQ ID NO: 2). The Class II AU rich element and GADPH can be used to control the expression of a transgene, a CAR, Smart CAR, DE-CAR, Smart-DE-CAR, and/or Side-CAR. The Class II AU rich element and GADPH also can be used to effect the expression of a transgene, CAR, Smart CAR, DE-CAR, Smart-DE-CAR, and/or Side-CAR in a T-lymphocyte. The Class II AU rich element and GADPH can be used to effect the expression of a transgene, CAR, Smart CAR, DE-CAR, Smart-DE-CAR, and/or Side-CAR in a CD8+T-lymphocyte. The Class II AU rich element and GADPH can be used to effect the expression of a transgene, CAR, Smart CAR, DE-CAR, Smart-DE-CAR, and/or Side-CAR in a CD4+T-lymphocyte. The Class II AU rich element and GADPH can be used to effect the expression of a transgene, CAR, Smart CAR, DE-CAR, Smart-DE-CAR, and/or Side-CAR in a natural killer cell.

The RDE may have microRNA binding sites. The RDE can be engineered to remove one or more of these microRNA binding sites. The removal of the microRNA binding sites can increase the on expression from a construct with an RDE by at least 5, 10, 15, 20, 50 or 100 fold. The RDE with the microRNA sites can be an RDE that is bound by GAPDH. The removal of microRNA sites from the RDE bound by GAPDH can increase the on expression of a construct with the GAPDH sensitive RDE by at least 5-10 fold. This GAPDH control through the RDE can be used to deliver a payload at a target site. The GAPDH control can be tied to activation of the eukaryotic cell by a CAR that recognizes an antigen found preferentially at the target site.

The RDE can be the 3'-UTR of IL-2 or IFN-γ, and removal of micro-RNA sites can increase the rate of expression and/or the dynamic range of expression from a transgene RNA with the RDE. The RDE can be the 3'-UTR of IL-2 and the removed micro-RNA sites can be the MIR-186 sites which deletion increases the kinetics of expression and increases the dynamic range of expression by about 50-fold. The RDE also can be the 3'-UTR of IFN-γ and the microRNA sites removed can be the MIR-125 sites.

Chimeric Antigen Receptors

Chimeric antigen receptors (CARs) can be fused proteins comprising an extracellular antigen-binding/recognition element, a transmembrane element that anchors the receptor to the cell membrane and at least one intracellular element. These CAR elements are known in the art, for example as described in patent application US20140242701, which is incorporated by reference in its entirety for all purposes herein. The CAR can be a recombinant polypeptide expressed from a construct comprising at least an extracellular antigen binding element, a transmembrane element and an intracellular signaling element comprising a functional signaling element derived from a stimulatory molecule. The stimulatory molecule can be the zeta chain associated with the T cell receptor complex. The cytoplasmic signaling element may further comprise one or more functional signaling elements derived from at least one costimulatory molecule. The costimulatory molecule can be chosen from 4-1BB (i.e., CD137), CD27 and/or CD28. The CAR may be a chimeric fusion protein comprising an extracellular antigen recognition element, a transmembrane element and an intracellular signaling element comprising a functional signaling element derived from a stimulatory molecule. The CAR may comprise a chimeric fusion protein comprising an extracellular antigen recognition element, a transmembrane element and an intracellular signaling element comprising a functional signaling element derived from a co-stimulatory molecule and a functional signaling element derived from a stimulatory molecule. The CAR may be a chimeric fusion protein comprising an extracellular antigen recognition element, a transmembrane element and an intracellular signaling element comprising two functional signaling elements derived from one or more co-stimulatory molecule(s) and a functional signaling element derived from a stimulatory molecule. The CAR may comprise a chimeric fusion protein comprising an extracellular antigen recognition element, a transmembrane element and an intracellular signaling element comprising at least two functional signaling elements derived from one or more co-stimulatory molecule(s) and a functional signaling element derived from a stimulatory molecule. The CAR may comprise an optional leader sequence at the amino-terminus (N-term) of the CAR fusion protein. The CAR may further comprise a leader sequence at the N-terminus of the extracellular antigen recognition element, wherein the leader sequence is optionally cleaved from the antigen recognition element (e.g., a scFv) during cellular processing and localization of the CAR to the cellular membrane.

Chimeric Antigen Receptor—Extracellular Element

Exemplary extracellular elements useful in making CARs are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element(s) can be obtained from the repertoire of antibodies obtained from the immune cells of a subject that has become immune to a disease, such as for example, as described in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

The extracellular element may be obtained from any of the wide variety of extracellular elements or secreted proteins associated with ligand binding and/or signal transduction as described in U.S. patent application Ser. No. 15/070,352 filed on Mar. 15, 2016, U.S. patent application Ser. No. 15/369,132 filed Dec. 5, 2016, U.S. Pat. Nos. 5,359,046, 5,686,281 and 6,103,521, all of which are incorporated by reference in their entirety for all purposes.

Intracellular Element

The intracellular element can be a molecule that can transmit a signal into a cell when the extracellular element of the Smart CAR, DE-CAR, RDE-CAR, Smart-DE-CAR, Smart-RDE-CAR, DE-RDE-CAR, Smart-DE-RDE-CAR, and/or Side-CAR binds to (interacts with) an antigen. The intracellular signaling element can be generally responsible for activation of at least one of the normal effector functions of the immune cell in which the Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) has been introduced. The term "effector function" refers to a specialized function of a cell. Effector function of a T cell, for example, may be cytolytic activity or helper activity including the secretion of cytokines. Thus the term "intracellular signaling element" refers to the portion of a protein which transduces the effector function signal and directs the cell to perform a specialized function. While the entire intracellular signaling domain can be employed, in many cases the intracellular element or intracellular signaling element need not consist of the entire domain. To the extent that a truncated portion of the intracellular signaling domain is used, such truncated portion may be used as long as it transduces the effector function signal. The term intracellular signaling element is thus also meant to include any truncated portion of the intracellular signaling domain sufficient to transduce the effector function signal. Examples of intracellular signaling elements for use in the Smart CAR, DE-CAR, RDE-CAR, Smart-DE-CAR, Smart-RDE-CAR, DE-RDE-CAR, Smart-DE-RDE-CAR, and/or Side-CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

Intracellular elements and combinations of polypeptides useful with or as intracellular elements are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Transmembrane Element and Spacer Element

The Smart CAR, DE-CAR, RDE-CAR, Smart-DE-CAR, Smart-RDE-CAR, DE-RDE-CAR, Smart-DE-RDE-CAR, and/or Side-CAR may comprise a transmembrane element. The transmembrane element can be attached to the extracellular element of the Smart CAR, DE-CAR, RDE-CAR, Smart-DE-CAR, Smart-RDE-CAR, DE-RDE-CAR, Smart-DE-RDE-CAR, and/or Side-CAR. The transmembrane element can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). The transmembrane element can be associated with one of the other elements used in the Smart CAR, DE-CAR, RDE-CAR, Smart-DE-CAR, Smart-RDE-CAR, DE-RDE-CAR, Smart-DE-RDE-CAR, and/or Side-CAR. The transmembrane element can be selected or modified by amino acid substitution to avoid binding of such elements to the transmembrane elements of the same or different surface membrane proteins, e.g., to minimize interactions with other members of the receptor complex. The transmembrane element can be capable of homodimerization with another Smart CAR, DE-CAR, RDE-CAR, Smart-DE-CAR, Smart-RDE-CAR, DE-RDE-CAR, Smart-DE-RDE-CAR, and/or Side-CAR on the cell surface. The amino acid sequence of the transmembrane element may be modified or substituted so as to minimize interactions with the binding elements of the native binding partner present in the same cell.

Transmembrane elements useful in the present invention are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Chimeric Antigen Receptors: Side-CARs

The CARs, Smart CARs, DE-CARs, RDE-CARs, Smart-RDE-CARs, DE-RDE-CARs, Smart-DE-CARs, and/or Smart-DE-RDE-CARs can be comprised of at least two parts which associate to form a functional CAR or DE-CAR. The extracellular antigen binding element can be expressed as a separate part from the transmembrane element, optional spacer, and the intracellular element of a CAR. The separate extracellular binding element can be associated with the host cell membrane (through a means other than a transmembrane polypeptide). The intracellular element can be expressed as a separate part from the extracellular element, transmembrane element, and optionally the spacer. The extracellular element and intracellular element can be expressed separately and each can have a transmembrane element, and optionally a spacer. Each part of the CAR or DE-CAR can have an association element ("Side-CAR") for bringing the two parts together to form a functional CAR or DE-CAR.

Side CARs, selection of Side CARs, and their use with or without a tether are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Receptors

CARs may be used as the receptor with the cell and the RDE-transgene. CARs are described above. In addition to CARs, other receptors may be used to activate or otherwise change conditions in a cell so that a transgene under the control of an RDE is expressed. Receptors that recognize and respond to a chemical signal can be coupled to expression of the transgene through the RDE. For example, ion channel-linked (ionotropic) receptors, G protein-linked (metabotropic) receptors, and enzyme-linked receptors can be coupled to the expression of the transgene.

One class of receptor that can be coupled to transgene expression are immune receptors such as, for example, T-cell receptors, B-cell receptors (aka antigen receptor or immunoglobulin receptor), and innate immunity receptors.

T-cell receptors are heterodimers of two different polypeptide chains. In humans, most T cells have a T-cell receptor made of an alpha ($\alpha$) chain and a beta ($\beta$) chain have a T-cell receptor made of gamma and delta ($\gamma/\delta$) chains (encoded by TRG and TRD, respectively). Techniques and primers for amplifying nucleic acids encoding the T-cell receptor chains from lymphocytes are well known in the art and are described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. The TCR repertoires can be used as separate chains to form an antigen binding domain. The TCR repertoires can be converted to single chain antigen binding domains. Single chain TCRs can be made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/Aggen_David.pdf?sequence=1, all of which are incorporated by reference in their entirety for all purposes.

B-cell receptors include an immunoglobulin that is membrane bound, a signal transduction moiety, CD79, and an ITAM. Techniques and primers for amplifying nucleic acids encoding human antibody light and heavy chains are well-known in the art, and described in, for example, ProGen's Human IgG and IgM Library Primer Set, Catalog No. F2000; Andris-Widhopf et al., "Generation of Human Fab Antibody Libraries: PCR Amplification and Assembly of Light and Heavy Chain Coding Sequences," Cold Spring Harb. Protoc. 2011; Lim et al., Nat. Biotechnol. 31:108-117 (2010); Sun et al., World J. Microbiol. Biotechnol. 28:381-386 (2012); Coronella et al., Nucl. Acids. Res. 28:e85 (2000), all of which are incorporated by reference in their entirety for all purposes. Techniques and primers for amplifying nucleic acids encoding mouse antibody light and heavy chains are well-known in the art, and described in, for example, U.S. Pat. No. 8,143,007; Wang et al., BMC Bioinform. 7(Suppl):S9 (2006), both of which are incorporated by reference in their entirety for all purposes. The antibody repertoires can be used as separate chains in antigen binding domains, or converted to single chain antigen binding domains. Single chain antibodies can be made from nucleic acids encoding human light and heavy chains using techniques well-known in the art including, for example, those described in Pansri et al., BMC Biotechnol. 9:6 (2009); Peraldi-Roux, Methods Molc. Biol. 907:73-83 (2012), both of which are incorporated by reference in their entirety for all purposes. Single chain antibodies can be made from nucleic acids encoding mouse light and heavy chains using techniques well-known in the art including, for example, those described in Imai et al., Biol. Pharm. Bull. 29:1325-1330 (2006); Cheng et al., PLoS ONE 6:e27406 (2011), both of which are incorporated by reference in their entirety for all purposes.

Innate immunity receptors include, for example, the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

G-protein linked receptors also known as seven-transmembrane domain receptors are a large family of receptors that couple receptor binding of ligand to cellular responses through G proteins. These G-proteins are trimers of $\alpha$, $\beta$, and $\gamma$ subunits (known as G$\alpha$, G$\beta$, and G$\gamma$, respectively) which are active when bound to GTP and inactive when bound to GDP. When the receptor binds ligand it undergoes a conformational change and allosterically activates the G-protein to exchange GTP for bound GDP. After GTP binding the G-protein dissociates from the receptor to yield a G$\alpha$-GTP monomer and a G$\beta\gamma$ dimer. G-protein linked receptors have been grouped together into classes which include, for example, Rhodopsin-like receptors, secretin receptors, metabotropic glutamate/pheromone receptors, fungal mating pheromone receptors, cyclic AMP receptors, and frizzled/smoothened receptors. G-protein receptors are used in a wide variety of physiological processes including detection of electromagnetic radiation, gustatory sense (taste), sense of smell, neurotransmission, immune system regulation, growth, cell density sensing, etc.

Enzyme linked receptors also known as a catalytic receptor, is a transmembrane receptor, where the binding of an extracellular ligand causes enzymatic activity on the intracellular side. Enzyme linked receptors have two domains joined together by a transmembrane portion (or domain) of the polypeptide. The two terminal domains are an extracellular ligand binding domain and an intracellular domain that has a catalytic function. There are multiple families of enzyme linked receptors including, for example, the Erb receptor family, the glial cell-derived neurotrophic factor receptor family, the natriuretic peptide receptor family, the trk neurotrophin receptor family, and the toll-like receptor family.

Ion channel linked receptors also known as ligand-gated ion channels are receptors that allow ions such as, for example, $Na^+$, $K^+$, $Ca^{2+}$ and $Cl^-$ to pass through the membrane in response to the binding of a ligand to the receptor. There are multiple families of ligand-gated ion channels including, for example, cationic cys-loop receptors, anionic cys-loop receptors, ionotropic glutamate receptors (AMPA receptors, NMDA receptors), GABA receptors, 5-HT receptors, ATP-gated channels, and $PIP_2$-gated channels.

Eukaryotic Cells

Various eukaryotic cells can be used as the eukaryotic cell of the invention. The eukaryotic cells can be animal cells. The eukaryotic cells can be mammalian cells, such as mouse, rat, rabbit, hamster, porcine, bovine, feline, or canine. The mammalian cells can be cells of primates, including but not limited to, monkeys, chimpanzees, gorillas, and humans. The mammalians cells can be mouse cells, as mice routinely function as a model for other mammals, most particularly for humans (see, e.g., Hanna, J. et al., *Science* 318:1920-23, 2007; Holtzman, D. M. et al., *J Clin Invest.* 103(6):R15-R21, 1999; Warren, R. S. et al., *J Clin Invest.* 95: 1789-1797, 1995; each publication is incorporated by reference in its entirety for all purposes). Animal cells include, for example, fibroblasts, epithelial cells (e.g., renal, mammary, prostate, lung), keratinocytes, hepatocytes, adipocytes, endothelial cells, and hematopoietic cells. The animal cells can be adult cells (e.g., terminally differentiated, dividing or non-dividing) or embryonic cells (e.g., blastocyst cells, etc.) or stem cells. The eukaryotic cell also can be a cell line derived from an animal or other source.

The eukaryotic cells can be stem cells. A variety of stem cells types are known in the art and can be used as the eukaryotic cell, including for example, embryonic stem cells, inducible pluripotent stem cells, hematopoietic stem cells, neural stem cells, epidermal neural crest stem cells, mammary stem cells, intestinal stem cells, mesenchymal stem cells, olfactory adult stem cells, testicular cells, and progenitor cells (e.g., neural, angioblast, osteoblast, chondroblast, pancreatic, epidermal, etc.). The stem cells can be stem cell lines derived from cells taken from a subject.

The eukaryotic cell can be a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells of the invention. The eukaryotic cell can be derived from any of these circulating eukaryotic cells. Transgenes may be used with any of these circulating cells or eukaryotic cells derived from the circulating cells. The eukaryotic cell can be a T-cell or T-cell precursor or progenitor cell. The eukaryotic cell can be a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. The eukaryotic cell can be a natural killer cell, or a precursor or progenitor cell to the natural killer cell. The eukaryotic cell can be a B-cell, or a B-cell precursor or progenitor cell. The eukaryotic cell can be a neutrophil or a neutrophil precursor or progenitor cell. The eukaryotic cell can be a megakaryocyte or a precursor or progenitor cell to the megakaryocyte. The eukaryotic cell can be a macrophage or a precursor or progenitor cell to a macrophage.

The eukaryotic cells can be plant cells. The plant cells can be cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, *eucalyptus*, hemp, lettuce, lentil, maize, mango, melon, oat, *papaya*, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), *Arabidopsis*, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

The eukaryotic cells also can be algal, including but not limited to algae of the genera *Chlorella, Chlamydomonas, Scenedesmus, Isochrysis, Dunaliella, Tetraselmis, Nannochloropsis,* or *Prototheca*. The eukaryotic cells can be fungi cells, including, but not limited to, fungi of the genera *Saccharomyces, Klyuveromyces, Candida, Pichia, Debaryomyces, Hansenula, Yarrowia, Zygosaccharomyces,* or *Schizosaccharomyces*.

The eukaryotic cells can be obtained from a subject. The subject may be any living organisms. The cells can be derived from cells obtained from a subject. Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. Any number of T cell lines available in the art also may be used. T-cells can be obtained from a unit of blood collected from a subject using any number of techniques known to the skilled artisan, such as Ficoll separation. Cells from the circulating blood of an individual can be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells can be washed with phosphate buffered saline (PBS). In an alternative aspect, the wash solution lacks calcium and may lack magnesium or may lack many if not all divalent cations. Initial activation steps in the absence of calcium can lead to magnified activation.

Enrichment of a T cell population by negative selection can be accomplished with a combination of antibodies directed to surface markers unique to the negatively selected cells. Cells can be enriched by cell sorting and/or selection via negative magnetic immunoadherence or flow cytometry using a cocktail of monoclonal antibodies directed to cell surface markers present on the cells. For example, to enrich for CD4+ cells, a monoclonal antibody cocktail typically includes antibodies to CD14, CD20, CD11b, CD16, HLA-DR, and CD8. It may be desirable to enrich for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005, each of which is incorporated by reference in its entirety for all purposes.

NK cells may be expanded in the presence of a myeloid cell line that has been genetically modified to express membrane bound IL-15 and 4-1BB ligand (CD137L). A cell line modified in this way which does not have MEW class I and II molecules is highly susceptible to NK cell lysis and activates NK cells. For example, K562 myeloid cells can be transduced with a chimeric protein construct consisting of human IL-15 mature peptide fused to the signal peptide and transmembrane domain of human CD8a and GFP. Transduced cells can then be single-cell cloned by limiting dilution and a clone with the highest GFP expression and surface IL-15 selected. This clone can then be transduced with human CD137L, creating a K562-mb15-137L cell line. To preferentially expand NK cells, peripheral blood mononuclear cell cultures containing NK cells are cultured with a K562-mb15-137L cell line in the presence of 10 IU/mL of IL-2 for a period of time sufficient to activate and enrich for a population of NK cells. This period can range from 2 to 20 days, preferably about 5 days. Expanded NK cells may then be transduced with the anti-CD19-BB-ζ chimeric receptor.

Nucleic Acids

Also described in this disclosure are nucleic acids that encode, at least in part, the individual peptides, polypeptides, proteins, and RNA control devices described herein. The nucleic acids may be natural, synthetic or a combination thereof. The nucleic acids of the invention may be RNA, mRNA, DNA or cDNA.

The nucleic acids of the invention also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. An exemplary selection scheme can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a Smart CAR, DE-CAR, RDE-CAR, Smart-DE-CAR, Smart-RDE-CAR, DE-RDE-CAR, Smart-DE-RDE-CAR, and/or Side-CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention is not limited to the use of constitutive promoters.

Inducible or repressible promoters are also contemplated for use in this disclosure. Examples of inducible promoters include, but are not limited to a Nuclear Factor of Activated T-cell inducible promoter (NFAT), a metallothionein promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Macian et al., Oncogene 20:2476-2489 (2001); Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes.

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

The expression vector may be a bi-cistronic construct or multiple cistronic construct. The two cistrons may be oriented in opposite directions with the control regions for the cistrons located in between the two cistrons. When the construct has more than two cistrons, the cistrons may be arranged in two groups with the two groups oriented in opposite directions for transcription. Exemplary bicistronic constructs are described in Amendola et al., Nat. Biotechnol. 23:108-116 (2005), which is incorporated by reference in its entirety for all purposes. The control region for one cistron may be capable of high transcription activity and the other may have low transcriptional activity under conditions of use. One or both control regions may be inducible. Examples of high transcription activity control regions include, for example, MND, EF1-alpha, PGK1, CMV, ubiquitin C, SV40 early promoter, tetracycline-responsive element promoter, cell-specific promoters, human beat-actin promoter, and CBG (chicken beta-globin), optionally including the CMV early enhancer. Examples of low transcription activity control regions include, for example, TRE3G (commercially sold by Clontech, a tetracycline-responsive element promoter with mutations that reduce basal expression), T-REx™ (commercially sold by Thermo-Fisher), and a minimal TATA promoter (Kiran et al., Plant Physiol. 142:364-376 (2006), which is incorporated by reference in its entirety for all purposes), HSP68, and a minimal CMV promoter. Examples of inducible control regions include, for example, NFAT control regions (Macian et al, Oncogene 20:2476-2489 (2001)), and the inducible control regions described above.

The bi-cistronic construct may encode a CAR and a polypeptide that is a payload (or makes a payload) to be delivered at a target site. Exemplary payloads are described above and below. The nucleic acid encoding the CAR can be operably linked to a strong promoter, a weak promoter, and/or an inducible promoter, and optionally, operably linked to a RNA control device, DE, RDE, or combination of the foregoing. The CAR can be encoded by nucleic acids in a Side-CAR format. The nucleic acid encoding the polypeptide can be operably linked to a strong promoter, a weak promoter, and/or an inducible promoter. The nucleic acid encoding the polypeptide that is a payload (or makes the payload) can be under the control of an RDE. The RDE may be one that responds to the activation state of the cell through, for example, glycolytic enzymes such as, for example, glyceraldehyde phosphate dehydrogenase (GAPDH), enolase (ENO1 or ENO3), phosphoglycerate kinase (PGK1), triose phosphate isomerase (TPI1), aldolase A (ALDOA), or phosphoglycerate mutase (PGAM1). The RDE may also be bound and regulated by other energy metabolism enzymes such as, for example, transketolase (TKT), malate dehydrogenase (MDH2), succinyl CoA Synthetase (SUGLG1), ATP citrate lyase (ACLY), or isocitrate dehydrogenase (IDH1/2). The host cell can express a CAR that binds to its antigen at a target site in a subject. This binding of antigen at the target site activates the cell causing the cell to increase glycolysis which induces expression of the nucleic acid encoding the polypeptide under the control of the RDE (bound by glycolytic or other energy metabolism enzymes).

The multicistronic constructs can have three or more cistrons with each having control regions (optionally inducible) and RDEs operably linked to some or all of the transgenes. These cassettes may be organized into two groups that are transcribed in opposite directions on the construct. Two or more transgenes can be transcribed from the same control region and the two or more transgenes may have IRES (internal ribosome entry site) sequences operably linked to the downstream transgenes. Alternatively, the two or more transgenes are operably linked together by 2A elements as described in Plasmids 101: Multicistronic Vectors found at blog.addgene.org/plasmids-101-multicistrnic-vectors. Commonly used 2A sequences include, for example, EGRGSLLTCGDVEENPGP (T2A) (SEQ ID NO: 17), ATNFSLLKQAGDVEENPGP (P2A) (SEQ ID NO: 18); QCTNYALLKLAGDVESNPGP (E2A) (SEQ ID NO: 19); and VKQTLNFDLLKLAGDVESNPGP (F2A) (SEQ ID NO: 20) all of which can optionally include the sequence GSG at the amino terminal end. This allows multiple transgenes to be transcribed onto a single transcript that is regulated by a 3'-UTR with an RDE (or multiple RDEs).

The bicistronic/multicistronic vector can increase the overall expression of the two or more cistrons (versus introducing the cistrons on separate constructs). The bicistronic/multicistronic construct can be derived from a lentivirus vector. The bicistronic/multicistronic construct can encode a CAR and a polypeptide(s) that is encoded on a transgene(s) (e.g., a payload), and the bicistronic construct may increase expression of the polypeptide encoded by the transgene(s) when the cell is activated by the CAR.

It may be desirable to modify polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, *Gene* 8:81-97, 1979; Roberts et al., *Nature* 328:731-734, 1987, which is incorporated by reference in its entirety for all purposes). The recombinant nucleic acids encoding the polypeptides of the invention can be modified to provide preferred codons which enhance translation of the nucleic acid in a selected organism.

The polynucleotides can also include polynucleotides including nucleotide sequences that are substantially equivalent to other polynucleotides described herein. Polynucleotides can have at least about 80%, more typically at least about 90%, and even more typically at least about 95%, sequence identity to another polynucleotide. The nucleic acids also provide the complement of the polynucleotides including a nucleotide sequence that has at least about 80%, more typically at least about 90%, and even more typically at least about 95%, sequence identity to a polynucleotide encoding a polypeptide recited herein. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., Angew Chem Intl Ed. 28:716-34, 1989 (which is incorporated by reference in its entirety for all purposes), may also be used to prepare such nucleic acids.

Amino acid "substitutions" for creating variants are preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Also disclosed herein are nucleic acids encoding Smart CAR, DE-CAR, RDE-CAR, Smart-DE-CAR, Smart-RDE-CAR, DE-RDE-CAR, Smart-DE-RDE-CAR, and/or Side-CARs. The nucleic acid encoding the Smart CAR, DE-CAR, RDE-CAR, Smart-DE-CAR, Smart-RDE-CAR, DE-RDE-CAR, Smart-DE-RDE-CAR, and/or Side-CAR can be easily prepared from an amino acid sequence of the specified CAR combined with the sequence of the RNA control device by a conventional method. A base sequence encoding an amino acid sequence can be obtained from the aforementioned NCBI RefSeq IDs or accession numbers of GenBenk for an amino acid sequence of each element, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acids can be linked to another nucleic acid so as to be expressed under control of a suitable promoter. The nucleic acid can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

When the nucleic acid is introduced into a cell ex vivo, the nucleic acid of may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful. Particularly, a composition in a form suitable for administration to a living body which contains the nucleic acid of the present invention carried by a suitable vector is suitable for in vivo gene therapy.

Introducing Nucleic Acids into Eukaryotic Cells

A process for producing a cell expressing the Smart CAR, DE-CAR, RDE-CAR, Smart-DE-CAR, Smart-RDE-CAR, DE-RDE-CAR, Smart-DE-RDE-CAR, Side-CAR, and/or a transgene operably linked to an RDE(s) includes a step of introducing the nucleic acid encoding a Smart CAR, DE-CAR, RDE-CAR, Smart-DE-CAR, Smart-RDE-CAR, DE-RDE-CAR, Smart-DE-RDE-CAR, Side-CAR, and/or transgene-RDE described herein into a eukaryotic cell. This step can be carried out ex vivo. Exemplary methods for introducing nucleic acids to eukaryotic cells are described, for example, in U.S. patent application Ser. No. 15/070,352 filed on Mar. 15, 2016, and U.S. patent application Ser. No. 15/369,132 filed Dec. 5, 2016, both of which are incorporated by reference in their entirety for all purposes.

Virus Payloads

Viruses can be used to deliver transgenes to target cells. Viruses can carry nucleic acid constructs (e.g., transfer plasmids) as payloads and so deliver to a target cell desired nucleic acids for modification of the target cell genotype and/or phenotype (transiently or stably). In many of these transduction applications, the nucleic acid carried by the virus does not include all of the viral genome, and often includes the viral genome signals needed for packaging the nucleic acid construct into the virus without most or all of the rest of the viral genome. For example, lentiviral helper plasmid and transfer plasmids systems for transduction of target cells are available from addgene. Other helper and transfer plasmid systems are commercially available form a number of sources (e.g., Clontech/Takara).

When used as a payload, synthesis of viral capsids, packaging of payload nucleic acids, and release of virus with payload nucleic acids can be restricted to the target site by timing the expression of the virus genes for replication and coat proteins to binding of ligand by a receptor at the target site. Such control can be achieved using RDEs that induce expression when the cell undergoes a change in metabolic state (e.g., activation of glycolysis after receptor binding to target). This RDE control can regulate expression of master switch factors for expression of the virus genes. For example, a transcription regulatory factor can be placed under the control of a suitable RDE, and the viral genes for replication, coat proteins etc can be placed under the control of this transcription factor. When the host cell binds to ligand at the target site through an appropriate receptor (e.g., a CAR) this activates the cell, induces expression of the transcription factor with the appropriate RDE leading to expression of the viral replication proteins, coat proteins, etc.

In helper constructs, the viral genes can be placed under the control of a variety of transcription factors. Such transcription factors can include, for example, ICP4, VP16 or VP64 from Herpes Simplex, or VP30 from Ebola or TFEB from Adeno associated virus. The transcription factor can be a viral master switch such as, for example, the E1A protein of adenovirus, or Pax5 of Epstein Barr Virus, or NS1 from influenza, NS5A from Hepatitis C. Alternatively, the Cap and Rep functions of the virus can be placed under the control of an appropriate RDE so that the replication proteins and coat proteins are under the control of an RDE that provides expression upon a change in the energy state of the cell (e.g., activation of glycolysis after receptor binding of a ligand).

Similarly, viral payload constructs can include the viral Rep, Cap and other virus genes. In these examples, an RDE can be used to regulate expression of a master switch transcription factor for the virus (analogous to the helper constructs). This can tie synthesis of virus with the desired nucleic acid to binding of ligand by a host cell receptor at the target site. Examples of virus master-switch transcription factors include E4F from adenovirus or BZLF1 from Epstein Barr virus.

Viruses have also emerged as a highly viable treatment platform for many types of cancer through oncolytic virotherapy ("OVT") (Howells et al., Oncolytic Viruses-interaction of Virus and Tumor Cells in the Battle to Eliminate Cancer, Front. Oncol., (2017); https://doi.org/10.3389/fonc.2017.00195). In these applications, viruses can effectively replicate within a host, specifically target and lyse target cells and induce robust, long lasting target cell specific immunity. Oncolytic virus ("OV") can include viruses that are either naturally tumor-selective or can be modified to specifically target and eliminate tumor cells. Additionally, these OVs can be selectively modified by a variety of methods, which include, for example, insertions, which can include immune stimulators like IL-12 or a kill switch, and deletions, which can include thymidine kinase ("TK"), of specific genes with the aim of improving their efficacy and safety profiles.

OVs can be utilized that retain naturally occurring oncolytic properties or those that have been engineered to specifically lyse a particular tumor cell. A variety of methods can be employed to improve the specificity of OVs, for example, taking advantage of pathways which are upregulated in tumor cells and not healthy cells and by engineering a virus that relies on such a pathway for successful infection thereby rendering the virus incapable of infecting healthy tissue. A significant advantage of OVT lies in the fact that while viral infection can directly lyse tumor cells, the resultant immune response will be generated not only to viral antigens but also to tumor cell antigens. In addition, there are a multitude of anti-cancer genes that can be incorporated into OVs in this way in order to maximize the efficacy of the virus and improve the anti-tumor response generated.

There are various ways in which different viruses are able to infect cells. Some viruses, like vaccinia virus ("VV") or Newcastle disease virus ("NDV") lack specific receptors for attachment and enter cells via endocytosis (which favors cells active metabolism, e.g., cancer cells). Other viruses have a specific receptor that they use to enter host cells; for example, adenoviruses are able to bind CAR (a 46 kD protein that also mediates infection by group B coxsackieviruses), and certain RGD binding integrins, or cluster of differentiation 46 (CD46). Measles can also use CD46 for entry, whereas herpes simplex virus (HSV) uses nectin or herpesvirus entry mediator (Dörig et al., The human CD46 molecule is a receptor for measles virus (Edmonston strain), Cell, 75(2):295-305 (1993); Badrinath et al., Viruses as nanomedicine for cancer, Int J Nanomedicine, 11:4835-4847 (2016)).

There are a variety of methods wherein viruses can be targeted to target cells. These methods include, for example, exploitation of certain pathways that are aberrantly expressed in target cells to ensure engineered viruses are only capable of productive infection in cells which have abnormal levels of certain genes. Viral coat proteins can also be manipulated to ensure viral infection only occurs in cells with certain receptors, e.g., receptors found predominantly on target cells. For example, the coat/envelope proteins can be engineered to include single chain antibodies specific for desired target cell associated antigens using antibody display technologies for viruses (e.g., analogous to phage display). Alternatively, other ligands can be fused with coat/envelope proteins that will interact with target associated receptors.

Viral coat proteins, i.e., capsids, can be modified to specifically direct viral infection to target cells. There are various ways to achieve this, for example, covering the viral surface with a polymer to "cloak" the viral receptor(s) and addition of a molecule, e.g., epidermal growth factor ("EGF") to the virus that binds with target cells, e.g., some tumor cells have upregulated EGF receptor ("EGFR") expression (Morrison et al., Virotherapy of ovarian cancer with polymer-cloaked adenovirus retargeted to the epidermal growth factor receptor, Mol Ther., 16(2):244-251 (2008)). This particular approach not only reduces the broad tropism conferred by the existing viral receptor, but also replaces this with a target cell specific receptor to direct virus infection to target cells, leaving healthy tissue unharmed.

An additional approach for targeting viruses uses antibodies to target viruses to target cells. As an example of this strategy, Watkins et al., showed that fusions between antibodies and viral coat proteins can target EGFR. This facilitates targeting of virus to cells expressing upregulated EGFR (Watkins et al., The 'adenobody' approach to viral targeting: specific and enhanced adenoviral gene delivery, Gene Ther., 4(10):1004-1012 (1997). This antibody focused approach can also use antibody fragments such as scFv integrated into the viral capsid proteins (analogous to phage display of antibodies). For example, HSV type-1 ("HSV-1") relies on various glycoproteins for entry into cells and one of these glycoproteins ("gD") is responsible for interaction with the viral entry receptors. An scFv targeting EGFR can be fused to this glycoprotein, and the virus is then able to use EGFR as an entry receptor which improves selectivity for target cell (Conner et al., A strategy for systemic delivery of the oncolytic herpes virus HSV1716: redirected tropism by antibody-binding sites incorporated on the virion surface as a glycoprotein D fusion protein, Gene Ther., 15(24):1579-1592 (2008)). In general, the antibody fused with or otherwise associated with the coat proteins can be targeted to any target cell associated antigen. For example, anti-CD19 and/or anti-CD20 antibodies can target the viral payload to B-cells (healthy or diseased) and anti-CD90, anti-CD117 and/or anti-CD133 antibodies can target the viral payload to cancer stem cells, including myeloma stem cells.

As recited above, differential expression of certain surface markers on target cells compared with healthy cells can be exploited to produce target cell selective viruses. For example, genes can be deleted resulting in a virus that can only successfully infect certain tumor types which overexpress MEK (Veerapong et al., Systemic delivery of (gamma1)34.5-deleted herpes simplex virus-1 selectively targets and treats distant human xenograft tumors that express high MEK activity, Cancer Res., 67(17):8301-8306

(2007)). This approach can also be used with HSV whereby genes can be deleted to produce a virus which preferentially replicates in tumor cells, which unlike healthy cells, tend to have a constitutively activated Ras pathway (Fu et al., A mutant type 2 herpes simplex virus deleted for the protein kinase domain of the ICP10 gene is a potent oncolytic virus, Mol Ther., 13(5):882-90 (2006)). As this virus initiates apoptosis in infected and bystander cells and preferentially infects tumor cells, it can be used as oncolytic agent with this deletion (Fu et al., An HSV-2-based oncolytic virus deleted in the PK domain of the ICP10 gene is a potent inducer of apoptotic death in tumor cells, Gene Ther., 14(16):1218-1225 (2007)). In addition, antibodies are other molecules can be engineered into the coat proteins (e.g., viral capsid proteins) to direct the virus to cells expressing the surface marker (or expressing higher amounts of the surface marker).

Viruses may be modified with specific gene deletions to target the virus to target cells and inhibit infectivity in healthy cells. An example of this strategy is thymidine kinase ("TK") deletion from VV. As the wild-type virus typically encodes this kinase it is able to replicate in healthy cells, however, when the gene is deleted the virus can no longer replicate efficiently in healthy cells. As tumor cells produce higher levels of TK, even though the gene is deleted, the virus is still able to replicate in these cells (McCart et al., Systemic cancer therapy with a tumor-selective vaccinia virus mutant lacking thymidine kinase and vaccinia growth factor genes, Cancer Res., 61(24):8751-8757 (2001); Hughes et al., Lister strain vaccinia virus with thymidine kinase gene deletion is a tractable platform for development of a new generation of oncolytic virus, Gene Ther., 22(6):476-484 (2015)).

In another approach, it is possible to delete genes in the viral genome to produce a desired effect in the target cell. The deleted genes can reside in the viral construct delivered by the virus or in the target cell. For example, the virus genome could be engineered to delete genes for coat proteins or other factors so that the virus can lyse the target cell (or otherwise kill the target cell) but does not create new viral particles for infection of other cells. In target cell deletions, the construct delivered by the virus includes nucleic acids that cause a deletion in the genome of the target cell. Such approaches can be used, for example, to delete apoptosis-inhibiting genes.

Gene deletion strategies can also be used to improve the efficiency of virus delivery systems that are designed to deliver viruses to target cells without interference from the host immune system. Viruses can be delivered within host cells (e.g., mesenchymal stem cells), which provide shelter from immune attack and subvert the problem of clearance of virus (by neutralizing antibodies) before they reach their target cells. This method has been improved in Ad by modification of the virus to make it more infective in MSC and more efficient at killing tumor cells.

Promoters that are activated more highly in target cells versus non-target cells can be used to control expression of a transgene carried by the virus so that the transgene is preferentially expressed in target cells (Zhang et al., Complete eradication of hepatomas using an oncolytic adenovirus containing AFP promoter controlling E1A and an E1B deletion to drive IL-24 expression, Cancer Gene Ther., 19(9):619-629 (2012); Cheng et al., Virotherapy targeting cyclin E overexpression in tumors with adenovirus-enhanced cancer-selective promoter, J Mol Med (Berl), 93(2):211-223 (2015)).

OV and other viruses can also be engineered to carry a marker (e.g., a coat protein fusion) that will enhance immune reaction and clearance of the virus after a subject has been exposed to virus therapy. The marker can be available on virus particles, infected cells, or both. Such markers can recruit the subject's immune system to clear virus and/or infected cells after a certain period of treatment by the virus. The OV can also be engineered to have a kill-switch that can be activated to stop viral infection in the subject treated with the OV payload. For example, the OV could be engineered to place certain functions (e.g., viral coat proteins) under the control of an inducible promoter that can be turned off by a desired signal. Additionally, or separately, the OV could be engineered to encode a heterologous protein under inducible control that will display a protein on the surface of the infected cell that directs the immune system to destroy the cell (e.g., a heterologous MHA that is incompatible with the host). Alternatively, the OV can be engineered to turn off coat protein expression so the infected cell stop producing new virus.

Many different viruses or virus helper systems can be used to make the viral payload. The viral payload can be an entire virus, an engineered virus, or a construct with transgene(s), desired control elements, and viral packing sequences. Viruses that can be used (or viral helper systems can be based on) AAV, VV, Adenovirus, HSV, NDV, lentivirus, retroviruses, MV, Reovirus, etc.

Multiple AAV serotypes have been identified as a promising means for gene delivery as they possess important advantages over other vectors. Specifically, they do not exhibit pathogenicity in humans and may also provide significantly longer transgene expression. (Berns et al., The Cryptic Life Style of Adeno-associated Virus, Bioassays, (17):237-245 (1995); Zincarelli et al., Analysis of AAV Serotypes 1-9 Mediated Gene Expression and Tropism in Mice after Systemic Injection, Mol. Thera., 16(6):1073-1080 (2008) doi: 10.1038/mt.2008.76.).

VV is a naturally oncolytic virus that has a natural tropism for tumor cells due to its sensitivity to type I interferon (Wang et al., Disruption of Erk-dependent type I interferon induction breaks the myxoma virus species barrier, Nat Immunol., 5(12):1266-1274 (2004)). It is a double-stranded DNA virus of the Poxviridae family. There are many different strains of the virus and of these, for example, Lister, Wyeth and Western Reserve strains. VV is a very promising cell killing agent (Al Yaghchi et al., Vaccinia virus, a promising new therapeutic agent for pancreatic cancer, Immunotherapy, 7(12):1249-1258 (2015)), for many reasons including its very short life cycle (around 8 h) and its ability to replicate in hypoxic conditions (Hiley et al., Lister strain vaccinia virus, a potential therapeutic vector targeting hypoxic tumors, Gene Ther., 17(2):281-287 (2010)). Moreover, it does not have a specific receptor and viral fusion with the plasma membrane facilitates entry (Chung et al., A27L protein mediates vaccinia virus interaction with cell surface heparan sulfate, J Virol., 72(2):1577-1585 (1998)), which makes it a potential candidate for treatment of all target cell types. Furthermore, VV does not depend on the host cell for mRNA transcription and its entire life cycle takes place in the cytoplasm, eliminating the risk of genomic integration (Broyles S S, Vaccinia virus transcription, J Gen Virol., 84(Pt 9):2293-2303 (2003)). Modifications which can improve the anti-tumor efficacy of VV include, for example, the addition of IL-10, which improves the oncolytic activity of VV through dampening of anti-viral immunity (prolonging viral infection) without reducing anti-tumor immunity (Chard et al., A vaccinia virus armed with interleukin-10 is a promising therapeutic agent for treatment of murine pancreatic cancer, Clin Cancer Res, 21(2):405-416 (2015)).

Ad received regulatory approval by the State Food and Drug Administration in China in 2005 (Garber K., China approves world's first oncolytic virus therapy for cancer treatment, J Natl Cancer Inst, 98(5):298-300 (2006)). It is a non-enveloped, double-stranded DNA virus of the Adenoviridae family. Multiple strains of Ad exist and include, for example, Ad5. Ad5 is has been widely studied and there exist a multitude of various modifications in the art, which have been shown to improve efficacy. For example, the combination of p53 addition to suppress tumor growth with GM-CSF addition to induce the apoptotic pathway elicits a synergistic effect which is effective in combating hepatocellular cancer stem cells (Lv et al., 11R-P53 and GM-CSF expressing oncolytic adenovirus target cancer stem cells with enhanced synergistic activity, J Cancer, 8(2):199-206 (2017)).

Ad can be improved by the incorporation of a short-hairpin RNA, which functions to downregulate Dicer (an endoribonuclease which has a role in processing virus-associated RNA). Downregulation of this protein inhibits the destruction of viral RNA and allows Ad to replicate efficiently and therefore improves the efficacy of this OV (Machitani et al., Enhanced oncolytic activities of the telomerase-specific replication-competent adenovirus expressing short-hairpin RNA against Dicer, Mol Cancer Ther., 16(1):251-9 (2017)).

Gene silencing techniques can also be used to downregulate gene expression in target cells. For example, EphA3 expression can be downregulated by siRNA targeting this gene expressed from a virus. This approach can be used to downregulate the expression of other desired genes in a target cell.

A T-cell immune response to oncolytic virus infection can be efficacious in killing target cells as cytotoxic T-cells kill the virus infected target cells (e.g., Li et al., The efficacy of oncolytic adenovirus is mediated by T-cell responses against virus and tumor in Syrian hamster model, Clin Cancer Res, 23(1):239-249 (2017)).

In addition, the virus payloads described herein can include any of the other payloads encoded by a transgene that are described herein. Including for example, checkpoint inhibitors, granzymes, apoptosis inducing polypeptides, etc.

The present invention further provides a therapeutic approach wherein two or more antigenically distinct viruses are employed. One method, for example, is achieved by employing VV after first administering adenoviral therapy. In this approach, it has been observed that the increased efficacy was dependent on T-cell activity (Tysome et al., A novel therapeutic regimen to eradicate established solid tumors with an effective induction of tumor-specific immunity, Clin Cancer Res., 18(24):6679-6689 (2012)). Another example includes, sequential delivery of oncolytic Ad and Newcastle Disease Virus ("NDV"), which are both engineered to express an immuno-stimulatory cytokine which leads to significant anti-tumor responses even though when administered alone, each virus demonstrates limited efficacy against tumors (Nistal-Villan et al., Enhanced therapeutic effect using sequential administration of antigenically distinct oncolytic viruses expressing oncostatin M in a Syrian hamster orthotopic pancreatic cancer model, Mol Cancer, 14:210 (2015)).

The oncolytic potential of viruses can be increased by combining oncolytic therapy with induction of the autophagy pathway. The autophagy pathway is involved in viral antigen presentation and therefore its upregulation can increase presentation of virally delivered tumor-associated antigens ("TAAs") at the cell surface to induce a more potent anti-tumor immune response than with antigen delivery alone (Klein et al., Critical role of autophagy in the processing of adenovirus capsid-incorporated cancer-specific antigens, PLoS One, 11(4):e0153814 (2016)).

A potential barrier to viral spread in tumor masses is the interstitial matrix (including extracellular DNA). Viruses can be modified to encode proteins which will degrade the interstitial matrix along with expression of DNase I to degrade extracellular DNA, therefore allowing more efficient spread of viruses throughout target cell masses (Tedcastle et al., Actin-resistant DNAse I expression from oncolytic adenovirus enadenotucirev enhances its intratumoral spread and reduces tumor growth, Mol Ther., 24(4):796-804 (2016)).

Viruses can also be exploited as carriers for drugs using more than one method. For example, it has recently been reported that electrostatic attraction between viral capsid and the drug molecules themselves was an efficient way to deliver anti-cancer drugs which would then act synergistically with the oncolytic adenoviral therapy (Garofalo et al., Oncolytic adenovirus loaded with L-carnosine as novel strategy to enhance the antitumor activity, Mol Cancer Ther., 15(4):651-60 (2016)).

Herpes simplex virus type-1 a double-stranded DNA virus belonging to the Herpesviridae family can also be used. HSV-1 was the first virus wherein the TK gene mutation was engineered. In 1991, Martuza et al. demonstrated that human glioblastoma cells can be destroyed by HSV-1 carrying a mutation in the TK region and this was observed in cell culture as well as in nude mice (Martuza et al., Experimental therapy of human glioma by means of a genetically engineered virus mutant, Science, 252(5007):854-856 (1991)). Much effort has since been put into making HSV more active against tumor cells and safer for normal cells culminating in the approval of Talimogene laherparepvec ("T-Vec"), an engineered HSV-1 for the treatment of melanoma in 2015 (Coffin R., Interview with Robert Coffin, inventor of T-Vec: The first oncolytic immunotherapy approved for the treatment of cancer, Immunotherapy, 8(2):103-106 (2016)). T-Vec has two viral gene deletions (one in the γ34.5 gene and one in the α47 gene) and it has the human GM-CSF gene inserted in place of the deleted γ34.5 gene. The function of γ34.5 is to prevent infected cells from switching off protein synthesis upon viral infection.

Another HSV that can be used as a payload is G47Δ, a third generation HSV-1 with three different mutations. NV1020 virus is an HSV that can be used as a payload. NV1020 virus based on the R7020 construct developed by Meignier et al. (Meignier et al., In vivo behavior of genetically engineered herpes simplex viruses R7017 and R7020: construction and evaluation in rodents, J Infect Dis, 158(3): 602-14 (1988)). NV1020 virus has deletions in the ICP0 and ICP4 gene regions and has only one copy of the γ34.5 gene. Moreover, the α4 promoter, which controls TK expression, has been inserted, making the virus sensitive to common drugs, for example, acyclovir.

The Newcastle Disease Virus (NDV) can also be used a viral payload. It has been found that NDV can effectively kill a variety of tumor cell types and that this activity occurs by induction of immunogenic cell death which in turn leads to adaptive anti-tumor immunity (Koks et al., Newcastle disease virotherapy induces long-term survival and tumor-specific immune memory in orthotopic glioma through the induction of immunogenic cell death, Int J Cancer, 136(5): E313-25 (2015)). Certain strains of NDV can induce apoptosis in target cells (Lazar et al., The oncolytic activity of Newcastle disease virus NDV-HUJ on chemoresistant primary melanoma cells is dependent on the proapoptotic activity of the inhibitor of apoptosis protein livin, J Virol, 84(1):639-46 (2010)), and that the apoptosis pathway stimulated in infected tumor cells is p53-independent and perhaps triggered by endoplasmic stress (Fabian et al., p53-independent endoplasmic reticulum stress-mediated cytotoxicity of a Newcastle disease virus strain in tumor cell lines, J Virol, 81(6):2817-30 (2007)). It has been discovered that apoptosis of infected cells occurs predominantly via the intrinsic mitochondrial pathway and is caspase dependent (Elankumaran et al., Newcastle disease virus exerts oncolysis by both intrinsic and extrinsic caspase-dependent pathways of cell death, J Virol, 80(15):7522-34 (2006)). This induction of apoptosis results in tumor cell death.

As well as arming viruses with immune stimulators, other therapeutic genes can increase anti-target cell effects of viral therapies. For example, NDV engineered to encode TNF receptor Fas shows greater oncolytic effect as Fas is responsible for increased apoptosis of infected cells via both the intrinsic and extrinsic apoptosis pathways, thereby increasing cell death and in turn anti-tumor efficacy (Cuadrado-Castano et al., Enhancement of the proapoptotic properties of Newcastle disease virus promotes tumor remission in syngeneic murine cancer models, Mol Cancer Ther, 14(5): 1247-58 (2015)). NDV's naturally oncolytic properties can also be augmented by arming the virus with GM-CSF (Janke et al., Recombinant Newcastle disease virus (NDV) with inserted gene coding for GM-CSF as a new vector for cancer immunogene therapy, Gene Ther, 14(23):1639-49 (2007)).

Retroviruses are yet another virus useful as a payload. A method has been developed whereby retroviral particles, which retain their replicative ability, can be delivered and selectively replicate only in cells which are undergoing proliferation (e.g., tumor cells) and are compromised in their ability to trigger innate immune responses. The ability of these particles to integrate into the host genome and replicate without causing lysis of the cell makes them efficient and long-lasting producers of the therapeutic proteins they are delivering without the consequences of productive viral infection (Logg et al., Retroviral replicating vectors in cancer, Methods Enzymol, 507:199-228 (2012)).

As is the case for traditional oncolytic viral therapy, this method can be designed using a variety of retroviruses and with the addition of various therapeutic genes. For example, suicide genes which trigger cell death can be delivered to tumor cells via particles from various leukemia viruses (Lu et al., Replicating retroviral vectors for oncolytic virotherapy of experimental hepatocellular carcinoma, Oncol Rep, 28(1):21-26 (2012)).

As well as delivering therapeutic genes, replicating retroviral vectors can also be used to enhance the response to anti-target cell drug therapy. For example, delivery of an activator of a therapeutic drug by replication competent retroviral vector resulted in significant anti-tumor effect and prolonged survival time in a murine model of malignant mesothelioma (Kawasaki et al., Replication-competent retrovirus vector-mediated prodrug activator gene therapy in experimental models of human malignant mesothelioma, Cancer Gene Ther, 18(8):571-8 (2011)). These vectors can also be delivered within a "gutted" Ad genome and the outcome of this combination is improved transfer efficiency of the retroviral genome into the tumor tissue and therefore increased production of the therapeutic gene (Kubo et al., Adenovirus-retrovirus hybrid vectors achieve highly enhanced tumor transduction and antitumor efficacy in vivo, Mol Ther., 19(1):76-82 (2011)).

MV is another useful virus payload. MV is a single-stranded, negative sense enveloped RNA virus of the Paramyxoviridae family. There are a number of receptors that can be utilized by MV to successfully infect cells including CD150, CD46, and nectin-4. Of these, CD46 has been attributed to increased specificity of MV to certain target cells that express increased levels of this receptor compared with healthy cells. This increased expression leads to increased levels of cell lysis upon infection of target cells compared with healthy tissue (Anderson et al., High CD46 receptor density determines preferential killing of tumor cells by oncolytic measles virus, Cancer Res, 64(14): 4919-26 (2004)). Selectivity can also be increased by engineering a MV which is blinded to its usual receptors and redirected to recognize specific target cell markers as target antigens (Nakamura et al., Rescue and propagation of fully retargeted oncolytic measles viruses, Nat Biotechnol, 23(2): 209-14 (2005)). Another method of increasing MV selectivity is to engineer miRNA sensitive viruses which can only successfully infect cells in which certain miRNAs are down-regulated (e.g., cancer cells). For example, a virus has been developed which shows sensitivity to three host miRNAs through insertion of specific miRNA target sites into the viral genome, rendering the virus incapable of infecting healthy cells which express one or more of these miRNAs but still able to infect specific cancer cells which have downregulated levels of these miRNAs (Baertsch et al., MicroRNA-mediated multi-tissue de-targeting of oncolytic measles virus, Cancer Gene Ther., 21(9):373-80 (2014)).

Reovirus is a double-stranded, non-enveloped RNA virus of the Reoviridae family and is considered a naturally occurring OV. Reoviruses are thought to selectively infect tumor cells because their oncolytic functions depend on the activation of the Ras pathway (Strong et al., The molecular basis of viral oncolysis: usurpation of the Ras signaling pathway by reovirus, EMBO J, 17(12):3351-62 (1998)), which tends to be upregulated in transformed cells. Two additional viruses that can be payloads include, for example, coxsackievirus and echovirus.

Manipulating Target Cell Genes to Increase Virus Targeting

Target cell genes can play a role in the targeting of virus to target cells. For example, it was discovered by Cuddington et al., that a certain virus (Bovine herpesvirus-1) are better able to infect cells which have increased levels of certain proteins (e.g., KRAS tumor cells) (Cuddington et al., Permissiveness of human cancer cells to oncolytic bovine herpesvirus 1 is mediated in part by KRAS activity, J Virol, 88(12):6885-95 (2014)).

The aberrant expression of components of the Raf/MEK/ERK pathway in target cells can also have an effect on the regulation of Ad receptor and therefore levels of viral infectivity. As this pathway tends to be upregulated in some potential target cells (e.g., tumor cells) compared with healthy cells, it can have a significant effect on viral therapy.

As well as mutations, regulation of certain genes using microRNA can also be used to enhance viral specificity for target cells. For example, using an miRNA which is down-regulated in target cells (such as let-7a in tumor cells) to control expression of an essential viral gene in VV (such as B5R which increases both pathogenicity and oncolytic activity) results in a virus that can only express sufficient amounts of B5R in cells which have low levels of let-7a expression, i.e., tumor cells (Hikichi et al., MicroRNA regulation of glycoprotein B5R in oncolytic vaccinia virus reduces viral pathogenicity without impairing its antitumor efficacy, Mol Ther., 19(6):1107-15 (2011)).

Another gene found in tumor cells that can influence virus therapy is VEGF. It has been demonstrated that VEGF-A increases VV internalization and in turn replication levels (Hiley et al., Vascular endothelial growth factor A promotes vaccinia virus entry into host cells via activation of the Akt pathway, J Virol., 87(5):2781-90 (2013)). Therefore, VV can take advantage of the increased expression of VEGF by target cells to increase delivery of therapeutic genes which in turn increases the efficacy and potency of the treatment.

In addition to this, it has been discovered that the increase in VEGF expression upon infection with VV leads to upregulation of PRD1-BF1 (a transcription repressor), which increases sensitivity of tumor vascular endothelial cells to infection with vaccinia via repression of type-1 interferon anti-viral signaling. This increase in viral tropism allows the OV to spread through the tumor more efficiently and therefore increases the efficacy of this oncolytic therapy (Arulanandam et al., VEGF-mediated induction of PRD1-BF1/Blimp1 expression sensitizes tumor vasculature to oncolytic virus infection, Cancer Cell, 28(2):210-24 (2015)). This natural repression of interferon signaling highlights the potential of using interferon inhibitors to increase the efficacy of oncolytic viral therapy (Stewart et al., Inhibitors of the interferon response enhance virus replication in vitro, PLoS One, 9(11):e112014 (2014)).

It has also been demonstrated that a properly functioning host interferon response pathway is a critical factor in measles infection of malignant pleural mesothelioma. It was seen that in cell lines, there is a correlation between sensitivity of cells to measles infection and an inability of the cell to elicit a full interferon response in the presence of MV (Achard et al., Sensitivity of human pleural mesothelioma to oncolytic measles virus depends on defects of the type I interferon response, Oncotarget, 6(42):44892-904 (2015)). It has also been demonstrated that VV infection is greatly increased through downregulation of c-Jun NH2-terminal kinase (JNK). Inhibition of the JNK signaling cascade leads to lower levels of double-stranded RNA dependent protein kinase, which in turn permits increased replication of VV genomes (Hu et al., JNK-deficiency enhanced oncolytic vaccinia virus replication and blocked activation of double-stranded RNA-dependent protein kinase, Cancer Gene Ther., 15(9):616-24 (2008)).

Another gene found in tumor cells (CEACAM6), also has an effect on oncolytic viral therapy. This tumor-associated gene has various functions, which include, for example, a role in promotion of tumor adhesion and invasion among other factors (Duxbury et al., Overexpression of CEACAM6 promotes insulin-like growth factor I-induced pancreatic adenocarcinoma cellular invasiveness, Oncogene, 23(34): 5834-42 (2004)).

Eukaryotic Cells Expressing the Smart CAR, DE-CAR, RDE-CAR, Smart-DE-CAR, Smart-RDE-CAR, DE-RDE-CAR, Smart-DE-RDE-CAR, and/or Side-CAR The cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be cells in which a nucleic acid encoding a Smart CAR, DE-CAR, RDE-CAR, Smart-DE-CAR, Smart-RDE-CAR, DE-RDE-CAR, Smart-DE-RDE-CAR, Side-CAR, and/or transgene-RDE is introduced and expressed.

Eukaryotic cells can bind to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell can be activated. The activation of the eukaryotic cell expressing the Smart CAR, DE-CAR, RDE-CAR, Smart-DE-CAR, Smart-RDE-CAR, DE-RDE-CAR, Smart-DE-RDE-CAR, and/or Side-CAR can be varied depending on the kind of a eukaryotic cell and the intracellular element of the Smart CAR, DE-CAR, RDE-CAR, Smart-DE-CAR, Smart-RDE-CAR, DE-RDE-CAR, Smart-DE-RDE-CAR, and/or Side-CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and/or a macrophage.

A eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be used as a therapeutic agent to treat a disease. This therapeutic agent can comprise the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE as an active ingredient, and may further comprise a suitable excipient. Examples of the excipient include pharmaceutically acceptable excipients for the composition. The disease against which the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE is administered is not particularly limited as long as the disease shows sensitivity to the eukaryotic cell. Examples of diseases of the invention include a cancer (blood cancer (leukemia), solid tumor (ovarian cancer) etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. An autoimmune disease (e.g., pemphigus vulgaris, lupus erythematosus, rheumatoid arthritis) can be treated with a eukaryotic cell expressing a Smart CAR, DE-CAR, RDE-CAR, Smart-DE-CAR, Smart-RDE-CAR, DE-RDE-CAR, Smart-DE-RDE-CAR, Side-CAR, and/or transgene-RDE that binds to the immune proteins that cause the autoimmune disease. For example, the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can target cells that make an antibody which causes the autoimmune disease. The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE could target T-lymphocytes which cause the autoimmune disease.

Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be used as a therapeutic agent to treat an allergy. Such therapeutic agents can comprise the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE as an active ingredient, and may further comprise a suitable excipient. Examples of the excipient include pharmaceutically acceptable excipients for the composition. Examples of allergies that can be treated with the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE include, for example, allergies to pollen, animal dander, peanuts, other nuts, milk products, gluten, eggs, seafood, shellfish, and soy. The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can target cells that make an antibody which causes the allergic reaction against, for example, pollen, animal dander, peanuts, other nuts, milk products, gluten, eggs, seafood, shellfish, and soy. The targeted cells can be one or more of B-cells, memory B-cells, plasma cells, pre-B-cells, and progenitor B-cells. The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can target T-lymphocytes which cause the allergic reaction against, for example, pollen, animal dander, peanuts, other nuts, milk products, gluten, eggs, seafood, shellfish, and soy. The Smart CAR, DE-CAR, RDE-CAR, Smart-DE-CAR, Smart-RDE-CAR, DE-RDE-CAR, Smart-DE-RDE-CAR, Side-CAR, and/or transgene-RDE can bind to the idiotypic determinant of the antibody or T-cell receptor.

The eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be administered for treatment of a disease or condition. These eukaryotic cells can be utilized for prevention of an infectious disease after bone marrow transplantation or exposure to radiation, donor lymphocyte transfusion for the purpose of remission of recurrent leukemia, and the like. The therapeutic agent comprising the eukaryotic cell expressing the Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be an active ingredient and can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

The Smart CAR, DE-CAR, RDE-CAR, Smart-DE-CAR, Smart-RDE-CAR, DE-RDE-CAR, Smart-DE-RDE-CAR, Side-CAR, and/or transgene-RDE can be used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. The RNA control device can be used with an armored CAR, DE-CAR, and/or Side-CAR polypeptide in a T-lymphocyte.

Pharmaceutical Compositions

Pharmaceutical compositions of the present invention may comprise a Smart CAR, DE-CAR, RDE-CAR, Smart-DE-CAR, Smart-RDE-CAR, DE-RDE-CAR, Smart-DE-RDE-CAR, Side-CAR, and/or transgene-RDE expressing cell, e.g., a plurality of Smart CAR, DE-CAR, RDE-CAR, Smart-DE-CAR, Smart-RDE-CAR, DE-RDE-CAR, Smart-DE-RDE-CAR, Side-CAR, and/or transgene-RDE expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions may be administered in a manner appropriate to the disease to be treated (or prevented). The quantity and frequency of administration will be determined by such factors as the condition of the patient, and the type and severity of the patient's disease, although appropriate dosages may be determined by clinical trials.

Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. The pharmaceutically acceptable excipients described in Remington's Pharmaceutical Sciences (Mack Pub. Co., N.J. 1991) (which is incorporated herein by reference in its entirety for all purposes) can be appropriately used. The composition can be formulated into a known form suitable for parenteral administration, for example, injection or infusion. The composition may comprise formulation additives such as a suspending agent, a preservative, a stabilizer and/or a dispersant, and a preservation agent for extending a validity term during storage.

A composition comprising the eukaryotic cells described herein as an active ingredient can be administered for treatment of, for example, a cancer (blood cancer (leukemia), solid tumor (ovarian cancer) etc.), an inflammatory disease/autoimmune disease (pemphigus vulgaris, lupus erythematosus, rheumatoid arthritis, asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR, DE-CAR, and/or Side-CAR polypeptide binds.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, intranasally, intraarterially, intratumorally, into an afferent lymph vessel, by intravenous (i.v.) injection, or intraperitoneally. In one aspect, the T cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection. The administration can be done by adoptive transfer.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). A pharmaceutical composition comprising the eukaryotic cells described herein may be administered at a dosage of $10^4$ to $10^9$ cells/kg body weight, in some instances $10^5$ to $10^6$ cells/kg body weight, including all integer values within those ranges. A eukaryotic cell composition may also be administered multiple times at these dosages. Eukaryotic cells can also be administered by using infusion techniques that are commonly known in immunotherapy (see, e.g., Rosenberg et al., New Eng. J. of Med. 319:1676, 1988, which is incorporated by reference in its entirety for all purposes).

Uses of Eukaryotic Cells

Nucleic acids encoding Smart CAR(s), DE-CAR(s), RDE-CAR(s), Smart-RDE-CAR(s), DE-RDE-CAR(s), Smart-DE-CAR(s), Smart-DE-RDE-CAR(s), Side-CAR(s), and/or transgene-RDE(s) can be used to express CAR, DE-CAR, Side-CAR, and/or transgene polypeptides in eukaryotic cells. The eukaryotic cell can be a mammalian cell, including for example human cells or murine cells. The eukaryotic cells may also be, for example, hematopoietic cells including, e.g., T-cells, natural killer cells, B-cells, or macrophages.

T-cells (e.g., CD4+ or CD8+) or natural killer cells can be engineered with a polynucleotide encoding a Smart CAR, DE-CAR, RDE-CAR, Smart-DE-CAR, Smart-RDE-CAR, DE-RDE-CAR, Smart-DE-RDE-CAR, and/or Side-CAR. Ligand for the RNA control device, DE, or Side CAR is added to the T-cells (e.g., CD4+ or CD8+) or natural killer cells can be added in increasing amounts to obtain a desired amount of effector function. The desired amount of effector function can be an optimized amount of effector function with a known amount (and/or density) of target antigen on target cells. Effector function can be target cell killing, activation of host immune cells, cytokine secretion, production of granzymes, production of apoptosis inducing ligands, production of other ligands that modulate the immune system, etc. The effector function can be secretion of cytokines such as, for example, IL-2, IFN-γ, TNF-α, TGF-β, and/or IL-10. Effector function can be the killing of target cells. Target cells can be killed with granzymes. Target cells can be induced to undergo apoptosis. Eukaryotic cells with CARs can kill target cells through apoptosis and granzymes.

The RDE, DE, RNA control device, or Side CAR regulatory element can be used to control expression of a transgene. This transgene expression can deliver a payload at a target site. These transgenes can also be carried by viral constructs, or viruses when the payload is a virus. Expression of the transgene can cause a desired change in the eukaryotic cell. An RDE regulated by GAPDH can be used for payload delivery, and the eukaryotic cell (e.g., T-cell, natural killer cell, B-cell, macrophage, dendritic cell, or other antigen presenting cell) can be activated (e.g., by a CAR) when it reaches the target site. Upon activation of the eukaryotic cell at the target site through the CAR, the cell induces glycolysis and the GAPDH releases from the RDE allowed payload expression and delivery. The target site can be a tumor or infection and the transgene could encode a cytokine, a chemokine, an antibody, a checkpoint inhibitor, a granzyme, an apoptosis inducer, complement, an enzyme for making a cytotoxic small molecule, an enzyme that cleaves peptides or saccharides (e.g., for digesting a biofilm), other cytotoxic compounds, or other polypeptides that can have a desired effect at the target site. Checkpoint inhibitors include agents that act at immune checkpoints including, for example, cytotoxic T-lymphocyte-associated antigen 4 (CTLA4), programmed cell death protein (PD-1), Killer-cell Immunoglobulin-like Receptors (KIR), and Lymphocyte Activation Gene-3 (LAG3). Examples of checkpoint inhibitors that may be used as payloads include, for example, Nivolumab (Opdivo), Pembrolizumab (Keytruda), Atezolizumab (Tecentriq), Ipilimumab (Yervoy), Lirilumab, and BMS-986016. Nivolumab, Atezolizumab and Pembrolizumab act at the checkpoint protein PD-1 and inhibit apoptosis of anti-tumor immune cells. Some checkpoint inhibitors prevent the interaction between PD-1 and its ligand PD-L1. Ipilimumab acts at CTLA4 and prevents CTLA4 from downregulating activated T-cells in the tumor. Lirilumab acts at KIR and facilitates activation of Natural Killer cells. BMS-986016 acts at LAG3 and activates antigen-specific T-lymphocytes and enhances cytotoxic T cell-mediated lysis of tumor cells. Cytokines can include, for example, IL-2, IL-12, IL-15, IL-18, IFN-γ, TNF-α, TGF-β, and/or IL-10. Cytotoxic agents can include, for example, granzymes, apoptosis inducers, complement, or a cytotoxic small molecule. The payload delivered at a target site (e.g., non-tumor target site) can be a factor that protects the target site such as, for example, an anti-inflammatory, a factor that attracts T-regulatory cells to the site, or cytokines or other factors that cause suppression and reduction in immune activity. The payload can be an enzyme that cleaves peptides or saccharides, for example hyaluronidase, heparanase, metalloproteinases and other proteinases which can be used, for example, to digest an undesired biofilm. The payload can be an imaging agent that allows the target site to be imaged. The payload may be a polypeptide that can be imaged directly, or it can be a polypeptide that interacts with a substrate to make a product that can be imaged, imaging polypeptides include, for example, thymidine kinase (PET), dopamine D2 (D2R) receptor, sodium iodide transporter (NIS), dexoycytidine kinase, somatostatin receptor subtype 2, norepinephrine transporter (NET), cannabinoid receptor, glucose transporter (Glut1), tyrosinase, sodium iodide transporter, dopamine D2 (D2R) receptor, modified haloalkane dehalogenase, tyrosinase, β-galactosidase, and somatostatin receptor 2. These reporter payloads can be imaged using, for example, optical imaging, ultrasound imaging, computed tomography imaging, optical coherence tomography imaging, radiography imaging, nuclear medical imaging, positron emission tomography imaging, tomography imaging, photo acoustic tomography imaging, x-ray imaging, thermal imaging, fluoroscopy imaging, bioluminescent imaging, and fluorescent imaging. These imaging methods include Positron Emission Tomography (PET) or Single Photon Emission Computed Tomography (SPECT).

Multiple systems are envisioned for use that can kill target cells directly. These include, for example, the introduction of a viral or a bacterial gene into target cells. This approach turns a non-toxic pro-drug to a toxic one. There are systems that have been extensively investigated: the cytosine deaminase gene ("CD") of *Escherichia coli*, which converts the pro-drug 5-Fluorocytosine ("5-FC") to 5-Fluorouracil ("5-FU"); and the herpes simplex virus thymidine kinase gene ("HSV-tk"), which converts ganciclovir ("GCV") to ganciclovir monophosphate, converted by the cancer cells' enzymes to ganciclovir triphosphate. The HSV-tk/GCV system useful in killing tumor cells directly, involves adenoviral transfer of HSV-tk to tumor cells, with the subsequent administration of ganciclovir. Specifically, recombinant replication-defective adenovirus is employed to transfer the thymidine, HSV-tk, into hepatocellular carcinoma ("HCC") cells to confer sensitivity to ganciclovir. Three useful HCC cell lines include, for example, Hep3B, PLC/PRF/5 and HepG2, which can efficiently infect, in vitro, by a recombinant adenovirus carrying lacZ reporter gene ("Ad-CMV-lacZ"). Expression of HSV-tk in HCC cells infected with a recombinant adenovirus carrying HSV-tk gene ("AdCM-Vtk") induces sensitivity to ganciclovir in a dose-dependent manner (Qian et al., Induction of sensitivity to ganciclovir in human hepatocellular carcinoma cells by adenovirus-mediated gene transfer of herpes simplex virus thymidine kinase, Hepatology, 22:118-123 (1995)) https://doi.org/10.1002/hep.1840220119.

Thymidine kinase can be used with PET reporter probes such as, for example, [$^{18}$F]9-(4-[$^{18}$F]-fluoro-3-hydroxymethylbutyl)-guanine, a fluorine-18-labelled penciclovir analogue, which when phosphorylated by thymidine kinase (TK) becomes retained intracellularly, or is 5-(76) Br-bromo-2'-fluoro-2'-deoxyuridine. The relevant reporter probes for each of the PET reporters are well known to the skilled artisan. An exemplary reporter probe for dopamine D2 (D2R) receptor is 3-(2'-[$^{18}$F]fluoroethyl)spiperone (FESP) (MacLaren et al., Gene Ther. 6(5):785-91 (1999)). An exemplary reporter probe for the sodium iodide transporter is $^{124}$I, which is retained in cells following transport by the transporter. An exemplary reporter probe for deoxycytidine kinase is 2'-deoxy-2'-$^{18}$F-5-ethyl-1-β-d-arabinofuranosyluracil ($^{18}$F-FEAU). An exemplary reporter probe for somatostatin receptor subtype 2 is $^{111}$In, $^{99m/94m}$Tc-, $^{90}$Y-, or $^{177}$Lu-labeled octreotide analogues, for example $^{90}$Y-, or $^{177}$Lu-labeled DOTATOC (Zhang et al., J Nucl Med. 50 (suppl 2):323 (2009)); $^{68}$Ga-DOTATATE; and $^{111}$In-DOTABASS (see. e.g., Brader et al., J Nucl Med. 54(2):167-172 (2013), incorporated herein by reference). An exemplary reporter probe for norepinephrine transporter is $^{11}$C-m-hydroxyephedrine (Buursma et al., J Nucl Med. 46:2068-2075 (2005)). An exemplary reporter probe for the cannabinoid receptor is $^{11}$C-labeled CB2 ligand, $^{11}$C-GW405833 (Vandeputte et al., J Nucl Med. 52(7):1102-1109 (2011)). An exemplary reporter probe for the glucose transporter is [$^{18}$F]fluoro-2-deoxy-d-glucose (Herschman, H. R., Crit Rev Oncology/Hematology 51:191-204 (2004)). An exemplary reporter probe for tyrosinase is N-(2-(diethylamino)ethyl)-$^{18}$F-5-fluoropicolinamide (Qin et al., Sci Rep. 3:1490 (2013)). Other reporter probes are described in the art, for example, in Yaghoubi et al., Theranostics 2(4):374-391 (2012), incorporated herein by reference.

An exemplary photoacoustic reporter probe for β-galactosidase is 5-bromo-4-chloro-3-indolyl-β-D-galactoside (X-gal) (Li et al., J Biomed Opt. 12(2):020504 (2007)). Exemplary X-ray reporter includes, among others, somatostatin receptor 2, or other types of receptor based binding agents. The reporter probe can have a radiopaque label moiety that is bound to the reporter probe and imaged, for example, by X-ray or computer tomography. Exemplary radiopaque label is iodine, particularly a polyiodinated chemical group (see, e.g., U.S. Pat. No. 5,141,739), and paramagnetic labels (e.g., gadolinium), which can be attached to the reporter probe by conventional means. Optical imaging agents include, for example, a fluorescent polypeptide. Fluorescent polypeptides include, for example, green fluorescent protein from *Aequorea victoria* or *Renilla reniformis*, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof. The optical imaging agent can also be a bioluminescent polypeptide. These include, for example, aequorin (and other $Ca^{+2}$ regulated photoproteins), luciferase based on luciferin substrate, luciferase based on Coelenterazine substrate (e.g., *Renilla, Gaussia,* and Metridina), and luciferase from Cypridina, and active variants thereof.

Smart CAR, DE-CAR, RDE-CAR, Smart-DE-CAR, Smart-RDE-CAR, DE-RDE-CAR, Smart-DE-RDE-CAR, Side-CAR and/or universal-CARs can be designed to include receptors against antigens that are of bacterial, fungal or viral origin. Because Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can be utilized to fight infections, which are a source of toxicity in immunocompromised patients, such anti-pathogen Smart CAR(s), DE-CAR(s), RDE-CAR(s), Smart-RDE-CAR(s), DE-RDE-CAR(s), Smart-DE-CAR(s), Smart-DE-RDE-CAR(s) and/or Side-CAR(s) can be used in conjunction Smart CAR, DE-CAR, RDE-CAR, Smart-DE-CAR, Smart-RDE-CAR, DE-RDE-CAR, Smart-DE-RDE-CAR, and/or Side-CAR T-cell therapy specific for a TAA.

A eukaryotic cell can bind to a specific antigen via the CAR, DE-CAR, and/or Side-CAR polypeptide causing the CAR, DE-CAR, and/or Side-CAR polypeptide to transmit a signal into the eukaryotic cell, and as a result, the eukaryotic cell can be activated and so express an appropriate RDE-transgene. The activation of the eukaryotic cell expressing the Smart CAR, DE-CAR, RDE-CAR, Smart-DE-CAR, Smart-RDE-CAR, DE-RDE-CAR, Smart-DE-RDE-CAR, and/or Side-CAR is varied depending on the kind of a eukaryotic cell and the intracellular element of the Smart CAR, DE-CAR, RDE-CAR, Smart-DE-CAR, Smart-RDE-CAR, DE-RDE-CAR, Smart-DE-RDE-CAR, and/or Side-CAR. The eukaryotic cell can express a RDE transcript that poises the cell for effector function upon stimulation of the eukaryotic cell through a Smart CAR, DE-CAR, RDE-CAR, Smart-DE-CAR, Smart-RDE-CAR, DE-RDE-CAR, Smart-DE-RDE-CAR, and/or Side-CAR.

A eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be used as a therapeutic agent to treat a disease. The therapeutic agent can comprise the eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide as an active ingredient, and may further comprise a suitable excipient. Examples of the excipient include pharmaceutically acceptable excipients for the composition. The disease against which the eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide is administered is not particularly limited as long as the disease shows sensitivity to the eukaryotic cell and/or the product of the RDE-transgene.

Examples of diseases that can be treated include a cancer (blood cancer (leukemia), solid tumor (ovarian cancer) etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis, other immune mediated diseases such as neurodegenerative diseases like Alzheimer's or Parkinson's, and metabolic diseases like diabetes. A receptor (e.g., a CAR) can target the eukaryotic cell to the diseased cell(s) and when the receptor binds to its target at the diseased cell(s) the receptor can send a signal into the eukaryotic cell leading to expression of the RDE-transgene. The RDE-transgene encodes a polypeptide that is useful in treating or killing the diseased cell(s). A cancer and/or solid tumor can be treated with a eukaryotic cell expressing receptor that binds to a tumor associated (or cancer associated) antigen, such as those described above. When the receptor binds to the tumor associated antigen the receptor sends a signal into the cell that causes the RDE-transgene to be expressed (e.g., the signal effects an RDE binding protein leading to expression of the RDE-transcript). The RDE-transcript can encode a polypeptide that activates the eukaryotic cell so that the eukaryotic cell treats the cancer and/or the RDE-transcript encodes a polypeptide that itself treats the cancer (e.g., a cytotoxic polypeptide).

An autoimmune disease (e.g., pemphigus vulgaris, lupus erythematosus, rheumatoid arthritis, multiple sclerosis, Crohn's disease) can be treated with a eukaryotic cell expressing a RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide that binds to the immune proteins associated with the autoimmune disease. The receptor or targeting polypeptide can trigger expression of the RDE-transgene that encodes a polypeptide useful in treating the autoimmune disease (e.g., the polypeptide can regulate the cells causing the autoimmune disease or kill these cells). The eukaryotic cell expressing the RDE-transgene or RDE transcript, and receptor or targeting polypeptide can target cells that make an antibody involved with the autoimmune disease (e.g., the RDE-transgene can encode a polypeptide that kills the antibody producing cells or that inhibits the production of antibody by these cells). The eukaryotic cell expressing the RDE-transgene or RDE transcript, and receptor or targeting polypeptide can target T-lymphocytes involved with the autoimmune disease (e.g., the RDE-transgene can encode a polypeptide that kills the target T-lymphocytes or that regulates the activity of the T-lymphocytes).

Eukaryotic cells expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be used as a therapeutic agent to treat an allergy. Examples of allergies that can be treated include, for example, allergies to pollen, animal dander, peanuts, other nuts, milk products, gluten, eggs, seafood, shellfish, and soy. The eukaryotic cell expressing the RDE-transgene or RDE transcript, and receptor or targeting polypeptide can target cells that make an antibody which causes the allergic reaction against, for example, pollen, animal dander, peanuts, other nuts, milk products, gluten, eggs, seafood, shellfish, and soy. The targeted cells can be one or more of B-cells, memory B-cells, plasma cells, pre-B-cells, and progenitor B-cells. Targeted cells can also include T-lymphocytes which cause the allergic reaction against, for example, pollen, animal dander, peanuts, other nuts, milk products, gluten, eggs, seafood, shellfish, and soy. Eukaryotic cells expressing the RDE-transgene or RDE transcript, and receptor or targeting polypeptide can bind to the idiotypic determinant of the antibody or T-cell receptor.

The eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be administered for treatment of a disease or condition. For example, the eukaryotic cell can be utilized to treat an infectious disease. The eukaryotic cell can express a receptor or targeting polypeptide that binds to an antigen found on the infectious disease causing agent or a cell infected with such an agent. The receptor or targeting polypeptide binds the antigen associated with the infectious disease and sends a signal into the eukaryotic cell that leads to expression of the RDE-transgene. The RDE-transgene encodes a product that can activate the eukaryotic cell for treating the infectious disease (e.g., the eukaryotic cell can produce a cytotoxic polypeptide or a cytokine that activates immune cells). The RDE-transgene can also encode a polypeptide that itself is a cytotoxic polypeptide or a cytokine. The eukaryotic cell can also be utilized for prevention of an infectious disease (used prophylactically), for example, after bone marrow transplantation or exposure to radiation, donor lymphocyte transfusion for the purpose of remission of recurrent leukemia, and the like.

The therapeutic agent comprising the eukaryotic cell expressing the RDE-transgene or RDE transcript, and optionally, a Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

The RDE-transgene or RDE transcript, and optionally, Smart CAR, DE-CAR, RDE-CAR, Smart-DE-CAR, Smart-RDE-CAR, DE-RDE-CAR, Smart-DE-RDE-CAR, Side-CAR, T-cell receptor, B-cell receptor, innate immunity receptor and/or other receptor or targeting polypeptide can be used with a T-lymphocyte that has aggressive anti-tumor properties, such as those described in Pegram et al, CD28z CARs and armored CARs, 2014, Cancer J. 20(2):127-133, which is incorporated by reference in its entirety for all purposes. The RDE transcript can encode a polypeptide that causes aggressive anti-tumor properties in the T-lymphocyte.

A transgene, a CAR, DE-CAR, and/or Side CAR polypeptides can be controlled by an RDE from the 3'-UTR of the gene encoding IL-2 or the 3'-UTR of IFN-γ. These RDEs can be modified to inactivate microRNA sites found in the RDE. Using these control elements makes expression of the CAR, DE-CAR, Side-CAR, and/or transgene sensitive to changes in the glycolytic state of the host cell through the interaction of the RDE with glyceraldehyde-3-phosphate dehydrogenase (GAPDH). When the host cell is in a quiescent state a large proportion of the GAPDH is not involved in glycolysis and is able to bind to the RDE resulting in reduced translation of the transcript encoding the CAR, DE-CAR, Side-CAR, and/or transgene polypeptides. When the host cell is induced to increase glycolysis, e.g., by providing the host cells with glucose, or other small molecules that will increase glycolytic activity, GAPDH becomes enzymatically active and is not able to bind to the RDE. The reduction in GAPDH binding to the RDE increases translation of the transcripts (e.g., by increasing half-life of the transcript and/or by increasing the translation rate) encoding the CAR, DE-CAR, Side-CAR, or other transgene. The glycolytic activity of GAPDH can be increased by increasing the amount and/or activity of triose isomerase. The host cell can be induced to over-express a recombinant triose isomerase, and this over-expression increases the glycolytic activity of GAPDH. A glycolysis inhibitor can be added to decrease expression of the transcript with the RDE. Such glycolysis inhibitors include for example, dimethylfumarate (DMF), rapamycin, 2-deoxyglucose, 3-bromophyruvic acid, iodoacetate, fluoride, oxamate, ploglitazone, dichloroacetic acid, quinones, or other metabolism inhibitors such as, for example, dehydroepiandrosterone. Expression from the RDE controlled transcript can be increased by the addition of GAPDH (or other RDE binding protein) inhibitor that inhibits binding of the RDE by GAPDH (or other RDE binding protein). Such GAPDH inhibitors include, for example, CGP 3466B maleate or Heptelidic acid (both sold by Santa Cruz Biotechnology, Inc.), pentalenolactone, or 3-bromopyruvic acid.

Constructs encoding transcripts with RDEs can be expressed in eukaryotic cells to bind to RDE binding proteins and so reduce the ability of those RDE binding proteins to interact with native transcripts in the cell. The recombinant transcripts can compete for binding of RDE binding proteins and this can reduce the inhibition and/or activation of native transcripts within the eukaryotic cell by the RDE binding proteins. The constructs encoding transcripts with the RDEs can be used in this way to change when and how native transcripts are expressed in the eukaryotic cell. The eukaryotic cell can be a T-cell, natural killer cell, or B-cell and the recombinant transcript has RDEs that are shared with cytokine or cytotoxic transcripts (e.g., in their 3' untranslated regions). The recombinant transcript can compete for binding with the RDE binding proteins (e.g., GAPDH and/or other glycolytic enzymes described above) that regulate expression of the cytokine or cytotoxic polypeptide and change the threshold (e.g., glycolysis activity for GAPDH) needed to express the cytokine or cytotoxic polypeptide. This can be used to create super T-cell (aka Angry T-cells or Hornet T-cells) that will secrete higher amounts of cytokines and/or cytotoxic proteins (greater $C_{max}$) in response to stimulation of the immune cell (e.g., through a CAR or T-cell receptor). T-cells can be reprogrammed with a recombinant transcript encoding an RDE from an IL-2 transcript so that when the T-cell is stimulated by its T-cell receptor it produces more IL-2 and other effector polypeptides with faster kinetics. These reprogrammed T-cells can also produce other inflammatory cytokines and cytotoxic polypeptides (e.g., granzymes and/or perforins) in larger amounts and with faster kinetics. Reprogramming T-cells and natural killer cells into such Angry/Hornet states can be useful for treating disease and disorders, including, for example, tumors, other cancers, and infectious diseases.

RDEs can be used to reduce CAR expression in immune cells until those immune cells are activated by target or at a desired time. This can result in expression of the CAR at desired times for therapeutic effect while reducing the systemic exposure of a subject to the CAR. The reduced systemic exposure can reduce and/or inhibit the development of an immune response against the CAR as the subject's immune system will see less CAR over time.

Some neural degenerative diseases and syndromes are associated with inflammation, as are a number of other non-neural diseases and syndromes. Such inflammation associated diseases can be treated, at least in part, by providing a subject with small molecules (or other molecules) that increase the availability of inhibitory RDE binding proteins within immune cells. Such small molecules include, for example, glycolysis inhibitors (e.g., dimethylfumarate (DMF), rapamycin, 2-deoxyglucose, 3-bromophyruvic acid, iodoacetate, fluoride, oxamate, ploglitazone, dichloroacetic acid), other metabolic inhibitors (e.g., dehydroepiandrosterone), etc. For example, glycolytic inhibitors reduce glycolysis in the cell and can increase the amount of free GAPDH (not involved in glycolysis) for binding to RDEs reducing the expression of these transcripts. A number of inflammatory gene products in immune cells (e.g., gene products that activate the immune system) are regulated by RDEs that can bind GAPDH. Decreasing glycolysis increases the amount of free GAPDH for RDE binding, increases the amount of GAPDH bound to the RDEs of these inflammatory genes and reduces the expression of these inflammatory genes. Inflammatory genes include proinflammatory cytokines such as, for example, IL-1, TNF-α, INF-g, and GM-CSF. These cytokines have 3'-UTRs with RDEs that can bind RDE binding proteins, including GAPDH, to regulate their expression. The increased GAPDH can bind to these RDEs and decrease the expression of these proinflammatory cytokines. Reduced expression of proinflammatory cytokines could reduce activity of the immune system in these subjects reducing inflammation. The reduction in inflammation can have positive therapeutic effects alleviating symptoms and/or treating the underlying disease state in these inflammation related neural diseases, as well as in other inflammation associated diseases and syndromes.

RDEs (e.g., AU elements) can be selected to provide maximal expression at a desired time point and to provide a desired amount of polypeptide at that time point. RDEs can also be selected to provide a desired area under the curve for a polypeptide. As shown in Table 2 of Example 20, different RDEs (e.g., AU elements) reached maximal rates of expression at different times. Also as shown in Table 1, different RDEs provided different amounts of expression with different profiles over time providing different AUC. Using these RDEs in combination with different transgenes allows temporal programming of when the different transgenes reach maximal rates of expression in relation to one another following activation of a cell. In addition, using different RDEs one can program the transgenes to express a desired amount of transgene encoded polypeptide and/or a desired amount of AUC or exposure to the polypeptide encoded by the transgene. Thus, RDEs can be used to provide control that produces desired amounts of different transgene polypeptides at a different (or the same) desired times.

This temporal control can be used to provide desired timing for the production of different transgene polypeptides within a cell. Using this temporal control, a cell can be programmed to express a first transgene that alters the state of the cell so that is prepared to be affected by the polypeptide of a second transgene that is expressed at a later time. For example, the first expressed polypeptide could induce the cell to make and store cytotoxic polypeptides (e.g., granzymes and/or perforins) and the second expressed polypeptide could be involved in the release of the cytotoxic polypeptides. Another example of temporal expression involves it use to program a cell to undergo changes (e.g., differentiation or changing a state of the cell) that requires temporal expression of two or more gene products. RDEs can be used to mimic this temporal expression allowing one to control when the cell changes its state or differentiates (e.g., programmed differentiation of stem cells). In a stem cell example, the temporal and induction control can be used to program a stem cell to differentiate when (and where) it is desired to have the stem cell differentiate into a desired cell type.

The temporal control can also be used to provide desired timing of the production of different transgene polypeptides outside of the cell. Using this temporal control, a cell can be activated and secrete a first transgene polypeptide that conditions and/or alters a target cell so that the target cell is prepared to be acted upon by a polypeptides expressed at later time from a second transgene. For example, the first polypeptide could induce a target cell to express a receptor on the target cell surface (e.g., FasR, Her2, CD20, CTLA-4, PD-L1, etc.) or a polypeptide in the cell. The first transgene could also induce the cell to secrete a factor that induces the target cell to change its state (e.g., the first transgene could induce the cell to secrete CpG which causes the target cell to express OX40 on the target cell surface). The second transgene that reaches maximal rate of expression at a later time can encode a polypeptide that acts on the induced surface receptor (e.g., FasL, Herceptin, Rituximab, Ipilimumab, Nivolumab, anti-OX40 antibody, etc.). The temporal and induction control can also be used to change the state or differentiation of a target cell by providing to the target cell polypeptides in a timed manner where the first polypeptide induces the target cell to alter its state (e.g., differentiation) so that it can be acted upon by the second polypeptide (etc. for additional transgene polypeptides which reach maximal rate of expression at later times).

Some examples of diseases and payloads that can be treated using RDEs (Gold elements) with different kinetic parameters (e.g., an RDE that gives rapid expression early after activation of the cell followed by a rapid decline in expression or an RDE that delays expression after cell activation for 2-3 days) include the following: DLL3 positive cancers (such as IDH1mut gliomas, melanoma, and SCLC) using an anti-DLL3 CAR and a payload of one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-12, IL-15, IL-18, INFγ, miRNA (e.g., mir155), and/or CD40 ligand. CD19 positive lymphomas (e.g., NHL) using an anti-CD19 CAR and a payload of IL-12, or one or more of anti-4-1BB antibody, anti-CD11b antibody, anti-CTLA4 antibody, anti-IL11b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), and/or CD40 ligand. AML with onco-CD43 (sialylation mutant) using an anti-onco-CD43 CAR that recognizes the mutated sialylation and a payload of one or more of anti-CXCL12 antibody, anti-anti-CXCR4 antibody, or IL-12, or one or more of anti-4-1BB antibody, anti-CD11b antibody, anti-CTLA4 antibody, anti-IL1b antibody, a BiTE, CCL2, HAC, heparinase, hyaluronidase, Hsp60, Hsp70, IL-2, IL-15, IL-18, INFγ, miRNA (e.g., mir155), and/or CD40 ligand. PSCA positive prostate cancer, bladder cancer or pancreatic cancer using an anti-PSCA CAR and a payload of heparinase or IL-12, or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, hyaluronidase, Hsp60, Hsp70, IL-2, IL-15, IL-18, INFγ, miRNA (e.g., mir155), and/or CD40 ligand. Triple negative breast cancer with a CAR that recognizes cancer testis antigen, misfolded or mutant EGFR (associated with triple negative breast cancer), and/or folate receptor alpha peptide and a payload of IL-12 or one or more of anti-4-1BB antibody, anti-CD11b antibody, anti-CTLA4 antibody, anti-IL1b antibody, a BiTE, CCL2, anti-CXCR4 antibody, anti-CXCL12 antibody, HAC, heparinase, hyaluronidase, Hsp60, Hsp70, IL-2, IL-15, IL-18, INFγ, miRNA (e.g., mir155), and/or CD40 ligand.

The inventions disclosed herein will be better understood from the experimental details which follow. However, one skilled in the art will readily appreciate that the specific methods and results discussed are merely illustrative of the inventions as described more fully in the claims which follow thereafter. Unless otherwise indicated, the disclosure is not limited to specific procedures, materials, or the like, as such may vary. It is also to be understood that the terminology used herein is for the purpose of describing particular embodiments only and is not intended to be limiting.

EXAMPLES

Example 1. Control of T-Cell Effector Activity with an RDE-CAR

A RDE Car is made using the third generation anti-CD19 CAR cassette described in WO 2012/079000, which is hereby incorporated-by-reference in its entirety for all purposes), and the 3'-UTR of the gene encoding IL-2 (NCBI Reference Sequence Number: NM_000586.3), which is hereby incorporated by reference in its entirety for all purposes). A nucleic acid encoding the IL-2 3'-UTR is engineered into the anti-CD19 CAR cassette in an appropriate expression vector. The IL-2, 3'-UTR sequence used was:

(SEQ ID NO: 21)
taattaagtgatcccacttaaaacatatcaggccttctATTTATTTAaat

ATTTAaattttatATTTAttgttgaatgtatggtttgctacctattgtaa ctattattcttaatcttaaaactataaatatggatcttttatgattcttt ttgtaagccctaggggctctaaaatggtttcacttATTTAtcccaaaatA TTTAttattatgttgaatgttaaatatagtatctatgtagattggttagt aaaactATTTAataaatttgataaatataaa The anti-CD19 RDE CAR and anti-CD19 CAR constructs are transfected by routine methods into different populations of T-cells (primary human T-cells), and stable populations of T-cells are selected using appropriate antibiotics (or other selection schemes). T-cell populations with anti-CD19 RDE CARs (CD19⁻/CD22⁻/CD3⁺) and T-cell populations with anti-CD19 CARs (CD19⁻/CD22⁻/CD3⁺) are activated by co-incubation with anti-CD3/CD28 beads and allowed to return to quiescent state after debeading.

Quiescent anti-CD19 RDE CAR T-cells are co-cultured with CD19⁺/CD22⁺/CD3⁻ Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The RDE-CAR T-cells and the Raji cells are grown together for 24 hours. Cultures are washed, and then stained with anti-CD22 and anti-CD3 reagents, followed by counting of CD22⁺ (Raji target cells) and CD3⁺ cells (Smart CAR T-cells). These measurements will identify the target cell killing rate (e.g., half-life) and the proliferation rate of the RDE-CAR T-cells at different levels of RDE-CAR expression.

Activated anti-CD19 RDE CAR T-cells are co-cultured with CD19⁺/CD22⁺/CD3⁻ Raji target cells at RDE CAR T-cell:Raji target ratios of 2:1, 5:1, and 10:1. The glycolysis activator glucose is added to the culture medium at concentrations in the range of 1.0 mM to 10 mM (1 mM, 2, mM, 3 mM, 4 mM, 5 mM, 7.5 mM and 10 mM). The RDE-CAR T-cells and the Raji cells are grown together for 24 hours. Samples from culture media are taken and tested for IL-2 by ELISA.

As a control activated anti-CD19 CAR T-cells are co-cultured with CD19+/CD22+/CD3− Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 24 hours. Cultures are washed, and then stained with anti-CD22 and anti-CD3 reagents, followed by counting of CD22+ (Raji target cells) and CD3+ cells (CAR T-cells).

As a control, activated anti-CD19 CAR T-cells are co-cultured with CD19+/CD22+/CD3− Raji target cells at CAR T-cell:Raji target ratios of 2:1, 5:1, and 10:1. The glycolysis activator glucose is added to the culture medium at concentrations in the range of 1.0 mM to 10 mM (1 mM, 2 mM, 3 mM, 4 mM, 5 mM, 7.5 mM and 10 mM). The CAR T-cells and the Raji cells are grown together for 48 hours. Samples from culture media are taken and tested for IL-2 by ELISA.

Example 2: Removal of MicroRNA Binding Sites from an RDE

The AU-rich element from the 3'-UTR of IL-2 has mir-181 and mir 186 microRNA binding sites. Different combinations of the microRNA sites were removed from the 3'-UTR of IL-2. When the MIR186 micro-RNA sites were removed from the 3'-UTR of IL-2 the dynamic range of expression from constructs with this UTR increased 50 fold. The modified IL-2, 3'-UTR replaces CTT in the sequence with GAA and is shown below (the new GAA is underlined in the sequence):

(SEQ ID NO: 22)
taattaagtgatcccacttaaaacatatcaggccttctATTTATTTAaat

ATTTAaattttatATTTAttgttgaatgtatggtttgctacctattgtaa ctattattcttaatcttaaaactataaatatggatcttttatgattGAAt ttgtaagccctaggggctctaaaatggtttcacttATTTAtcccaaaatA TTTAttattatgttgaatgttaaatatagtatctatgtagattggttagt aaaactATTTAataaatttgataaatataaa The AU-rich element from the 3'UTR of IFNg also has micro-RNA binding sites characterized as mir-125. The sequence of the IFNg RDE is:

(SEQ ID NO: 23)
tggttgtcctgcctgcaatatttgaattttaaatctaaatctATTTAtta atATTTAacattATTTAtatggggaatatattttagactcatcaatcaa ataagtATTTAaatagcaacttttgtgtaatgaaaatgaatatctatta atatatgtattATTTAtaattcctatatcctgtgactgtctcacttaatc ctttgttttctgactaattaggcaaggctatgtgattacaaggctttatc tcaggggccaactaggcagccaacctaagcaagatcccatgggttgtgtg tttatttcacttgatgataccaatgaacacttataagtgaagtgatactat ccagttactgccggtttgaaaatatgcctgcaatctgagccagtgcttta atggcatgtcagacagaacttgaatgtgtcaggtgaccctgatgaaaaca tagcatctcaggagatttcatgcctggtgcttccaaatattgttgacaac tgtgactgtacccaaatggaaagtaactcatttgttaaaattatcaatat ctaatatatatgaataaagtgtaagttcacaacta Different combinations of the micro-RNA sites were removed from the 3'UTR of IFNg and tested for increased expression. When the mir125 micro-RNA sites were removed from the 3'-UTR of IFN-γ the expression rate from constructs with this UTR is increased.

Expression of GFP in T-cells, transfected with the RDE-GFP plus the microRNA sites, is compared to expression of GFP in T-cells with the RDE-GFP in which the microRNA sites have been removed, following activation with CD3/CD28 beads for 24 hours. The removal of the microRNA sites increased expression of the GFP by a factor of between 2-5 after 24 hours, relative to the cells with microRNA sites.

Example 3: Payload Delivery to DLBCL Using an Anti-CD19 CAR T-Cell

The anti-CD19 Smart CAR T-lymphocytes and anti-CD19 CAR T-cell lymphocytes of Example 6 are used in this example. These CAR T-lymphocytes are further engineered to include a construct encoding a PD-1 inhibitor under the control of the 3'-UTR of IL2 that has been modified by removal of the MIR186 sites. PD-1 inhibitors expressed by the construct include, for example, Pembrolizumab (Keytruda®), Nivolumab (Opdivo®), Atezolizumab (Tecentriq®), BMS-936558, Lambrolizumab, or polypeptides derived from these drugs. Other PD-1 inhibitors that may be expressed by the construct include those disclosed in Herbst et al., J Clin Oncol., 31:3000 (2013); Heery et al., J Clin Oncol., 32:5s, 3064 (2014); Powles et al., J Clin Oncol, 32:5s, 5011 (2014); Segal et al., J Clin Oncol., 32:5s, 3002 (2014), or U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and 8,217,149.

T-cell populations with anti-CD19 Smart CARs/PD-1 (CD19−/CD22−/CD3+) and T-cell populations with anti-CD19 CARs/PD-1 (CD19−/CD22−/CD3+) are activated by co-incubation with anti-CD3/CD28 beads. T-cells with anti-CD19 Smart CARs/PD-1 inhibitor or anti-CD19 CARs/PD-1 inhibitor were incubated with theophylline at 0, 75 and 250 µM for 72 hours. Activated anti-CD19 Smart CAR/PD-1 T-cells or anti-CD19 CAR/PD-1 T-cells were co-cultured with CD19+/CD22+/CD3− Raji target cells at Smart CAR/PD-1 T-cell:Raji target ratios of 2:1, 5:1, and 10:1. Ligand for the RNA control device, theophylline is maintained in the culture medium at concentrations of 0 µM, 75 µM, and 250 µM. The Smart-CAR/PD-1 T-cells or CAR/PD-1 T-cells and the Raji cells are grown together for 18 hours. Cultures are washed, and then stained with anti-CD22 and anti-CD3 reagents, followed by counting of CD22+(Raji target cells) and CD3+ cells (Smart CAR T-cells). Samples from culture media are also taken at 6, 12 and 18 hours, and tested for PD-1 inhibitor by ELISA.

Example 4: Payload Delivery to AML Using an Anti-CD133 CAR T-Cell

A CAR is made using the anti-CD20 CAR cassette described in Budde 2013 (Budde et al. PLoS1, 2013 doi:

10.1371/journal.pone.0082742, which is hereby incorporated by reference in its entirety for all purposes), with the anti-CD133 mAb 293C3-SDIE is used for the extracellular element (Rothfelder et al., 2015, ash.confex.com/ash/2015/webprogram/Paper81121.html, which is incorporated by reference in its entirety for all purposes) replacing the anti-CD20 extracellular domain. The anti-CD133 CAR also can encode the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the anti-CD20 CAR cassette is engineered to replace the anti-CD20 extracellular domain with the anti-CD133 element, and optionally the RNA control device is also engineered into the cassette. The anti-CD133 CAR with or without the RNA control device are cloned into appropriate expression vectors.

These anti-CD133 CAR and anti-CD133 Smart CAR constructs are transfected by routine methods into T-lymphocytes (Jurkat cells and/or primary human T-lymphocytes), and stable populations of T-lymphocytes are selected using appropriate antibiotics (or other selection schemes).

These CAR T-lymphocytes are further engineered to include a construct encoding a PD-1 inhibitor under the control of the RDE from the 3'-UTR of IL2 that has been modified by removal of a MIR186 site. PD-1 inhibitors expressed by the construct include, for example, Pembrolizumab (Keytruda®), Nivolumab (Opdivo®), Atezolizumab (Tecentriq®), BMS-936558, Lambrolizumab, or polypeptides derived from these drugs. Other PD-1 inhibitors that may be expressed by the construct include those disclosed in Herbst et al., J Clin Oncol., 31:3000 (2013); Heery et al., J Clin Oncol., 32:5s, 3064 (2014); Powles et al., J Clin Oncol, 32:5s, 5011 (2014); Segal et al., J Clin Oncol., 32:5s, 3002 (2014), or U.S. Pat. Nos. 8,735,553; 8,617,546; 8,008,449; 8,741,295; 8,552,154; 8,354,509; 8,779,105; 7,563,869; 8,287,856; 8,927,697; 8,088,905; 7,595,048; 8,168,179; 6,808,710; 7,943,743; 8,246,955; and 8,217,149.

T-lymphocyte populations with anti-CD133 CAR/PD-1 inhibitor or anti-CD133 Smart CAR/PD-1 inhibitor (CD20$^-$/CD22$^-$/CD3$^+$) are activated by co-incubation with anti-CD3/CD28 beads.

Activated anti-CD133 CAR/PD-1 inhibitor or anti-CD133 Smart CAR/PD-1 inhibitor T-lymphocytes are co-cultured with CD133$^+$/CD3$^-$ AML target cells (e.g., U937, MV4-11, MOLM-14, HL-60 and/or KG1a) at anti-CD133 CAR and/or anti-CD133 Smart CAR T-lymphocyte:AML target ratios of 2:1, 5:1, and 10:1. Ligand for the RNA control device, theophylline, is added to the culture medium at concentrations in the range of 500 µM to 1 mM (lower or greater concentrations can be used to titrate Smart-CAR activity to the desired level). The anti-CD133 CAR/PD-1 inhibitor and/or anti-CD133 Smart CAR/PD-1 inhibitor T-lymphocytes and the AML cells are grown together for 48 hours. Cultures are washed, and then stained with anti-CD133 and anti-CD3 reagents, followed by counting of CD133$^+$ (AML target cells) and CD3$^+$ cells (anti-CD133 CAR, anti-CD133 DE-CAR, anti-CD133 Smart CAR, and/or the anti-CD133 DE-Smart CAR T-lymphocytes). These measurements will identify the target cell killing rate (e.g., half-life) and the proliferation rate of the anti-CD133 CAR/PD-1 inhibitor and/or anti-CD133 Smart CAR/PD-1 inhibitor T-lymphocytes at different levels of CAR expression. Samples from culture media are also taken at 12, 24, 26 and 48 hours, and tested for PD-1 inhibitor by ELISA.

Example 5: An RDE Construct for Expressing a Second Transgene

Constructs were made using an anti-CD19 CAR cassette as described in WO 2012/079000, which is hereby incorporated-by-reference in its entirety for all purposes), and a GFP-RDE1 (3'-UTR from IFNg) insert. These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was MinP and the RDE was the endogenous 3'-UTR of IFNg. The control region of the anti-CD19 CAR cassette was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed an increase in fluorescence when cultured with Raji target cells (activate CAR) of 1.0% to 6.5% (about 6.5 fold), and increase in fluorescence when cultured with CD3/CD28 beads (activate TCR) of 1.0% to 4.4% (about 4.4 fold). The transformed T-cells showed a change in activated cells in the population when cultured with Raji cells of 0.9% to 84.8%, and when cultured with CD3/CD28 beads of 0.9% to 90.8%.

Example 6: A Modified RDE2 Construct for Expressing a Second Transgene

Constructs were made using an anti-CD19 CAR cassette as described in Examples 11 and 12, and a GFP-RDE2.1 (IL-2 RDE) insert. The RDE2.1 was modified to remove the MIR186 microRNA sites, altering nucleotides from the 3'-UTR of IL-2 which was used as RDE2.

These two inserts/cassettes were placed in the same lenti virus construct. The anti-CD19 CAR cassette and the insert with the GFP-RDE are transcribed in opposite directions, and the control regions for each are located in between the two insert/cassettes. The control region for the GFP-RDE insert was a MinP. The control region of the anti-CD19 CAR cassette in was MND (as described above). CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and GFP expression in the T cells.

The transduced T-cells showed a change in activated cells in the population when cultured with Raji cells of 3.9% to 12.1%, and when cultured with CD3/CD28 beads of 3.9% to 11.1%.

Example 7: An RDE Construct for Expressing a Luciferase Transgene

Constructs were made using an anti-CD19 CAR cassette as described in WO 2012/079000, which is hereby incorporated-by-reference in its entirety for all purposes), and a Luciferase-RDE1 (3'-UTR of IFNg, Gold1) insert or a Luciferase-3'-UTR (a 3'-UTR that does not confer differential transgene translation in response to metabolic state of the cell, 3'-UTR). The anti-CD19 CAR cassette and the insert with the luciferase-RDE1 are transcribed in opposite directions, and the control regions for each are located in between the two insert/cassettes. The control region for the Luciferase-RDE1 insert and Luciferase-3'-UTR were either a MinP promoter or an NFAT promoter having the sequences of:

(MinP)
SEQ ID NO: 24
TAGAGGGTATATAATGGAAGCTCGACTTCCAG (NFAT)
SEQ ID NO: 25
GGAGGAAAAACTGTTTCATACAGAAGGCGTGGAGGAAAAACTGTTTCATA
CAGAGGCGTGGAGGAAAAACTGTTTCATACAGAAGGCGTAGATCTAGAC
TCTAGAGGGTATATAATGGAAGCTCGAATTC

The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set and the "CD3/CD28 Beads" set, CD19+ Raji B cells or anti-CD3/anti-CD28 beads were incubated with the transduced T cells for 24 h. At 24 h, the T cells were stained for CD25 and CD69, which are activation markers, and subject to flow cytometry to measure these markers and luciferase expression in the T cells.

Figure 2:
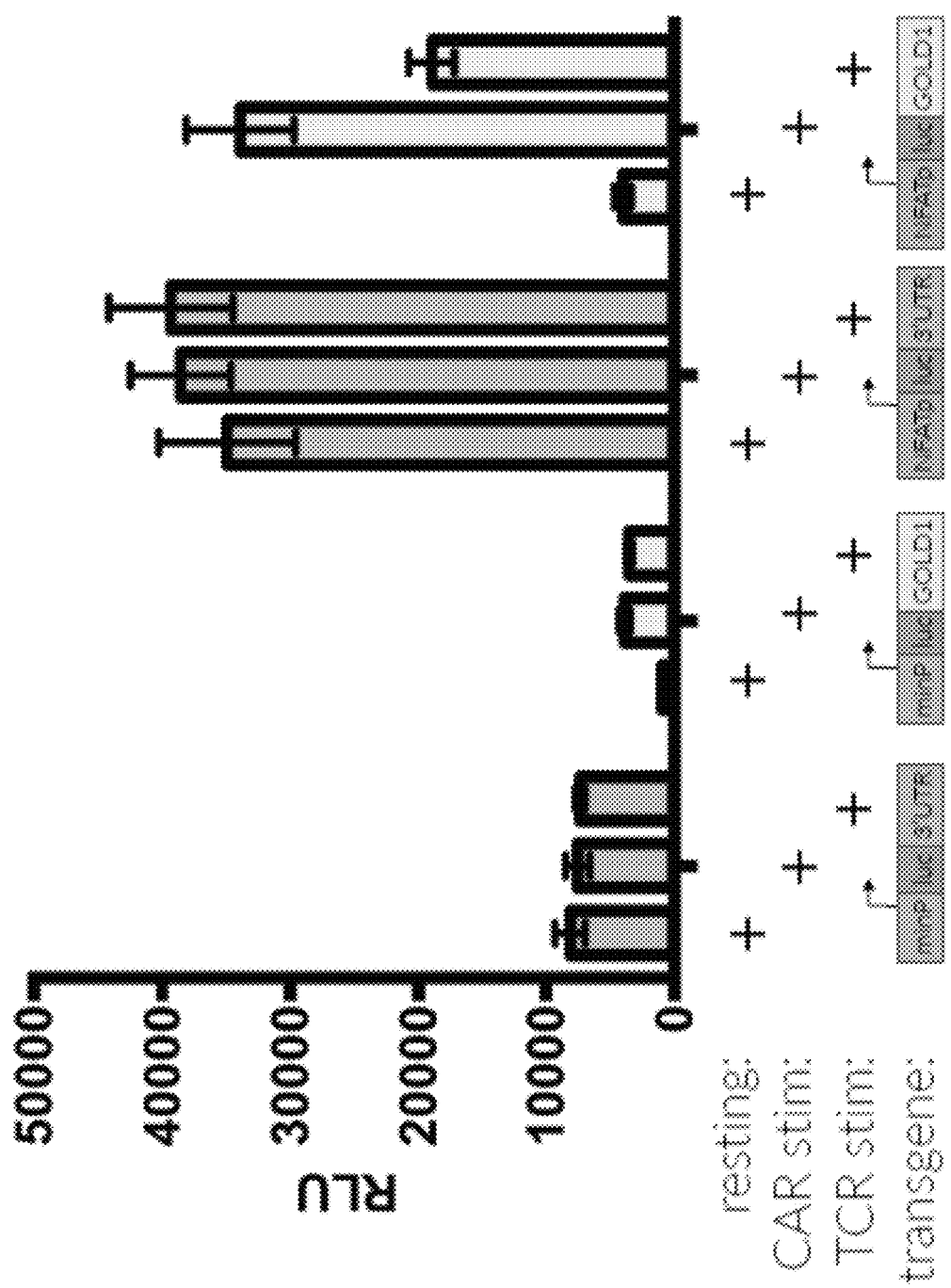
FIG. 2 shows a graph for the bioluminescence from T-cells with luciferase controlled by an RDE following activation of the T-cell by Raji target cells (activate CAR) or by CD3/CD28 beads (activate TCR) as compared to bioluminescence of T-cells at resting.

FIG. 2 shows that the transduced T-cells had an increase in bioluminescence when cultured with Raji target cells (activate CAR) or when cultured with CD3/CD28 beads (activate TCR) as compared to bioluminescence of T-cells at resting. The T-cells with a NFAT promoter and the 3'-UTR of IFNg (Gold1) showed a larger on-off response from CAR stimulation versus TCR stimulation. Under all conditions, T-cells with Gold1 had lower amounts of bioluminescence than T-cells under the same conditions (and same promoter) with Luciferase that was not controlled by the 3'UTR of IFNg (3'-UTR).

Example 8: Comparison of RDEs Controlling Luciferase

Constructs were made using an anti-CD19 CAR cassette as described in WO 2012/079000, which is hereby incorporated-by-reference in its entirety for all purposes), and a Luciferase-RDE1 (3' UTR of IFNg, Gold1) insert, a Luciferase-RDE2 (3'-UTR of IL-2, Gold2) insert, a Luciferase-RDE3 (3'-UTR of IL-2 modified as described above to remove the mir186 sites, Gold3), or a Luciferase-3'-UTR (a 3'-UTR that does not confer differential transgene translation in response to metabolic state of the cell, 3'-UTR). Combinations of these inserts/cassettes shown in FIG. 3 were placed in the similar lenti virus constructs. The anti-CD19 CAR cassette and the insert with the luciferase-RDE are transcribed in opposite directions, and the control regions for each are located in between the two insert/ cassettes. The control region for the Luciferase-RDE insert and Luciferase-3'-UTR were either a MinP promoter or an NFAT promoter. The control region of the anti-CD19 CAR cassette was the MND promoter, and CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells.

Figure 3:
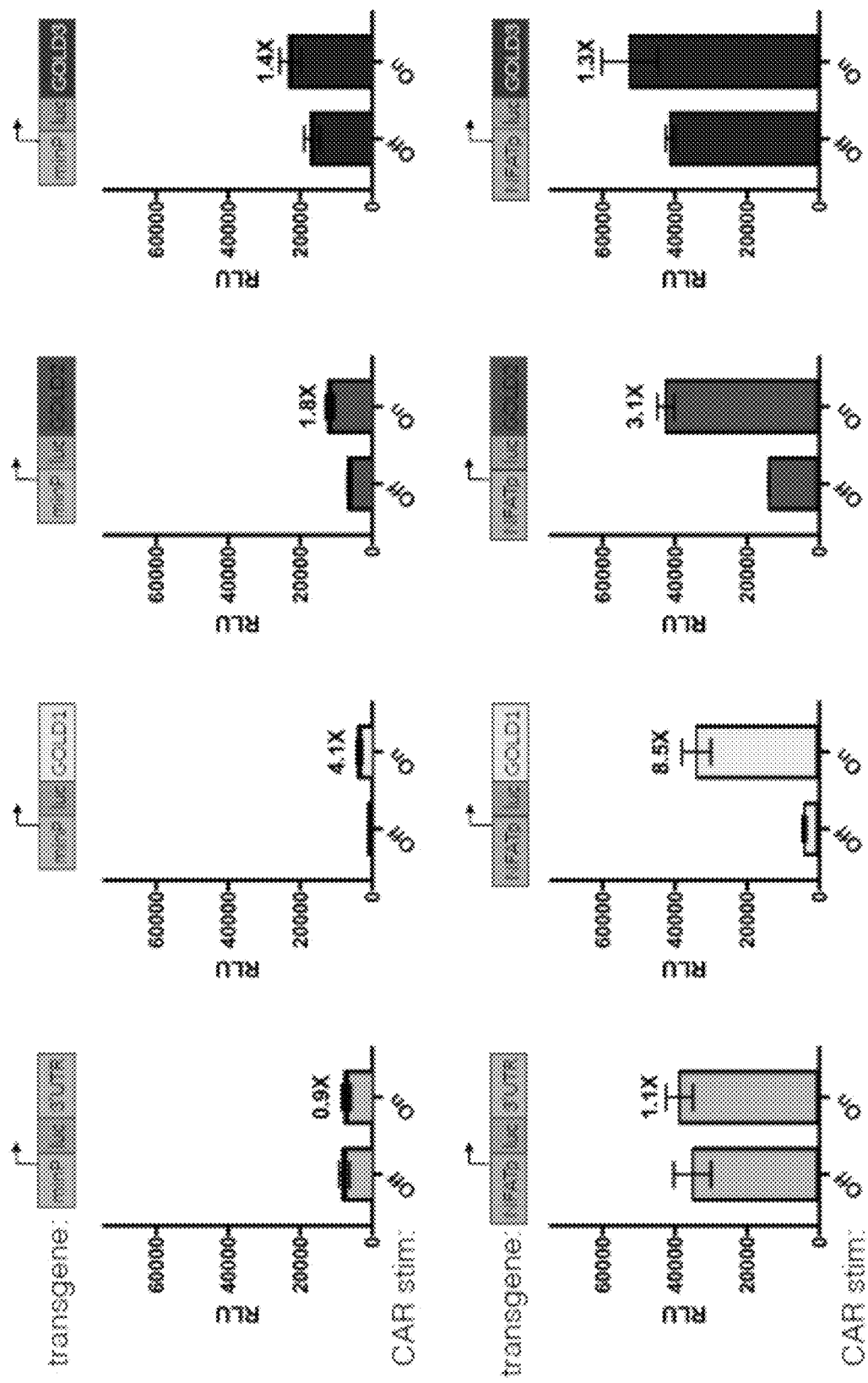
FIG. 3 shows a graph for bioluminescence from T-cells with luciferase controlled by the RDEs Gold1, Gold2, or Gold3 following activation of the T-cell by Raji target cells (activate CAR) as compared to bioluminescence of T-cells at resting.

FIG. 3 shows that the transduced T-cells had an increase in bioluminescence when cultured with Raji target cells (activate CAR) as compared to bioluminescence of T-cells at resting for constructs with RDE1 (Gold1), RDE2 (Gold2), or RDE3 (Gold3). The T-cells with a NFAT promoter and the RDE1 showed a larger on-off response than T-cells with a MinP promoter and the corresponding RDE. Under all conditions, T-cells with an RDE controlling luciferase had lower amounts of bioluminescence than T-cells with luciferase cassettes that were not controlled by an RDE. Combined with the MinP promoter, RDE1 gave a 4.1-fold increase in bioluminescence with CAR stimulation, RDE2 gave a 1.8-fold increase in bioluminescence, and RDE3 gave a 1.4-fold increase. Combined with the NFAT promoter, RDE1 gave a 8.5-fold increase in bioluminescence with CAR stimulation, RDE2 gave a 3.1-fold increase in bioluminescence, and RDE3 gave a 1.3-fold increase. With either promoter, the RDE3 construct gave the highest amount of bioluminescence, the RDE1 construct gave the lowest amount of bioluminescence, and the RDE2 construct gave an amount of bioluminescence between RDE3 and RDE1.

Example 9: An RDE Construct for Expressing IL-12

Constructs were made using an anti-CD19 CAR cassette as described in WO 2012/079000, which is hereby incorporated-by-reference in its entirety for all purposes), and an IL-12-RDE1 (3'-UTR of IFNg) insert or an IL-12 3'-UTR (a 3'-UTR that does not confer differential transgene translation in response to metabolic state of the cell). The anti-CD19 CAR cassette and the insert with the IL-12-RDE1 are transcribed in opposite directions, and the control regions for each are located in between the two insert/cassettes. The control region for the IL-12-RDE1 insert and IL-12 3'-UTR were either a minP promoter or an NFAT promoter. The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set, CD19+ Raji B cells were incubated with the transduced T cells for 24 h. At 24 h, the T cells were stained for CD25 and CD69, which are activation markers, and subject to flow cytometry to measure these markers. IL-12 expression in the T cells was measured by ELISA.

Figure 4:
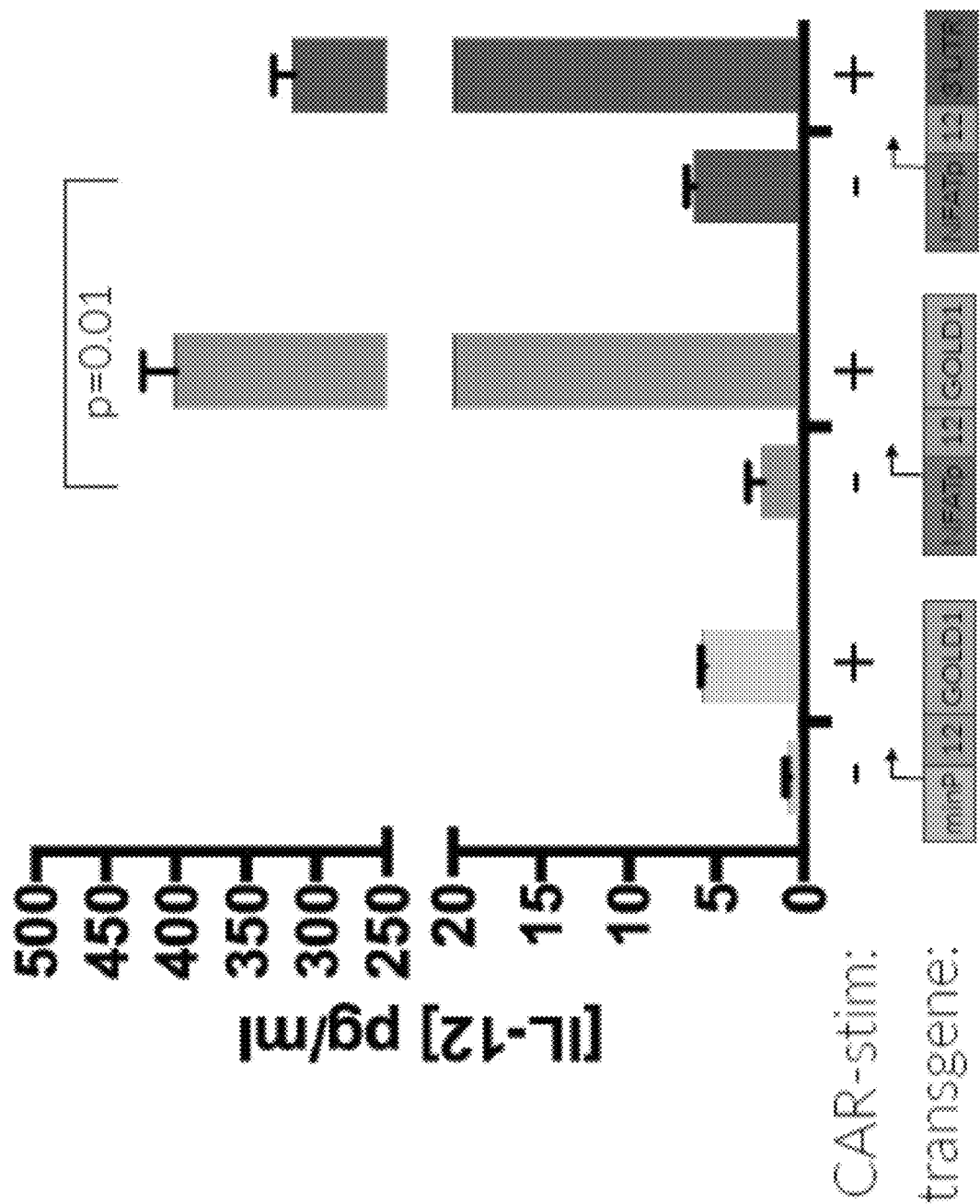
FIG. 4 shows a graph for the IL-12 expression from T-cells with IL-12 expression controlled by an RDE following activation of the T-cell by Raji target cells (activate CAR) as compared to IL-12 expression of T-cells at resting.

FIG. 4 shows that the transduced T-cells had an increase in IL-12 expression when cultured with Raji target cells (activate CAR) as compared to IL-12 expression of T-cells at resting using constructs controlled by the MinP promoter or NFAT promoter. T-cells with the NFAT promoter and RDE1 (Gold1) showed a 168-fold change in IL-12 expression form resting to CAR stimulation. T-cells with the NFAT promoter and a 3'-UTR (not responsive to CAR stimulation, 3'-UTR) showed a 50-fold change in expression, and a minP promoter with RDE1 (Gold1) showed a 6.3 fold change in expression.

Example 10: AU Elements and Steady State Expression

Figure 5:
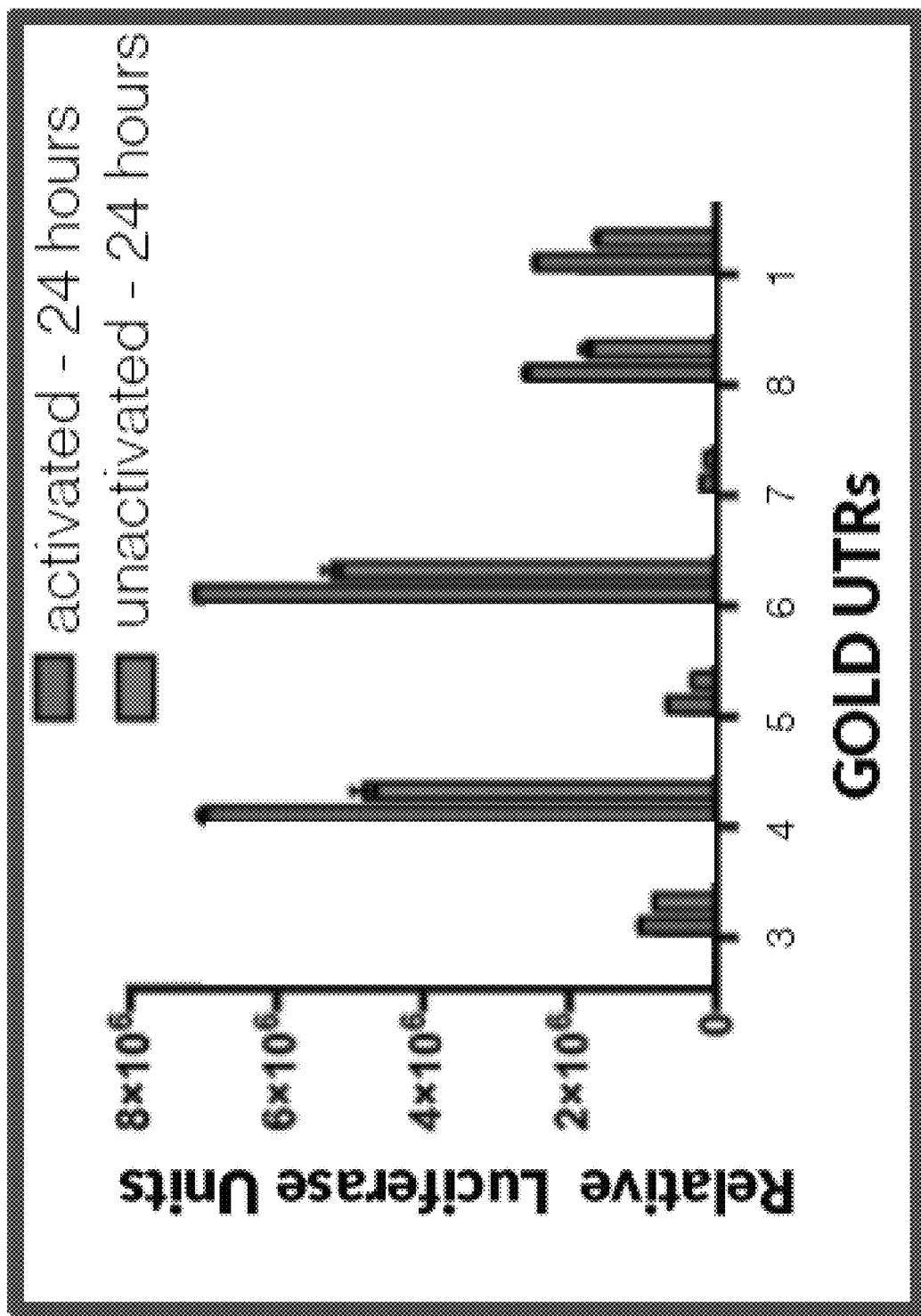
FIG. 5 shows basal luciferase expression and activated luciferase expression for luciferase constructs utilizing different RDEs as control elements in Jurkat cells.

Constructs were made with different RDEs operably linked to a nucleic acid encoding luciferase. The different RDEs used were AU 4 (CTLA4), AU 13 (IL-5), AU 14 (IL-6), AU 15 (IL-9), AU 16 (IL-10), AU 17 (IL-13), and AU 101 (IFNg). These luciferase-AU constructs were transduced into primary T-cells. After the cells returned to the resting stage they were plated and sham induced (basal) or induced with anti-CD3 and anti-CD28 antibody (activated). At 24 hours post activation the amount of luciferase units in each was measured. These amounts are plotted in the bar graph of FIG. 5.

The AU elements in this example had different basal expression levels, different induced expression levels (at 24 hours), and different levels of fold induction. The AU constructs showed different amounts of basal expression, different amounts of induced expression and different amounts of fold induction (or dynamic range).

Example 11: AU Elements and Expression Parameters

Constructs were made with different RDEs operably linked to a nucleic acid encoding luciferase. The different RDEs used were AU 2 (CSF2), AU 3 (CD247), AU 5 (EDN1), AU 7 (SLC2A1), AU 10 (Myc), AU 19 (TMEM-219), AU 20 (TMEM-219snp), AU 21 (CCR7), AU 22 (SEM-A4D), AU 23 (CDC42-SE2), and AU 101 (IFNg). These luciferase-AU constructs were transduced into primary T-cells. After the cells returned to the resting stage they were plated and either not treated (basal) or activated with anti-CD3 and anti-CD28 antibody (activated). At 24 hours post activation the amount of luciferase units in each was measured. These amounts are plotted in the bar graph of FIG. 6. Alternatively, after the cells returned to resting stage they were plated into 96-well plates in quadruplicate for measuring at each time point: 1 day, 3 days, 6 days and 8 days. The cells were either not treated or activated with anti-CD3 and anti-CD28 antibody, and luciferase activity was measured at 1 day, 3 days, 6 days and 8 days. These results are plotted in the bar graph of FIG. 7, and shown in Table 1 below. FIG. 8 shows selected data plotted in a bar graph. The numbers in parentheses in Table 1 below are the Luciferase Units on Days 3, 6, and 8 divided by the Luciferase Units of Day 1.

Figure 6:
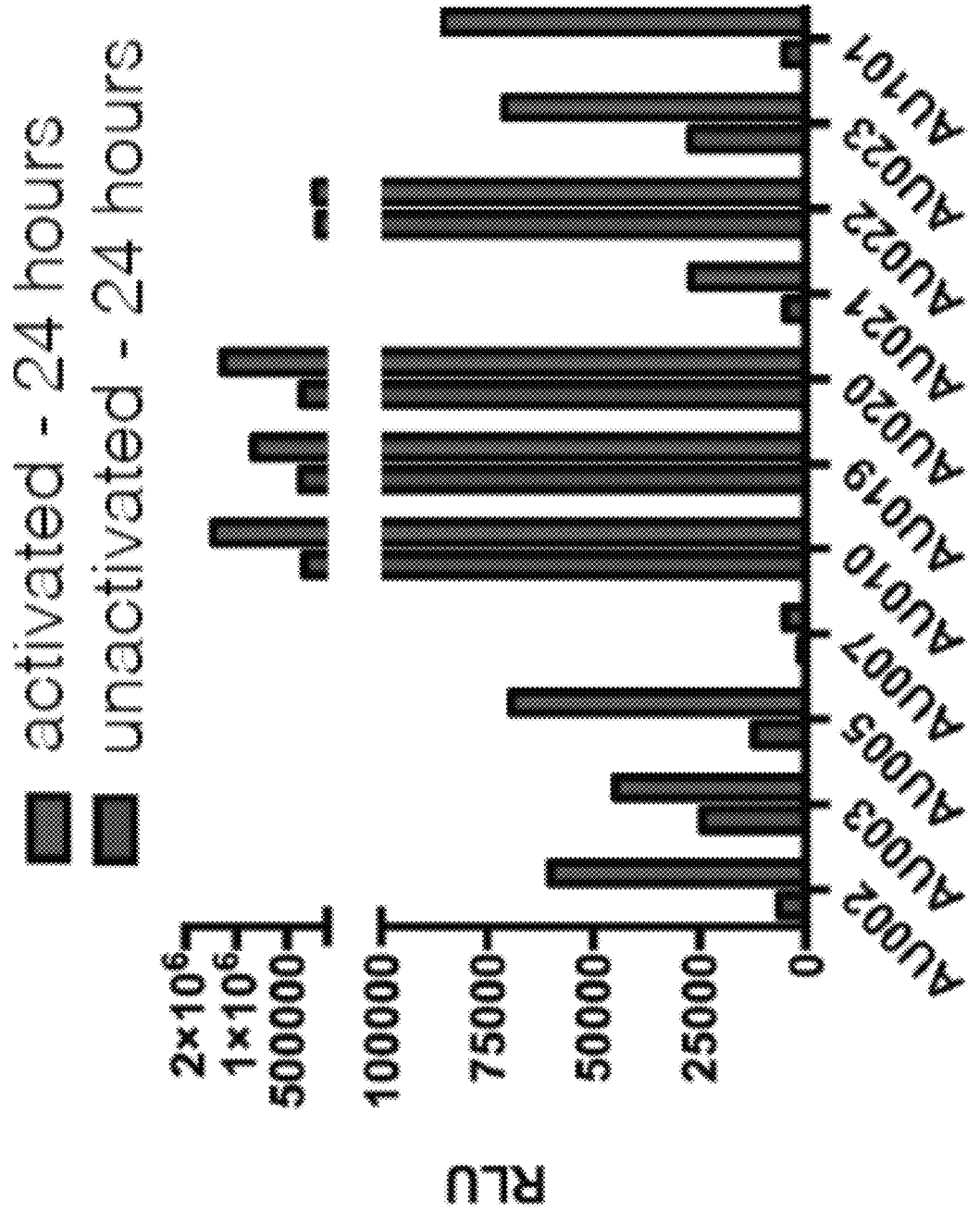
FIG. 6 shows basal luciferase expression and activated luciferase expression for luciferase constructs utilizing different RDEs as control elements in primary T-cells.
Figure 7:
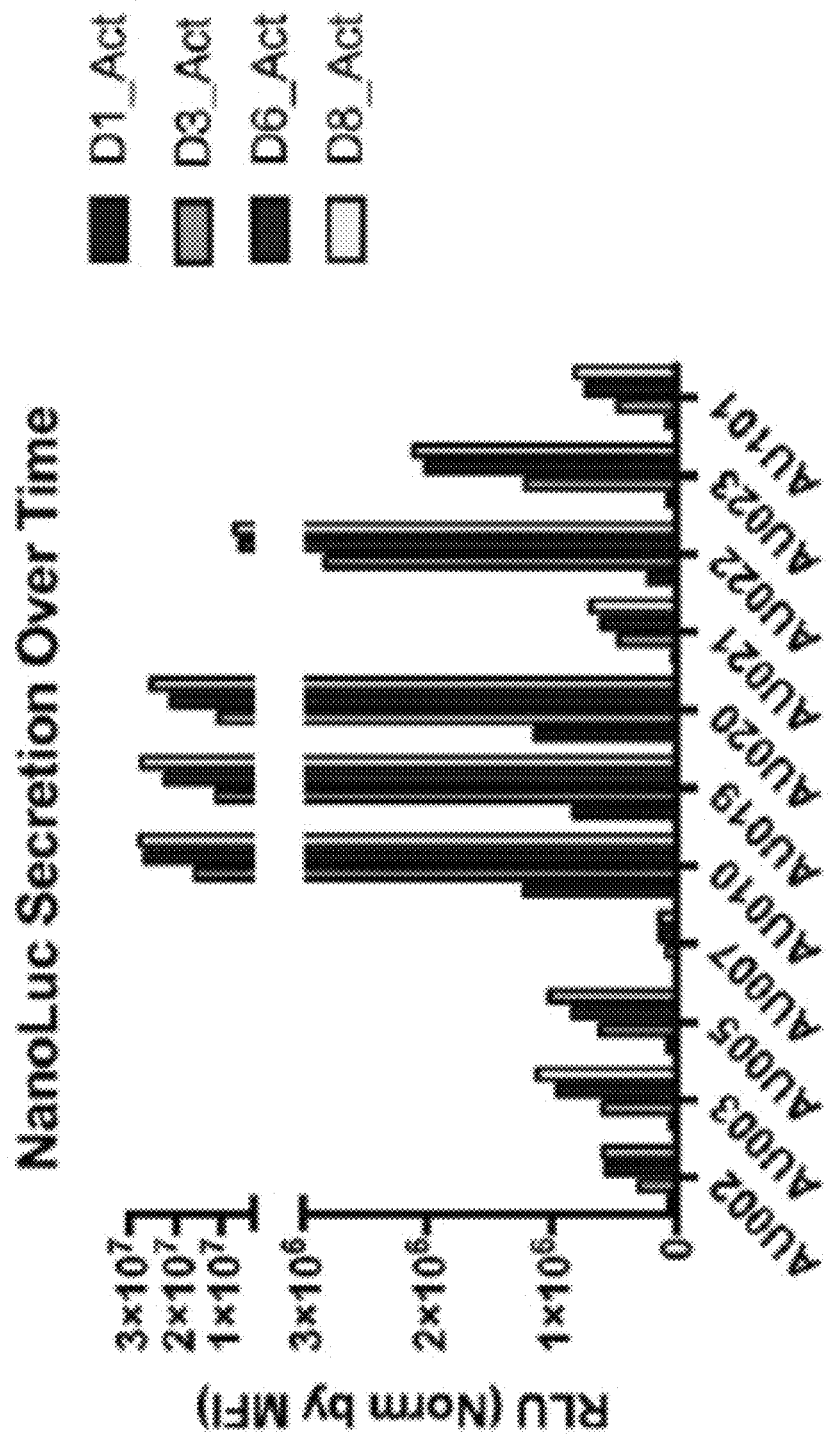
FIG. 7 shows activated luciferase/basal luciferase expression after 1, 3, 6, and 8 days for luciferase constructs utilizing different RDEs as control elements.
Figure 8:
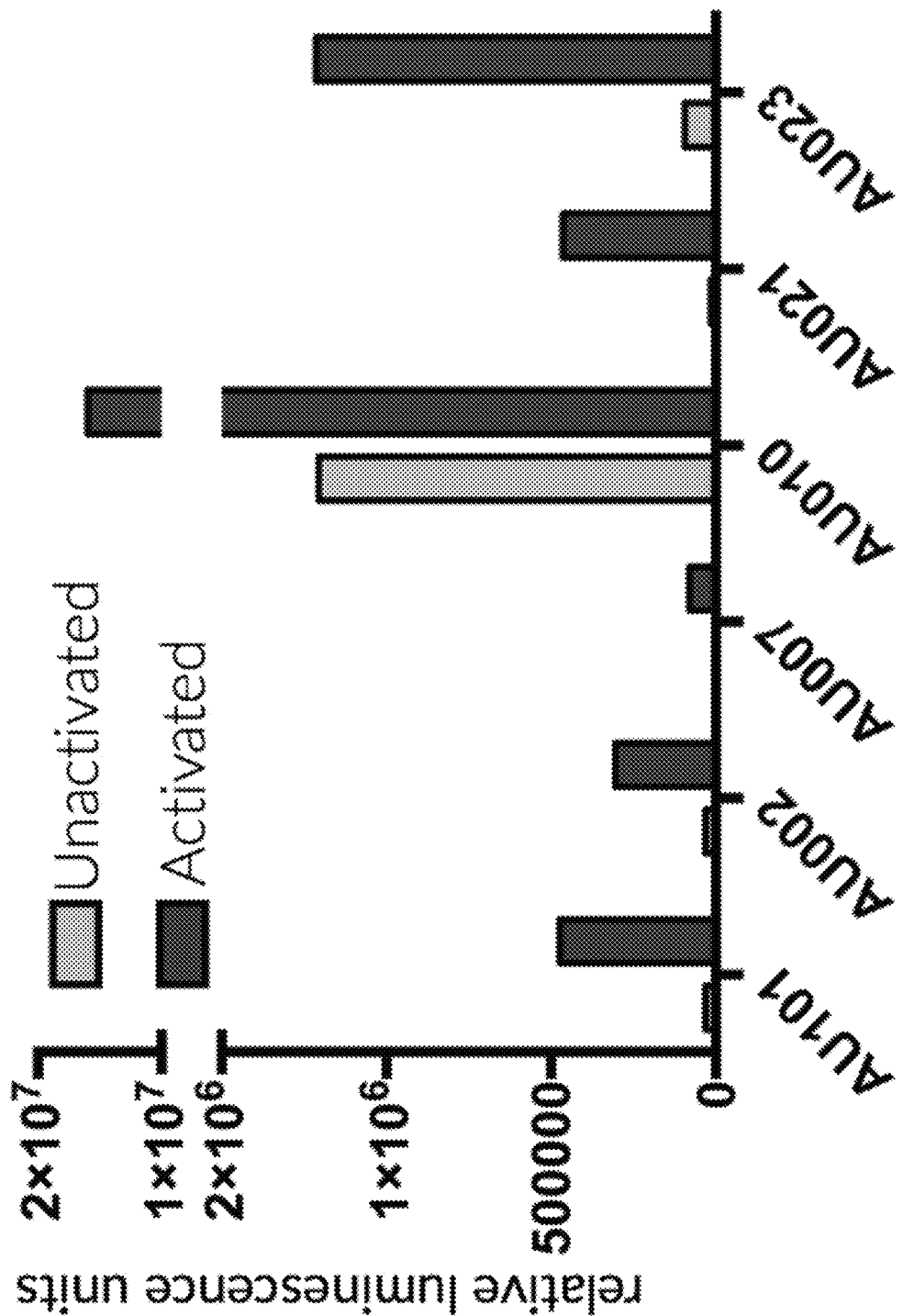
FIG. 8 shows basal luciferase expression and activated luciferase expression for luciferase constructs utilizing different RDEs as control elements.

The AU elements in FIG. 6, FIG. 7 and Table 1 had different basal expression levels, different induced expression levels (at 24 hours), and different levels of fold induction. The basal expression levels differed over an about 2000 fold range for these AU elements (AU 7 to AU 20), and the induced expression levels differed over an about 5500 fold range (AU 7 to AU 10). Basal expression for the constructs ranged from 1390 for AU 7 (SLC2A1) to 2,927,000 for AU 20 (TMEM-219snp). Activated expression ranged from 4914 for AU 7 (day 1) to 27,800,0000 for AU 10 (day 8). FIG. 8 and Table 1 show that some AU elements had lower levels of output, for example, AU 101 (IFNg), AU 2 (CSF2), AU 5 (EDN1), AU 7 (SLC2A1), AU 21 (CCR7), and AU 23 (CDC42-SE2). Some AU elements had intermediate amounts of output: AU 19 (TMEM-219) and AU 22 (SEM-A4D). And some AU element had high output: AU 20 (TMEM-219snp) and AU 10 (Myc).

Figure 9:
FIG. 9 shows the dynamic range (activated luciferase/basal luciferase) measured 1, ¾, 6, and 8 days after activation for luciferase constructs utilizing different RDEs as control elements.
Figure 10:
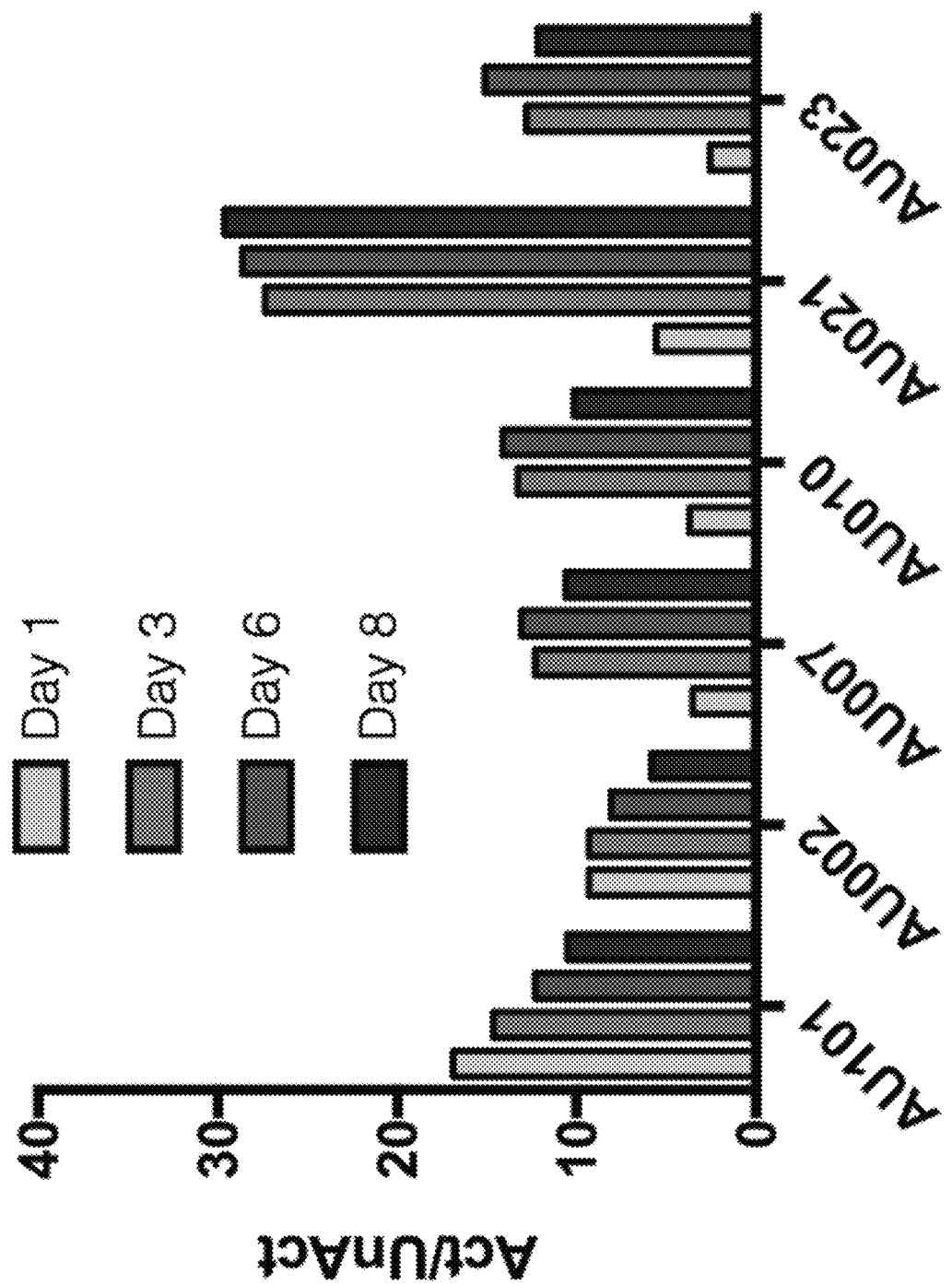
FIG. 10 shows the dynamic range (activated luciferase/basal luciferase) measured 1, ¾, 6, and 8 days after activation for luciferase constructs utilizing different RDEs as control elements.

The Luciferase data was also analyzed for dynamic range (fold induction or luciferase activated/luciferase basal) of each luciferase-AU construct. The dynamic range (fold induction) for each AU construct at Days 1, ¾ (activated expression was measured on Day 3 and basal expression was measured on Day 4), 6 and 8. This data is shown below in Table 2, and plotted in bar graphs in FIG. 9 and FIG. 10.

TABLE 2

| AU Construct | Fold Induction | | | |
|---|---|---|---|---|
| | Day 1 | Day 3/4* | Day 6 | Day 8 |
| AU 2 | 9.3 | 9.3 | 8.1 | 5.8 |
| AU 101 | 16.9 | 14.6 | 12.3 | 10.5 |
| AU 5 | 5.7 | 11.9 | 10.1 | 9.4 |
| AU 21 | 5.6 | 27.3 | 28.6 | 29.6 |
| AU 3 | 1.8 | 6.7 | 8.1 | 6.8 |
| AU 20 | 3.1 | 7.3 | 9.3 | 8.7 |
| AU 10 | 3.7 | 13.2 | 14.1 | 10.2 |
| AU 7 | 3.5 | 12.3 | 13.1 | 10.6 |
| AU 23 | 2.6 | 12.8 | 15.1 | 12.2 |
| AU 19 | 2.3 | 9.3 | 12.9 | 13.8 |
| AU 22 | 1.2 | 4.6 | 6.9 | 7.1 |

*Induction was measured on Day 3 and basal was measured on Day 4.

At Day 1 dynamic range (fold induction=activated/basal) ranged from about 1 (AU 22) to about 17 (AU 101). At Day ¾, dynamic range varied from about 4.5 (AU 22) to about 27 (AU 21). At Day 6, dynamic range varies from about 7 (AU 22) to about 29 (AU 21). On Day 8, dynamic range varied from about 7 (AU 22) to about 30 (AU 21). The AU constructs showed a number of related patterns. AU 2 and AU 101 showed a rapid increase in dynamic range on Day 1, and then the dynamic range decreased on days 6 and 8.

TABLE 1

| | Luciferase Units | | | |
|---|---|---|---|---|
| AU Construct | Day 1 | Day 3 | Day 6 | Day 8 |
| AU 2 (CSF2) | 60051 | 306035 (5) | 578305 (10) | 591953 (10) |
| AU 101 (IFNg) | 85816 | 473395 (6) | 724129 (8) | 817447 (10) |
| AU 5 (EDN1) | 69391 | 613921 (9) | 838040 (12) | 1023000 (15) |
| AU 3 (CD247) | 44939 | 595753 (13) | 961839 (21) | 1116000 (25) |
| AU 20 (TMEM-219snp) | 1135000 | 10750000 (9) | 21020000 (19) | 25480000 (22) |
| AU 10 (Myc) | 1233000 | 16020000 (13) | 26780000 (22) | 27800000 (23) |
| AU 7 (SLC2A1) | 4914 | 80906 (16) | 132974 (27) | 136537 (28) |
| AU 21 (CCR7) | 27128 | 465140 (17) | 604016 (22) | 692715 (26) |
| AU 23 (CDC42-SE2) | 71105 | 1215000 (17) | 2012000 (28) | 2110000 (30) |
| AU 22 (SEM-A4D) | 226815 | 2829000 (12) | 6106000 (27) | 7396000 (33) |
| AU 19 (TMEM-219) | 833146 | 11260000 (14) | 22560000 (27) | 27500000 (33) |

AU 5 and AU 21 show increasing dynamic range from day 0 to day ¾, and then the dynamic range is maintained through days 6 and 8. AU 3, AU 20, AU 10, AU 7 and AU 23 showed rising dynamic range from day 0 to day 6, and then the dynamic range decreased on day 8. AU 19, and AU 22, showed rising dynamic ranges from day 0 to day 8.

AU 21 and AU 23 showed accelerating dynamic range and these AU constructs also had low basal expression (day 1=4865 and 27363, respectively). AU 2 and AU 101 showed decreasing dynamic range from 24 hours to 72 hours and these AU elements also had low basal expression. AU 5 and AU 20 also showed decreasing dynamic range from day 1 to day ¾ (though more expression than AU 2 and AU 101) and AU 5 had low basal expression whereas AU 20 had high basal expression. AU 10, AU 19 and AU 22 showed consistent dynamic range from day 1 to day ¾ and had high basal levels of expression. AU 3 and AU 7 also had consistent dynamic range from day 1 to day ¾ and had low basal expression levels.

The above data shows that different AU elements have different temporal effects on expression from days 1-8. Some AU elements show accelerating dynamic range over different portions of the time range. The AU elements show different amounts of total expression ($C_{max}$) and different times to maximum expression ($T_{max}$). The AU elements also show different maximum dynamic ranges and time to reach these maximums. These differing kinetics of expression can be used to provide customized basal, $C_{max}$, $T_{max}$ dynamic range, and time to max dynamic range for a desired transgene. These differing kinetics can also be used to provide temporally distinct expression for two transgenes in a cell after activation of the cell.

Example 12: AU Element Control with Glucose and Galactose

Figure 11:
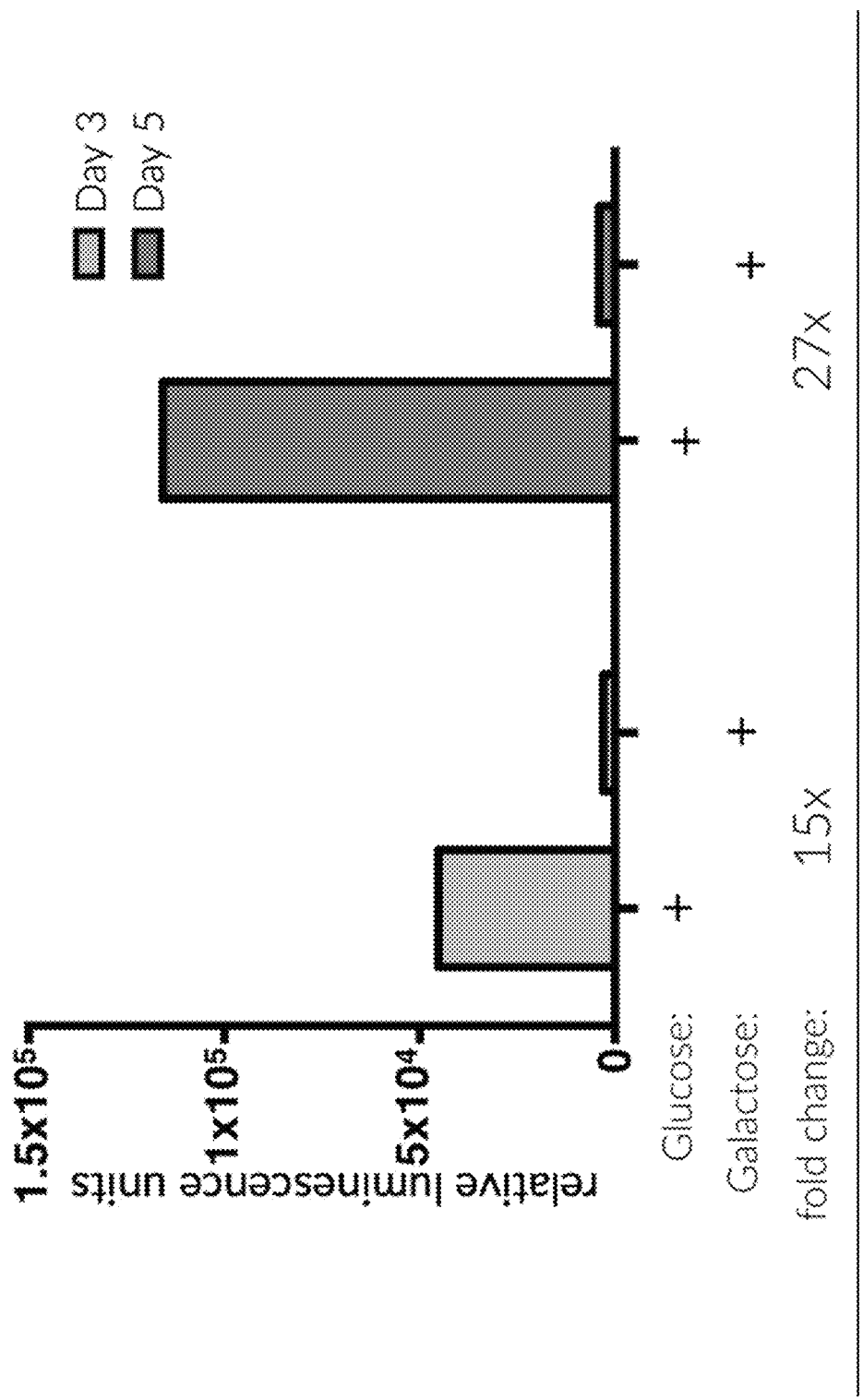
FIG. 11 shows the impact on luciferase expression for luciferase constructs utilizing an RDE as a control element in the presence of glucose and galactose.

Constructs were made with different RDEs operably linked to a nucleic acid encoding luciferase. The RDE was an AU element responsive to glycolytic state of the cell. The AU element-luciferase constructs were transduced into T-cells. After the cells reached the resting state, they were split into wells and fed media including either glucose or galactose. Luciferase activity was measured on days 3 and 5. These results are shown in the bar graph of FIG. 11. The results show that glucose increased expression of luciferase compared to galactose and the amount of expression increased from days 3 to 5. On day 3 the glucose treated cells had 15× more expression of luciferase than the galactose treated cells and on day 5 this had grown to 27× more expression.

Example 13: Delivery and Design of a Viral Payload

A Smart Car is made using the third generation anti-CD19 CAR cassette described in WO 2012/079000, which is hereby incorporated-by-reference in its entirety for all purposes), and the RNA control device, 3XL2bulge9 (Win and Smolke 2007 Proc. Natl Acad. Sci. 104 (36): 14283-88, which is hereby incorporated by reference in its entirety for all purposes). A nucleic acid encoding the 3XL2bulge9 control device is engineered into the anti-CD19 CAR cassette in an appropriate expression vector. The anti-CD19 Smart CAR and anti-CD19 CAR constructs are transfected by routine methods into different populations of T-cells (Jurkat cells and/or primary human T-cells), and stable populations of T-cells are selected using appropriate antibiotics (or other selection schemes). T-cell populations with anti-CD19 Smart CARs (CD19⁻/CD22⁻/CD3⁺) and T-cell populations with anti-CD19 CARs (CD19⁻/CD22⁻/CD3⁺) are activated by co-incubation with anti-CD3/CD28 beads.

Third generation Lentiviral packaging, envelope, and transfer plasmids are obtained from addgene. The Rev encoding packaging plasmid is engineered to include the AU 101 (INFg) RDE in the 3'-UTR of Rev. The modified Rev packaging plasmid, the Gag Pol packaging plasmid, and the envelope plasmid are transfected into anti-CD19 T-lymphocyte cells. A transfer plasmid is engineered to include GFP as the transgene in the transfer plasmid. This transfer plasmid is also transfected into the anti-CD19 CAR T-lymphocyte cells.

Anti-CD19 Smart CAR T-lymphocytes are co-cultured with CD19+/CD22+/CD3− Ramos target cells at Smart CAR T-lymphocyte:Raji target ratios of 2:1, 5:1, and 10:1. Ligand for the RNA control device, theophylline is added to the culture medium at concentrations in the range of 2 μM to 2 mM (2 μM, 10 μM, 20 μM, 100 μM, 200 μM, 1 mM, and 2 mM). The Smart-CAR T-cells and the Raji cells are grown together for 48 hours.

At the end of the incubation period, the culture media is separated from the T-lymphocytes and Raji cells. Viral titer in the supernatant is measured using an ELISA with anti-lentivirus antibody reagents. Infectivity and payload delivery by the viruses is tested by infecting HEK 293 cells with the virus, and after a suitable incubation time measuring GFP fluorescence from the transduced HEK 293 cells.

Example 14: Payload Delivery Using Gold in a Mouse Lymphoma Model

Constructs were made using an anti-CD19 CAR cassette as described in WO 2012/079000, which is hereby incorporated-by-reference in its entirety for all purposes), and a Luciferase-AU (3' UTR of IL-6) insert. These constructs were placed in a bicistronic lenti virus construct. The anti-CD19 CAR cassette and the insert with the luciferase-RDE are transcribed in opposite directions on the bicistronic vector, and the control regions for each are located in between the two insert/cassettes. The control region for the Luciferase-RDE insert was a MinP promoter. The control region of the anti-CD19 CAR cassette was the MND promoter. CD4+ T-cells were transduced with the bicistronic construct.

The transduced T cells were allowed to return to resting state, and then were tested after stimulation as follows. For the 'no stimulation' set, transduced T-cells were incubated for 24 h alone in medium. For the 'Raji co-culture' set CD19+ Raji B cells were incubated with the transduced T cells for 24 h. At 24 h, the T cells were stained for CD25 and CD69, which are activation markers, and subject to flow cytometry to measure these markers and luciferase expression in the T cells. These in vitro results showed that the anti-CD19 CAR T-cells made luciferase after activation of the T-cells through the CAR.

These anti-CD19 CAR T-cells were also tested in a mouse model for lymphoma. CD19+ Raji cells were implanted in the flanks of NSG mice. After tumor formation, the anti-CD19 CAR T-cells were injected into the mice and the mice were scanned for luminescence. Imaging of the mice showed luminescence at the tumor sites from anti-CD19 CAR T-cells that have been activated by the CD19 positive tumor. The amount of luminescence increased over time as more T-cells were activated.

Example 15: Payload Delivery to αvβ6 Positive Solid Tumor

A nucleic acid encoding a knottin as described in Silverman et al., J. Mol. Biol. 385:1064-75 (2009) and Kimura et al, Proteins 77:359-69 (2009), which are incorporated by reference in their entirety for all purposes is operably linked to a nucleic acid encoding the CAR components aCD43z, CD8Hinge, CD8transmembrane, 41BB(CD28 or other costim), and CD3z to make a nucleic acid encoding an anti-αvβ6 CAR.

The nucleic acid encoding the anti-αvβ6 CAR is transfected by routine methods into T-cells (Jurkat cells and/or primary human T-cells), and stable populations of T-cells are selected using appropriate antibiotics (or other selection schemes). T-cell populations with anti-αvβ6 CARs are activated by co-incubation with anti-CD3/CD28 beads. These cells are also engineered with an expression cassette encoding IL-12 operably linked to the Gold element from INFg or AU 21 (CCR7) is placed under the control of the promoter Min P.

The anti-αvβ6 CAR T-cells are incubated in wells with αvβ6 tumor cells. After incubation, the wells are tested for secretion of IL-12 from the anti-αvβ6 CAR T-cells. anti-αvβ6 CAR T-cells secrete IL-12 when incubated with αvβ6 tumor cells, and the controls show low or no secretion when the CAR T-cell is not stimulated.

Example 16: An Anti-Onco CD 43 CAR for AML

A single chain antibody for onco-sialylated CD 43 was made using an anti-onco-sialylated CD 43 antibody. The nucleic acid encoding this single-chain antibody was combined with a nucleic acid encoding the CAR components aCD43z, CD8Hinge, CD8transmembrane, 41BB(CD28 or other costim), and CD3z to make a nucleic acid encoding an anti-onco-sialylated CD 43 CAR.

The nucleic acid encoding the anti-onco-sialylated CD 43 CAR is transfected by routine methods into T-cells (Jurkat cells and/or primary human T-cells), and stable populations of T-cells are selected using appropriate antibiotics (or other selection schemes). T-cell populations with anti-onco-sialylated CD 43 CARs are activated by co-incubation with anti-CD3/CD28 beads.

Example 17: Payload Delivery to CD 43 Positive AML

An expression cassette encoding IL-12 operably linked to the Gold element from INFg or AU 21 (CCR7) is placed under the control of the promoter Min P, and engineered into the anti-onco-sialylated CD 43 CAR T-cell.

The anti-onco-sialylated CD 43 CAR T-cells are incubated in wells with AML cells. After incubation, the wells are tested for secretion of IL-12 from the anti-onco-sialylated CD 43 CAR T-cells. Anti-onco-sialylated CD 43 CAR T-cells secrete IL-12 when incubated with AML cells, and the controls show low or no secretion when the CAR T-cell is not stimulated.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method of expressing a plurality of transgenes, comprising the steps of:

obtaining a primary T-cell comprising a chimeric antigen receptor, a first heterologous nucleic acid comprising a polynucleotide encoding a first transgene, and a polynucleotide encoding a first RNA destabilizing element (RDE), wherein the first RDE is an AU 101 (Interferon gamma or IFNg) or an AU14 (IL6), wherein a first RDE binding protein binds to the first RDE and regulates expression of the first transgene, a second heterologous nucleic acid comprising a polynucleotide encoding a second transgene, and a polynucleotide encoding a second RDE, wherein the second RDE is an AU 101 (Interferon gamma or IFNg) or an AU14 (IL6), wherein a second RDE binding protein binds to the second RDE and regulates expression of the second transgene, wherein the first and second heterologous nucleic acids are transcribed to make a first transcript encoding the first transgene operably linked to the first RDE, and a second transcript encoding the second transgene operably linked to the second RDE;

binding the primary T-cell to a target ligand for the chimeric antigen receptor at a target site in a subject, wherein binding of the ligand by the chimeric antigen receptor activates the primary T-cell and the T-cell proliferates, wherein activation of the primary T-cell changes binding of the first RDE by the first RDE binding protein and binding of the second RDE by the second RDE binding protein; and expressing the first and second transgenes, wherein the first and second transgenes have increased levels of expression after activation of the primary T-cell compared to the level of expression before activation of the primary T-cell.

2. The method of claim 1, wherein the first transgene encodes a cytokine, a FasL, an antibody, a growth factor, a chemokine, an enzyme that cleaves a polypeptide or a polysaccharide, a granzyme, a perforin, a reporter, or a checkpoint inhibitor.

3. The method of claim 2, wherein the second transgene encodes a cytokine, a FasL, an antibody, a growth factor, a chemokine, an enzyme that cleaves a polypeptide or a polysaccharide, a granzyme, a perforin, a reporter, or a checkpoint inhibitor.

4. The method of claim 2, wherein the first transgene encodes an IL-2, an IL-12, an IL-15, an IL-18, or an TNF-α.

5. The method of claim 3, wherein the second transgene encodes an IL-2, an IL-12, an IL-15, an IL-18, or an TNF-α.

6. The method of claim 2, wherein the first transgene encodes an anti-4-1BB antibody.

7. The method of claim 3, wherein the second transgene encodes an anti-4-1BB antibody.

8. The method of claim 1, wherein the first transgene encodes a CD40L.

9. The method of claim 1, wherein the second transgene encodes a CD40L.

10. The method of claim 1, wherein the first transgene encodes a Hsp60 or a Hsp70.

11. The method of claim 1, wherein the second transgene encodes a Hsp60 or a Hsp70.

12. The method of claim 1, wherein the chimeric antigen receptor is an anti-DLL3 chimeric antigen receptor.

13. The method of claim 12, wherein the ligand is a DLL3 found on a target cell.

14. The method of claim 13, wherein the target cell is a tumor cell.

15. The method of claim 14, wherein the tumor cell is a small cell lung cancer cell.

16. The method of claim 14, wherein the tumor cell is a melanoma cell.

17. The method of claim 14, wherein the tumor cell is an isocitrate dehydrogenase 1, mutant glioma cell.

* * * * *